United States Patent [19]
Gelfand et al.

[11] Patent Number: 6,127,155
[45] Date of Patent: Oct. 3, 2000

[54] STABILIZED THERMOSTABLE NUCLEIC ACID POLYMERASE COMPOSITIONS CONTAINING NON-IONIC POLYMERIC DETERGENTS

[75] Inventors: David H. Gelfand, Oakland; Susanne Stoffel, El Cerrito; Randall K. Saiki, Richmond, all of Calif.

[73] Assignee: Roche Molecular Systems, Inc., Pleasanton, Calif.

[21] Appl. No.: 07/873,897

[22] Filed: Apr. 24, 1992

Related U.S. Application Data

[60] Continuation of application No. 07/387,003, Jul. 28, 1989, abandoned, which is a division of application No. 07/143,441, Jan. 12, 1988, abandoned, which is a continuation-in-part of application No. 07/063,509, Jun. 17, 1987, Pat. No. 4,889,818, which is a continuation-in-part of application No. 06/899,241, Aug. 22, 1986, abandoned.

[51] Int. Cl.$^7$ .............................. C12N 9/96; C12N 9/00; C12P 19/34; C12P 21/06
[52] U.S. Cl. .......................... 435/188; 435/6; 435/69.1; 435/91.1; 435/91.2; 183/471; 183/478; 183/488; 183/814
[58] Field of Search .............................. 435/91, 183, 188, 435/194, 814, 6, 69.1, 91.1, 91.2, 471, 478, 488; 935/18

[56] References Cited

U.S. PATENT DOCUMENTS

| | | | |
|---|---|---|---|
| 4,379,839 | 4/1983 | Spiegelman | 935/18 X |
| 4,409,200 | 10/1983 | Feller et al. | 435/7 X |
| 4,683,195 | 7/1987 | Mullis et al. | 435/6 |
| 4,683,202 | 7/1987 | Mullis | 435/91 |
| 4,889,818 | 12/1989 | Gelfand et al. | 435/194 |
| 4,943,531 | 7/1990 | Goff et al. | 435/194 X |

FOREIGN PATENT DOCUMENTS

| | | |
|---|---|---|
| 258017 | 3/1988 | European Pat. Off. . |
| 8906691 | 7/1989 | WIPO . |

OTHER PUBLICATIONS

Stenesh et al., 1972, *Biochim Biophys. Acta* 272: 156–166.
Air et al., 1974, *FEBS Letters* 38 (3):277–281.
Edgar et al. 1975, *Abst. ASM Ann. Mtg.* 75:151.
Chien et al., 1976, *Chem. Abst.* 85:180 (Abstract No. 155559t).
Chien et al., 1976, *J. Bact.* 127(3):1550–1557.
Fabry et al., 1976, *Biochim. Biophys. Acta* 435:228–235.
Kaledin et al., 1980, *Chem. Abst.* 93:377 (Abstract No. 40169p).
Kaledin et al., 1980, *Biochem.* 45(4):494–501.
Kaboev et al., 1981, *J. Bact.* 145(1):21–26.
Kaledin et al., 1981, *Biochem.* 46:1247–1254.
Kaledin et al., 1982, *Biochem.* 47:1515–1521.
Kaledin et al., 1983, *Chem. Abst.* 98:298, (Abstract No. 49311q).
Ruttiman et al., 1985, *Eur. J Biochem.* 149:41–46.
Klimczak, et al., 1986, *Biochem.* 25(17):4850–4855.
Rossi, et al., 1987, *System. Appl. Microbiol.* 7:337–341.
Kogan et al., 1987, *N. Eng. J. Med.* 317:985–990.
Verhoeven et al., 1988, *ASM Ann. Mtg. Abst.* 88:214 (Abstract No. K–47).
Saiki et al., 1988, *Science* 239:487–491.
Lawyer et al., 1989, *J. Biol. Chem.* 264(11):6427–6437.
Decision dated Dec. 7, 1999 of the District Court of the Northern District of California in Civil Action No. C–93–1748VRW.

*Primary Examiner*—David M. Naff
*Attorney, Agent, or Firm*—Stacey R. Sias; Douglas A. Petry

[57] ABSTRACT

A purified thermostable nucleic acid polymerase is obtained that has unique characteristics. Preferably the nucleic acid polymerase is DNA polymerase isolated from a *Thermus aquaticus* species and has a molecular weight of about 86,000–95,000 daltons. The thermostable nucleic acid polymerase may be native or recombinant and may be used in a temperature-cycling chain reaction wherein at least one nucleic acid sequence is amplified in quantity from an existing sequence with the aid of selected primers and nucleotide triphosphates. The nucleic acid polymerase is preferably stored in a buffer containing non-ionic detergents that lends stability to the nucleic acid polymerase. A preferred buffer contains glycerol, polyoxyethylated sorbitan monolaurate, ethoxylated nonyl phenol and gelatin.

18 Claims, 8 Drawing Sheets

TAQ DNA POLYMERASE SEQUENCE    FIG.1-1

```
    -120              -100                -80
        BglII                          PvuII
AAGCTCAGATCTACCTGCCTGAGGGCGTCCGGTTCCAGCTGGCCCTTCCCGAGGGGGAGA

-60               -40                -20
GGGAGGCGTTTCTAAAAGCCCTTCAGGACGCTACCCGGGGCGGGTGGTGGAAGGGTAAC 1                 20                 40                 60
ATGAGGGGGATGCTGCCCCTCTTTGAGCCCAAGGGCCGGGTCCTCCTGGTGGACGGCCAC
MetArgGlyMetLeuProLeuPheGluProLysGlyArgValLeuLeuValAspGlyHis
  1

80                100                120
CACCTGGCCTACCGCACCTTCCACGCCCTGAAGGGCCTCACCACCAGCCGGGGGGAGCCG
HisLeuAlaTyrArgThrPheHisAlaLeuLysGlyLeuThrThrSerArgGlyGluPro 140                160                180
GTGCAGGCGGTCTACGGCTTCGCCAAGAGCCTCCTCAAGGCCCTCAAGGAGGACGGGGAC
ValGlnAlaValTyrGlyPheAlaLysSerLeuLeuLysAlaLeuLysGluAspGlyAsp
 41

200                220                240
GCGGTGATCGTGGTCTTTGACGCCAAGGCCCCCTCCTTCCGCCACGAGGCCTACGGGGGG
AlaValIleValValPheAspAlaLysAlaProSerPheArgHisGluAlaTyrGlyGly 260                280                300
TACAAGGCGGGCCGGGCCCCCACGCCGGAGGACTTTCCCCGGCAACTCGCCCTCATCAAG
TyrLysAlaGlyArgAlaProThrProGluAspPheProArgGlnLeuAlaLeuIleLys
 81

320                340                360
                                    XhoI
GAGCTGGTGGACCTCCTGGGGCTGGCGCGCCTCGAGGTCCCGGGCTACGAGGCGGACGAC
GluLeuValAspLeuLeuGlyLeuAlaArgLeuGluValProGlyTyrGluAlaAspAsp
```

TAQ DNA POLYMERASE SEQUENCE

FIG.1-2

```
              380                       400                       420
               .                         .                         .
GTCCTGGCCAGCCTGGCCAAGAAGGCGGAAAAGGAGGGCTACGAGGTCCGCATCCTCACC
ValLeuAlaSerLeuAlaLysLysAlaGluLysGluGlyTyrGluValArgIleLeuThr
121

440                       460                       480
               .                         .                         .
GCCGACAAAGACCTTTACCAGCTCCTTTCCGACCGCATCCACGTCCTCCACCCCGAGGGG
AlaAspLysAspLeuTyrGlnLeuLeuSerAspArgIleHisValLeuHisProGluGly 500                       520                       540
Asp718         .                         .                         .
  TACCTCATCACCCCGGCCTGGCTTTGGGAAAAGTACGGCCTGAGGCCCGACCAGTGGGCC
  TyrLeuIleThrProAlaTrpLeuTrpGluLysTyrGlyLeuArgProAspGlnTrpAla
  161

560                       580                       600
               .                         .                         .
GACTACCGGGCCCTGACCGGGGACGAGTCCGACAACCTTCCCGGGGTCAAGGGCATCGGG
AspTyrArgAlaLeuThrGlyAspGluSerAspAsnLeuProGlyValLysGlyIleGly 620                       640                       660
        HindIII .                         .                         .
GAGAAGACGGCGAGGAAGCTTCTGGAGGAGTGGGGGAGCCTGGAAGCCCTCCTCAAGAAC
GluLysThrAlaArgLysLeuLeuGluGluTrpGlySerLeuGluAlaLeuLeuLysAsn
201

680                       700                       720
               .                         .                         .
CTGGACCGGCTGAAGCCCGCCATCCGGGAGAAGATCCTGGCCCACATGGACGATCTGAAG
LeuAspArgLeuLysProAlaIleArgGluLysIleLeuAlaHisMetAspAspLeuLys 740                       760                       780
               .                         .                         .
CTCTCCTGGGACCTGGCCAAGGTGCGCACCGACCTGCCCCTGGAGGTGGACTTCGCCAAA
LeuSerTrpAspLeuAlaLysValArgThrAspLeuProLeuGluValAspPheAlaLys
241

800                       820                       840
               .                         .                         .
AGGCGGGAGCCCGACCGGGAGAGGCTTAGGGCCTTTCTGGAGAGGCTTGAGTTTGGCAGC
ArgArgGluProAspArgGluArgLeuArgAlaPheLeuGluArgLeuGluPheGlySer
```

TAQ DNA POLYMERASE SEQUENCE

FIG.1-3

```
          860                     880                    900
                                 BstXI
CTCCTCCACGAGTTCGGCCTTCTGGAAAGCCCCAAGGCCCTGGAGGAGGCCCCCTGGCCC
LeuLeuHisGluPheGlyLeuLeuGluSerProLysAlaLeuGluGluAlaProTrpPro
281                              290

920                     940                    960
CCGCCGGAAGGGGCCTTCGTGGGCTTTGTGCTTTCCCGCAAGGAGCCCATGTGGGCCGAT
ProProGluGlyAlaPheValGlyPheValLeuSerArgLysGluProMetTrpAlaAsp 980                    1000                   1020
CTTCTGGCCCTGGCCGCCGCCAGGGGGGGCCGGGTCCACCGGGCCCCCGAGCCTTATAAA
LeuLeuAlaLeuAlaAlaAlaArgGlyGlyArgValHisArgAlaProGluProTyrLys
321

1040                    1060                   1080
GCCCTCAGGGACCTGAAGGAGGCGCGGGGGCTTCTCGCCAAAGACCTGAGCGTTCTGGCC
AlaLeuArgAspLeuLysGluAlaArgGlyLeuLeuAlaLysAspLeuSerValLeuAla 1100                    1120                   1140
CTGAGGGAAGGCCTTGGCCTCCCGCCCGGCGACGACCCCATGCTCCTCGCCTACCTCCTG
LeuArgGluGlyLeuGlyLeuProProGlyAspAspProMetLeuLeuAlaTyrLeuLeu
361

1160                    1180                   1200
GACCCTTCCAACACCACCCCCGAGGGGGTGGCCCGGCGCTACGGCGGGGAGTGGACGGAG
AspProSerAsnThrThrProGluGlyValAlaArgArgTyrGlyGlyGluTrpThrGlu 1220                    1240                   1260
GAGGCGGGGGAGCGGGCCGCCCTTTCCGAGAGGCTCTTCGCCAACCTGTGGGGGAGGCTT
GluAlaGlyGluArgAlaAlaLeuSerGluArgLeuPheAlaAsnLeuTrpGlyArgLeu
401

1280                    1300                   1320
GAGGGGGAGGAGAGGCTCCTTTGGCTTTACCGGGAGGTGGAGAGGCCCCTTTCCGCTGTC
GluGlyGluGluArgLeuLeuTrpLeuTyrArgGluValGluArgProLeuSerAlaVal
```

TAQ DNA POLYMERASE SEQUENCE

FIG.1-4

```
            1340                  1360                  1380
             .                     .                     .
CTGGCCCACATGGAGGCCACGGGGGTGCGCCTGGACGTGGCCTATCTCAGGGCCTTGTCC
LeuAlaHisMetGluAlaThrGlyValArgLeuAspValAlaTyrLeuArgAlaLeuSer
441

1400                  1420                  1440
                                  XhoI
             .                     .                     .
CTGGAGGTGGCCGAGGAGATCGCCCGCCTCGAGGCCGAGGTCTTCCGCCTGGCCGGCCAC
LeuGluValAlaGluGluIleAlaArgLeuGluAlaGluValPheArgLeuAlaGlyHis 1460                  1480                  1500
                                  PvuII
             .                     .                     .
CCCTTCAACCTCAACTCCCGGGACCAGCTGGAAAGGGTCCTCTTTGACGAGCTAGGGCTT
ProPheAsnLeuAsnSerArgAspGlnLeuGluArgValLeuPheAspGluLeuGlyLeu
481

1520                  1540                  1560
             .                     .                     .
CCCGCCATCGGCAAGACGGAGAAGACCGGCAAGCGCTCCACCAGCGCCGCCGTCCTGGAG
ProAlaIleGlyLysThrGluLysThrGlyLysArgSerThrSerAlaAlaValLeuGlu 1580                  1600                  1620
                                  PstI         SacI
             .                     .                     .
GCCCTCCGCGAGGCCCACCCCATCGTGGAGAAGATCCTGCAGTACCGGGAGCTCACCAAG
AlaLeuArgGluAlaHisProIleValGluLysIleLeuGlnTyrArgGluLeuThrLys
521

1640                  1660                  1680
             .                     .                     .
CTGAAGAGCACCTACATTGACCCCTTGCCGGACCTCATCCACCCCAGGACGGGCCGCCTC
LeuLysSerThrTyrIleAspProLeuProAspLeuIleHisProArgThrGlyArgLeu 1700                  1720                  1740
             .                     .                     .
CACACCCGCTTCAACCAGACGGCCACGGCCACGGGCAGGCTAAGTAGCTCCGATCCCAAC
HisThrArgPheAsnGlnThrAlaThrAlaThrGlyArgLeuSerSerSerAspProAsn
561

1760                  1780                  1800
                                  BamHI
             .                     .                     .
CTCCAGAACATCCCCGTCCGCACCCCGCTTGGGCAGAGGATCCGCCGGGCCTTCATCGCC
LeuGlnAsnIleProValArgThrProLeuGlyGlnArgIleArgArgAlaPheIleAla
```

TAQ DNA POLYMERASE SEQUENCE  FIG.1-5

```
               1820                  1840                  1860
                                      SacI
       .          .          .          .          .          .
GAGGAGGGGTGGCTATTGGTGGCCCTGGACTATAGCCAGATAGAGCTCAGGGTGCTGGCC
GluGluGlyTrpLeuLeuValAlaLeuAspTyrSerGlnIleGluLeuArgValLeuAla
601

1880                  1900                  1920
       .          .          .          .          .          .
CACCTCTCCGGCGACGAGAACCTGATCCGGGTCTTCCAGGAGGGGCGGGACATCCACACG
HisLeuSerGlyAspGluAsnLeuIleArgValPheGlnGluGlyArgAspIleHisThr 1940                  1960                  1980
  PvuII
       .          .          .          .          .          .
GAGACCGCCAGCTGGATGTTCGGCGTCCCCCGGGAGGCCGTGGACCCCCTGATGCGCCGG
GluThrAlaSerTrpMetPheGlyValProArgGluAlaValAspProLeuMetArgArg
641

2000                  2020                  2040
       .          .          .          .          .          .
GCGGCCAAGACCATCAACTTCGGGGTCCTCTACGGCATGTCGGCCCACCGCCTCTCCCAG
AlaAlaLysThrIleAsnPheGlyValLeuTyrGlyMetSerAlaHisArgLeuSerGln 2060                  2080                  2100
  NheI
       .          .          .          .          .          .
GAGCTAGCCATCCCTTACGAGGAGGCCCAGGCCTTCATTGAGCGCTACTTTCAGAGCTTC
GluLeuAlaIleProTyrGluGluAlaGlnAlaPheIleGluArgTyrPheGlnSerPhe
681

2120                  2140                  2160
       .          .          .          .          .          .
CCCAAGGTGCGGGCCTGGATTGAGAAGACCCTGGAGGAGGGCAGGAGGCGGGGGTACGTG
ProLysValArgAlaTrpIleGluLysThrLeuGluGluGlyArgArgArgGlyTyrVal 2180                  2200                  2220
       .          .          .          .          .          .
GAGACCCTCTTCGGCCGCCGCCGCTACGTGCCAGACCTAGAGGCCCGGGTGAAGAGCGTG
GluThrLeuPheGlyArgArgArgTyrValProAspLeuGluAlaArgValLysSerVal
721
```

TAQ DNA POLYMERASE SEQUENCE

```
              2240                2260                2280
                 .                   .                   .
CGGGAGGCGGCCGAGCGCATGGCCTTCAACATGCCCGTCCAGGGCACCGCCGCCGACCTC
ArgGluAlaAlaGluArgMetAlaPheAsnMetProValGlnGlyThrAlaAlaAspLeu
741

2300                2320                2340
                 .                   .                   .
ATGAAGCTGGCTATGGTGAAGCTCTTCCCCAGGCTGGAGGAAATGGGGGCCAGGATGCTC
MetLysLeuAlaMetValLysLeuPheProArgLeuGluGluMetGlyAlaArgMetLeu 2360                2380                2400
                        XhoI         .                   .
CTTCAGGTCCACGACGAGCTGGTCCTCGAGGCCCCAAAAGAGAGGGCGGAGGCCGTGGCC
LeuGlnValHisAspGluLeuValLeuGluAlaProLysGluArgAlaGluAlaValAla
781

2420                2440                2460
                 .                   .                   .
CGGCTGGCCAAGGAGGTCATGGAGGGGGTGTATCCCCTGGCCGTGCCCCTGGAGGTGGAG
ArgLeuAlaLysGluValMetGluGlyValTyrProLeuAlaValProLeuGluValGlu 2480                2500
                 .                   .
GTGGGGATAGGGGAGGACTGGCTCTCCGCCAAGGAGTGATACCACC
ValGlyIleGlyGluAspTrpLeuSerAlaLysGluEnd
821                                     832
```

FIG.1-6

STABILIZED THERMOSTABLE NUCLEIC ACID POLYMERASE COMPOSITIONS CONTAINING NON-IONIC POLYMERIC DETERGENTS

CROSS-REFERENCE TO RELATED APPLICATIONS

This application is a continuation of application Ser. No. 07/387,003, filed Jul. 28, 1989, now abandoned, which is a division of application Ser. No. 07/143,441, filed Jan. 12, 1988, now abandoned, which is a continuation-in-part of application Ser. No. 07/063,509, filed Jun. 17, 1987, now U.S. Pat. No. 4,889,818, which is a continuation-in-part of application Ser. No. 06/899,241, filed Aug. 22, 1986, now abandoned.

FIELD OF THE INVENTION

The present invention relates to stabilized thermostable enzyme compositions. In one embodiment the enzyme is DNA polymerase purified from *Thermus aquaticus* and has a molecular weight of about 86,000–95,000. In another embodiment the enzyme is DNA polymerase produced by recombinant means.

BACKGROUND ART

Extensive research has been conducted on the isolation of DNA polymerases from mesophilic microorganisms such as *E. coli*. See, for example, Bessman et al., *J. Biol. Chem.* (1957) 233:171–177 and Buttin and Kornberg (1966) *J. Biol. Chem.* 241:5419–5427.

In contrast, relatively little investigation has been made on the isolation and purification of DNA polymerases from thermophiles, such as *Thermus aquaticus*. Kaledin et al., *Biokhymiya* (1980) 45:644–651 discloses a six-step isolation and purification procedure of DNA polymerase from cells of *T. aquaticus* YT1 strain. These steps involve isolation of crude extract, DEAE-cellulose chromatography, fractionation on hydroxyapatite, fractionation on DEAE-cellulose, and chromatography on single-stranded DNA-cellulose. The pools from each stage were not screened for contaminating endo- and exonuclease(s). The molecular weight of the purified enzyme is reported as 62,000 daltons per monomeric unit.

A second purification scheme for a polymerase from *T. aquaticus* is described by A. Chien et al., *J. Bacteriol.* (1976) 127:1550–1557. In this process, the crude extract is applied to a DEAE-Sephadex column. The dialyzed pooled fractions are then subjected to treatment on a phosphocellulose column. The pooled fractions are dialyzed and bovine serum albumin (BSA) is added to prevent loss of polymerase activity. The resulting mixture is loaded on a DNA-cellulose column. The pooled material from the column is dialyzed and analyzed by gel filtration to have a molecular weight of about 63,000 daltons, and, by sucrose gradient centrifugation of about 68,000 daltons.

The use of a thermostable enzyme to amplify existing nucleic acid sequences in amounts that are large compared to the amount initially present has been suggested in U.S. Pat. No. 4,683,195. Primers, nucleotide triphosphates, and a polymerase are used in the process, which involves denaturation, synthesis of template strands and hybridization. The extension produce of each primer becomes a template for the production of the desired nucleic acid sequence. The patent disclosed that if the polymerase employed is a thermostable enzyme, it need not be added after every denaturation step, because the heat will not destroy its activity. No other advantages or details are provided on the use of a purified thermostable DNA polymerase. Furthermore, New England Biolabs had marketed a polymerase from *T. aquaticus,* but was unaware that the polymerase activity decreased substantially with time in a storage buffer not containing non-ionic detergents.

Accordingly, there is a desire in the art to produce a purified, stable thermostable enzyme that may be used to improve the nucleic acid amplification process described above.

SUMMARY OF THE INVENTION

Accordingly, the present invention provides a purified thermostable enzyme that catalyzes combination of nucleotide triphosphates to form a nucleic acid strand complementary to a nucleic acid template strand. Preferably the purified enzyme is DNA polymerase from *Thermus aquaticus* and has a molecular weight of about 86,000–95,000 daltons. This purified material may be used in a temperature-cycling amplification reaction wherein nucleic acid sequences are produced from a given nucleic acid sequence in amounts that are large compared to the amount initially present so that they can be manipulated and/or analyzed easily.

The gene encoding the DNA polymerase enzyme from *Thermus aquaticus* has also been identified and cloned and provides yet another means to prepare the thermostable enzyme of the present invention. In addition to the gene encoding the approximately 86,000–95,000 dalton enzyme, gene derivatives encoding DNA polymerase activity are also presented.

The invention also encompasses a stable enzyme composition comprising a purified, thermostable enzyme as described above in a buffer containing one or more non-ionic polymeric detergents.

Finally, the invention provides a method of purification for the thermostable polymerase of the invention which comprises treating an aqueous mixture containing the thermostable polymerase with a hydrophobic interaction chromatographic support under conditions which promote hydrophobic interactions and eluting the bound thermostable polymerase from said support with a solvent which attenuates hydrophobic interactions.

The purified enzyme, as well as the enzymes produced by recombinant DNA techniques, provides much more specificity than the Klenow fragment, which is not thermostable, when used in the temperature-cycling amplification reaction. In addition, the purified enzyme and the recombinantly produced enzymes exhibit the appropriate activity expected when TTP or other nucleotide triphosphates are not present in the incubation mixture with the DNA template. Also, the enzymes herein have a broader pH profile than that of the thermostable enzyme from *Thermus aquaticus* described in the literature, with more than 50% of the activity at pH 6.4 as at pH 8.

BRIEF DESCRIPTION OF THE DRAWINGS

FIG. 1 is the DNA sequence and the predicted amino acid sequence for Taq polymerase. The amino acid sequence corresponding to the deduced primary translation product is numbered 1–832.

DESCRIPTION OF THE PREFERRED EMBODIMENTS

Figure 2:
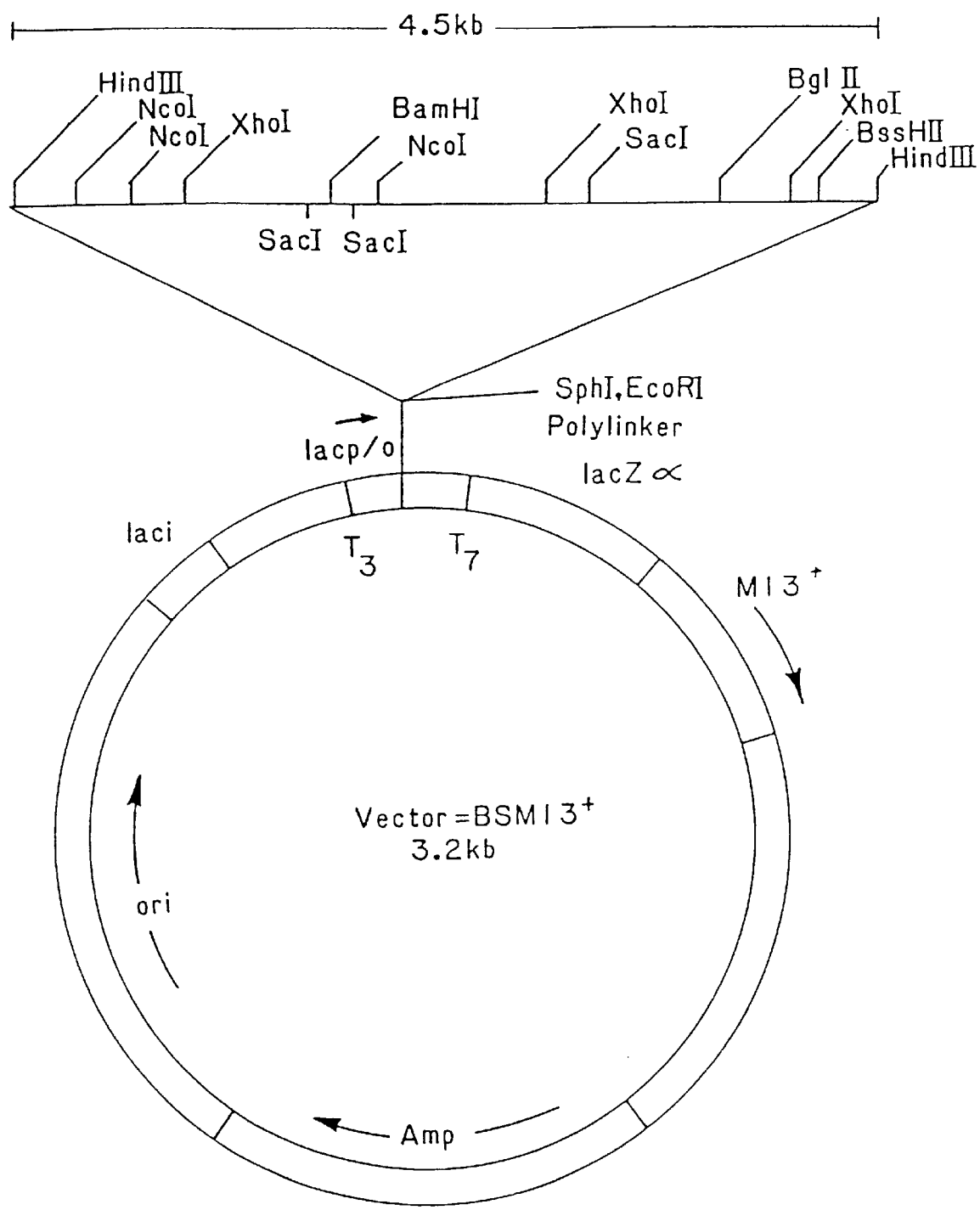
FIG. 2 is a restriction site map of plasmid pFC83 that contains the ~4.5 kb HindIII *T. aquaticus* DNA insert subcloned into plasmid BSM13+.
Figure 3:
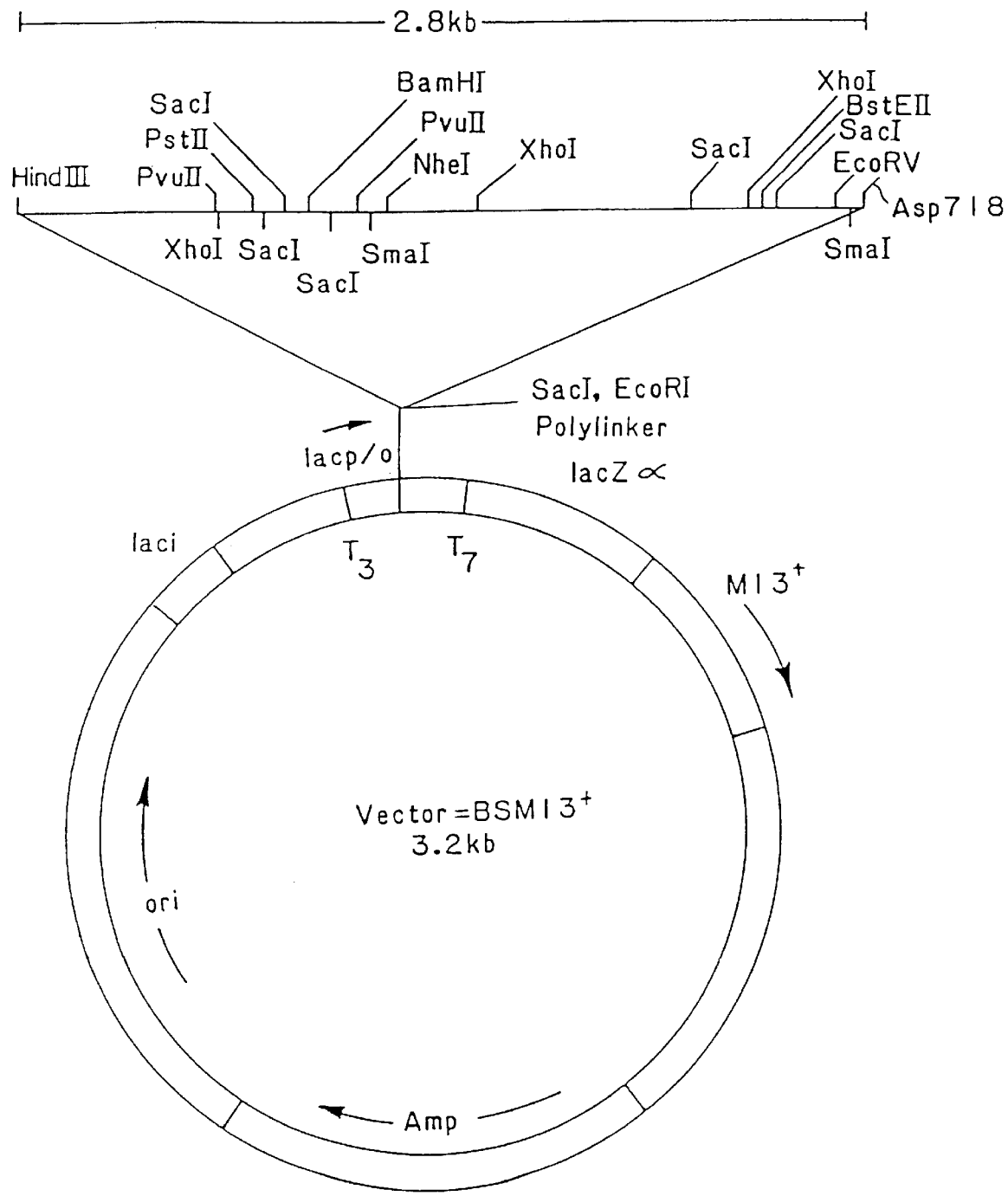
FIG. 3 is a restriction site map of plasmid pFC85 that contains the ~2.68 kb HindIII to Asp718 *T. aquaticus* DNA insert subcloned into plasmid BSM13+.

As used herein, "cell", "cell line", and "cell culture" can be used interchangeably and all such designations include progeny. Thus, the words "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included.

The term "control sequences" refers to DNA sequences necessary for the expression of an operably linked coding sequence in a particular host organism. The control sequences that are suitable for procaryotes, for example, include a promoter, optionally an operator sequence, a ribosome binding site, and possibly, other as yet poorly understood sequences. Eucaryotic cells are known to utilize promoters, polyadenylation signals, and enhancers.

The term "expression system" refers to DNA sequences containing a desired coding sequence and control sequences in operable linkage, so that hosts transformed with these sequences are capable of producing the encoded proteins. In order to effect transformation, the expression system may be included on a vector; however, the relevant DNA may than also be integrated into the host chromosome.

The term "gene" as used herein refers to a DNA sequence that encodes a recoverable bioactive polypeptide or precursor. The polypeptide can be encoded by a full-length gene sequence or any portion of the coding sequence so long as the enzymatic activity is retained.

In one embodiment of the invention, the DNA sequence encoding a full-length thermostable DNA polymerase of *Thermus aquaticus* (Taq) is provided. FIG. 1 shows this DNA sequence and the deduced amino acid sequence. For convenience, the amino acid sequence of this Taq polymerase will be used as a reference and other forms of the thermostable enzyme will be designated by referring to the sequence shown in FIG. 1. Since the N-terminal methionine may or may not be present, both forms are included in all cases wherein the thermostable enzyme is produced in bacteria.

"Operably linked" refers to juxtaposition such that the normal function of the components can be performed. Thus, a coding sequence "operably linked" to control sequences refers to a configuration wherein the coding sequences can be expressed under the control of the control sequences.

The term "mixture" as it relates to mixtures containing Taq polymerase refers to a collection of materials which includes Taq polymerase but which also includes alternative proteins. If the Taq polymerase is derived from recombinant host cells, the other proteins will ordinarily be those associated with the host. Where the host is bacterial, the contaminating proteins will, of course, be bacterial proteins.

"Non-ionic polymeric detergents" refers to a surface-active agents that have no ionic charge and that are characterized, for purposes of this invention, by their ability to stabilize the enzyme herein at a pH range of from about 3.5 to about 9.5, preferably from 4 to 8.5.

The term "oligonucleotide" as used herein is defined as a molecule comprised of two or more deoxyribonucleotides or ribonucleotides, preferably more than three. Its exact size will depend on many factors, which in turn depend on the ultimate function or use of the oligonucleotide. The oligonucleotide may be derived synthetically or by cloning.

The term "primer" as used herein refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is initiated, i.e., in the presence of four different nucleotide triphosphates and thermostable enzyme in an appropriate buffer ("buffer" includes pH, ionic strength, cofactors, etc.) and at a suitable temperature. For Taq polymerase the buffer herein preferably contains 1.5–2 mM of a magnesium salt, preferably $MgCl_2$, 150–200 $\mu$M of each nucleotide, and 1 $\mu$M of each primer, along with preferably 50 mM KCl, 10 mM Tris buffer, pH 8–8.4, and 100 $\mu$g/ml gelatin.

The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the thermostable enzyme. The exact lengths of the primers will depend on many factors, including temperature, source of primer and use of the method. For example, depending on the complexity of the target sequence, the oligonucleotide primer typically contains 15–25 nucleotides, although it may contain more or fewer nucleotides. Short primer molecules generally require cooler temperatures to form sufficiently stable hybrid complexes with template.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to be amplified to hybridize therewith and thereby form a template for synthesis of the extension product of the other primer. However, for detection purposes, particularly using labeled sequence-specific probes, the primers typically have exact complementarity to obtain the best results.

As used herein, the terms "restriction endonucleases" and "restriction enzymes" refer to bacterial enzymes each of which cut double-stranded DNA at or near a specific nucleotide sequence.

As used herein, the term "thermostable enzyme" refers to an enzyme which is stable to heat and is heat resistant and catalyzes (facilitates) combination of the nucleotides in the proper manner to form the primer extension products that are complementary to each nucleic acid strand. Generally, the synthesis will be initiated at the 3' end of each primer and will proceed in the 5' direction along the template strand, until synthesis terminates, producing molecules of different lengths. There may be a thermostable enzyme, however, which initiates synthesis at the 5' end and proceeds in the other direction, using the same process as described above.

The thermostable enzyme herein must satisfy a single criterion to be effective for the amplification reaction, i.e., the enzyme must not become irreversible denatured (inactivated) when subjected to the elevated temperatures for the time necessary to effect denaturation of double-stranded nucleic acids. Irreversible denaturation for purposes herein refers to permanent and complete loss of enzymatic activity. The heating conditions necessary for nucleic acid denaturation will depend, e.g., on the buffer salt concentration and composition and the length and nucleotide composition of the nucleic acids being denatured, but typically range from about 90 to about 105° C. for a time depending mainly on the temperature and the nucleic acid length, typically about 0.5 to four minutes. Higher temperatures may be tolerated as the buffer salt concentration and/or GC composition of the nucleic acid is increased. Preferably, the enzyme will not become irreversible denatured at about 90–100° C.

The thermostable enzyme herein preferably has an optimum temperature at which it functions that is higher than about 40° C., which is the temperature below which hybridization of primer to template is promoted, although, depending on (1) salt concentration and composition and (2) composition and length of primer, hybridization can occur at higher temperature (e.g., 45–70° C.). The higher the temperature optimum for the enzyme, the greater the specificity and/or selectivity of the primer-directed extension process. However, enzymes that are active below 40° C., e.g., at 37° C., are also within the scope of this invention provided they are heat-stable. Preferably, the optimum temperature ranges from about 50 to 90° C., more preferably 60–80° C.

The thermostable enzyme herein may be obtained from any source and may be a native or recombinant protein. Examples of enzymes that have been reported in the literature as being resistant to heat include heat-stable polymerases, such as, e.g., polymerases extracted from the thermophilic bacteria *Thermus flavus, Thermus ruber, Thermus thermophilus, Bacillus stearothermophilus* (which has a somewhat lower temperature optimum than the others listed), *Thermus aquaticus, Thermus lacteus, Thermus rubens,* and *Methanothermus fervidus.* In addition, thermostable polymerases isolated from the thermophilic archaebacteria include, for example, *Sulfolobus solfataricus, Sulfolobus acidocaldarius, Thermoplasma acidophilum, Methanobacterium thermoautotrophicum* and *Desulfurococcus mobilis.*

The thermostable enzyme of the invention has the amino acid sequence presented in FIG. 1. In addition, any thermostable polymerase containing at least 50% homology to any contiguous stretch of nine or more amino acids presented therein is also intended to be within the scope of the invention. This homology can be determined using commercially available data banks such as the European Molecular Biology Laboratory (EMBL) or Genbank. Moreover, as new thermostable polymerases are identified, specific regions of homology between the newly identified sequences and the Taq polymerase sequence may be determined using, for example, the Sequence Analysis Software Package of the Genetics Computer Group of the University of Wisconsin. Specific regions of homology include the following sequences (numbered according to the numbering of amino acids in FIG. 1): residues 190–204, 262–270, 569–587, 718–732, 743–759, and 778–790.

The preferred thermostable enzyme herein is a DNA polymerase isolated from *Thermus aquaticus.* Various strains thereof are available from the American Type Culture Collection, Rockville, Md., and is described by T. D. Brock, *J. Bact.* (1969) 98:289–297, and by T. Oshima, *Arch. Microbiol.* (1978): 189–196. One of these preferred strains is strain YT-1.

For recovering the native protein the cells are grown using any suitable technique. One such technique is described by Kaledin et al., *Biokhimiya* (1980), supra, the disclosure of which is incorporated herein by reference. Briefly, the cells are grown on a medium, in one liter, of nitrilotriacetic acid (100 mg), tryptone (3 g), yeast extract (3 g), succinic acid (5 g), sodium sulfite (50 mg), riboflavin (1 mg), $K_2HPO_4$ (522 mg), $MgSO_4$ (480 mg), $CaCl_2$ (222 mg), NaCl (20 mg), and trace elements. The pH of the medium is adjusted to 8.0±0.2 with KOH. The yield is increased up to 20 grams of cells/liter if cultivated with vigorous aeration at a temperature of 70° C. Cells in the late logarithmic growth stage (determined by absorbance at 550 nm) are collected by centrifugation, washed with a buffer and stored frozen at −20° C.

In another method for growing the cells, described in Chien et al., *J. Bacteriol.* (1976), supra, the disclosure of which is incorporated herein by reference, a defined mineral salts medium containing 0.3% glutamic acid supplemented with 0.1 mg/l biotin, 0.1 mg/l thiamine, and 0.05 mg/l nicotinic acid is employed. The salts include nitrilotriacetic acid, $CaSO_4$, $MgSO_4$, NaCl, $KNO_3$, $NaNO_3$, $ZnSO_4$, $H_3BO_3$, $CuSO_4$, $NaMoO_4$, $CoCl_2$, $FeCl_3$, $MnSO_4$, and $Na_2HPO_4$. The pH of the medium is adjusted to 8.0 with NaOH.

In the Chien et al. technique, the cells are grown initially at 75° C. in a water bath shaker. On reaching a certain density, 1 liter of these cells is transferred to 16-liter carboys which are placed in hot-air incubators. Sterile air is bubbled through the cultures and the temperatures maintained at 75° C. The cells are allowed to grow for 20 hours before being collected by centrifuge.

After cell growth, the isolation and purification of the enzyme take place in six stages, each of which is carried out at a temperature below room temperature, preferably about 4° C.

In the first stage or step, the cells, if frozen, are thawed, disintegrated by ultrasound, suspended in a buffer at about pH 7.5, and centrifuged.

In the second stage, the supernatant is collected and then fractionated by adding a salt such as dry ammonium sulfate. The appropriate fraction (typically 45–75% of saturation) is collected, dissolved in a 0.2 M potassium phosphate buffer preferably at pH 6.5, and dialyzed against the same buffer.

The third step removes nucleic acids and some protein. The fraction from the second stage is applied to a DEAE-cellulose column equilibrated with the same buffer as used above. Then the column is washed with the same buffer and the flow-through protein-containing fractions, determined by absorbance at 280 nm, are collected and dialyzed against a 10 mM potassium phosphate buffer, preferably with the same ingredients as the first buffer, but at a pH of 7.5.

In the fourth step, the fraction so collected is applied to a hydroxyapatite column equilibrated with the buffer used for dialysis in the third step. The column is then washed and the enzyme eluted with a linear gradient of a buffer such as 0.01 M to 0.5 M potassium phosphate buffer at pH 7.5 containing 10 mM 2-mercaptoethanol and 5% glycerine. The pooled fractions containing thermostable enzyme (e.g., DNA polymerase) activity are dialyzed against the same buffer used for dialysis in the third step.

In the fifth stage, the dialyzed fraction is applied to a DEAE-cellulose column, equilibrated with the buffer used for dialysis in the third step. The column is then washed and the enzyme eluted with a linear gradient of a buffer such as 0.01 to 0.6 M KCl in the buffer used for dialysis in the third step. Fractions with thermostable enzyme activity are then tested for contaminating deoxyribonucleases (endo- and exonucleases) using any suitable procedure. For example, the endonuclease activity may be determined electrophoretically from the change in molecular weight of phage λ DNA or supercoiled plasmid DNA after incubation with an excess of DNA polymerase. Similarly, exonuclease activity may be determined electrophoretically from the change in molecular weight of DNA after treatment with a restriction enzyme that cleaves at several sites.

The fractions determined to have no deoxyribonuclease activity are pooled and dialyzed against the same buffer used in the third step.

In the sixth step, the pooled fraction are placed on a phosphocellulose column with a set bed volume. The column is washed and the enzyme eluted with a linear gradient of a buffer such as 0.01 to 0.4 KCl in a potassium phosphate buffer at pH 7.5. The pooled fractions having thermostable polymerase activity and no deoxyribonuclease activity are dialyzed against a buffer at pH 8.0.

The molecular weight of the dialyzed product may be determined by any technique, for example, by SDS-PAGE analysis using protein molecular weight markers. The molecular weight of one of the preferred enzymes herein, the DNA polymerase purified from *Thermus aquaticus,* is determined by the above method to be about 86,000–90,000 daltons. The molecular weight of this same DNA polymerase as determined by the predicted amino acid sequence is calculated to be approximately 94,000 daltons. Thus, the molecular weight of the full length DNA polymerase is dependent upon the method employed to determine this number and falls within the range of 86,000–95,000 daltons.

The thermostable enzyme of this invention may also be produced by recombinant DNA techniques, as the gene encoding this enzyme has been cloned from *Thermus aquaticus* genomic DNA. The complete coding sequence for the *Thermus aquaticus* (Taq) polymerase can be derived from bacteriophage CH35:Taq#4-2 on an approximately 3.5 kilobase (kb) BglII-Asp718 (partial) restriction fragment contained within an ~18 kb genomic DNA insert fragment. This bacteriophage was deposited with the American Type Culture Collection (ATCC) on May 29, 1987 and has accession no. 40,336. Alternatively, the gene can be constructed by ligating an ~730 base pair (bp) BglII-HindIII restriction fragment isolated from plasmid pFC83 (ATCC 67,422 deposited May 29, 1987) to an ~2.68 kg HindIII-Asp718 restriction fragment isolated from plasmid pFC85 (ATCC 67,421 deposited May 29, 1987). The pFC83 restriction fragment comprises the amino-terminus of the Taq polymerase gene while the restriction fragment from pFC85 comprises the carboxy-terminus. Thus, ligation of these two fragments into a correspondingly digested vector with appropriate control sequences will result in the translation of a full-length Taq polymerase.

As stated previously, the DNA and deduced amino acid sequence of a preferred thermostable enzyme is provided in FIG. 1. In addition to the N-terminal deletion described supra, it has also been found that the entire coding sequence of the Taq polymerase gene is not required to recover a biologically active gene product with DNA polymerase activity. Amino-terminal deletions wherein approximately one-third of the coding sequence is absent has resulted in producing a gene product that is quite active in polymerase assays.

In addition to the N-terminal deletions, individual amino acid residues in the peptide chain comprising Taq polymerase may be modified by oxidation, reduction, or other derivatization, and the protein may be cleaved to obtain fragments that retain activity. Such alterations that do not destroy activity do not remove the protein from the definition, and are specifically included.

Thus, modifications to the primary structure itself by deletion, addition, or alteration of the amino acids incorporated into the sequence during translation can be made without destroying the high temperature DNA polymerase activity of the protein. Such substitutions or other alterations result in proteins having an amino acid sequence encoded by DNA falling within the contemplated scope of the present invention.

Polyclonal antiserum from rabbits immunized with the purified 86,000–95,000 dalton polymerase of this invention was used to probe a *Thermus aquaticus* partial genomic expression library to obtain the appropriate coding sequence as described below. The cloned genomic sequence can be expressed as a fusion polypeptide, expressed directly using its own control sequences, or expressed by constructions using control sequences appropriate to the particular host used for expression of the enzyme.

Of course, the availability of DNA encoding these sequences provides the opportunity to modify the codon sequence so as to generate mutein (mutant protein) forms also having DNA polymerase activity.

Thus, these tools can provide the complete coding sequence for Taq DNA polymerase from which expression vectors applicable to a variety of host systems can be constructed and the coding sequence expressed. Portions of the Taq polymerase-encoding sequence are useful as probes to retrieve other thermostable polymerase-encoding sequences in a variety of species. Accordingly, portions of the genomic DNA encoding at least four to six amino acids can be replicated in *E. coli* and the denatured forms used as probes or oligodeoxyribonucleotide probes can be synthesized which encode at leas four to six amino acids and used to retrieve additional DNAs encoding a thermostable polymerase. Because there may not be a precisely exact match between the nucleotide sequence in the *Thermus aquaticus* form and that in the corresponding portion of other species, oligomers containing approximately 12–18 nucleotides (encoding the four to six amino acid stretch) are probably necessary to obtain hybridization under conditions of sufficient stringency to eliminate false positives. The sequences encoding six amino acids would supply information sufficient for such probes.

Suitable Hosts, Control Systems and Methods

In general terms, the production of a recombinant form of Taq polymerase typically involves the following:

First, a DNA is obtained that encodes the mature (used here to include all muteins) enzyme or a fusion of the Taq polymerase to an additional sequence that does not destroy its activity or to an additional sequence cleavable under controlled conditions (such as treatment with peptidase) to give an active protein. If the sequence is uninterrupted by introns it is suitable for expression in any host. This sequence should be in an excisable and recoverable form.

The excised or recovered coding sequence is then preferably placed in operable linkage with suitable control sequences in a replicable expression vector. The vector is used to transform a suitable host and the transformed host cultured under favorable conditions to effect the production of the recombinant Taq polymerase. Optionally the Taq polymerase is isolated from the medium or from the cells; recovery and purification of the protein may not be necessary in some instances, where some impurities may be tolerated.

Each of the foregoing steps can be done in a variety of ways. For example, the desired coding sequences may be obtained from genomic fragments and used directly in appropriate hosts. The constructions for expression vectors operable in a variety of hosts are made using appropriate replicons and control sequences, as set forth below. Suitable restriction sites can, if not normally available, be added to the ends of the coding sequence, so as to provide an excisable gene to insert into these vectors.

The control sequences, expression vectors, and transformation methods are dependent on the type of host cell used to express the gene. Generally, procaryotic, yeast, insect or mammalian cells are presently useful as hosts. Procaryotic hosts are in general the most efficient and convenient for the production of recombinant proteins and therefore preferred for the expression of Taq polymerase.

In the particular case of Taq polymerase, evidence indicates that considerable deletion at the N-terminus of the protein may occur under both recombinant and native conditions, and that the DNA polymerase activity of the protein is still retained. It appears that the native proteins previously isolated may be the result of proteolytic degradation, and not translation of a truncated gene. The mutein produced from the truncated gene of plasmid pFC85 is, however, fully active in assays for DNA polymerase, as is that produced from DNA encoding the full-length sequence. Since it is clear that certain N-terminal shortened forms of the polymerase are active, the gene constructs used for expression of these polymerases may also include the corresponding shortened forms of the coding sequence.

Control Sequences and Corresponding Hosts

Procaryotes most frequently are represented by various strains of *E. coli*. However, other microbial strains may also be used, such as *bacilli*, for example, *Bacillus subtilis*, various species of Pseudomonas, or other bacterial strains. In such procaryotic systems, plasmid vectors that contain replication sites and control sequences derived from a species compatible with the host are used. For example, *E. coli* is typically transformed using derivatives of pBR322, a plasmid derived from an *E. coli* species by Bolivar, et al., *Gene* (1977) 2:95. pBR322 contains genes for ampicillin and tetracycline resistance, and thus provides additional markers that can be either retained or destroyed in constructing the desired vector. Commonly used procaryotic control sequences, which are defined herein to include promoters for transcription initiation, optionally with an operator, along with ribosome binding site sequences, include such commonly used promoters as the β-lactamase (penicillinase) and lactose (lac) promoter systems (Chang, et al., *Nature* (1997) 198:1056), the tryptophan (trp) promoter system (Goeddel, et al., *Nucleic Acids Res.* (1980) 8:4057) and the lambda-derived $P_L$ promoter (Shimatake, et al., *Nature* (1981) 292:128) and N-gene ribosome binding site, which has been made useful as a portable control cassette (as set forth in U.S. Pat. No. 4,711,845, issued Dec. 8, 1987), which comprises a first DNA sequence that is the $P_L$ promoter operably linked to a second DNA sequence corresponding to $N_{RBS}$ upstream of a third DNA sequence having at least one restriction site that permits cleavage within six bp 3' of the $N_{RBS}$ sequence. Also useful is the phosphatase A (phoA) system described by Chang, et al. in European Patent Publication No. 196,864 published Oct. 8, 1986, assigned to the same assignee and incorporated herein by reference. However, any available promoter system compatible with procaryotes can be used.

In addition to bacteria, eucaryotic microbes, such as yeast, may also be used as hosts. Laboratory strains of *Saccharomyces cerevisiae*, Baker's yeast, are most used, although a number of other strains are commonly available. While vectors employing the 2 micron origin of replication are illustrated (Broach, J. R., *Meth. Enz.* (1983) 101:307), other plasmid vectors suitable for yeast expression are known (see, for example, Stinchcomb, et al., *Nature* (1979) 282:39, Tschempe, et al., *Gene* (1980) 10:157 and Clarke, L., et al., *Meth. Enz.* (1983) 101:300). Control sequences for yeast vectors include promoters for the synthesis of glycolytic enzymes (Hess, et al., *J. Adv. Enzyme Reg.* (1968) 7:149; Holland, et al., *Biotechnology* (1978) 17:4900).

Additional promoters known in the art include the promoter for 3-phosphoglycerate kinase (Hitzeman, et al., *J. Biol. Chem.* (1980) 255:2073), and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters that have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization (Holland, supra).

It is also believed that terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno46 (Holland, M. J., et al., *J. Biol. Chem.* (1981) 256:1385) or the LEU2 gene obtained from YEp13 (Broach, J., et al., *Gene* (1978) 8:121); however, any vector containing a yeast-compatible promoter, origin of replication, and other control sequences is suitable.

It is also, of course, possible to express genes encoding polypeptides in eucaryotic host cell cultures derived from multicellular organisms. See, for example, *Tissue Culture*, Academic Press, Cruz and Patterson, editors (1973). Useful host cell lines include murine myelomas N51, VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers, et al., *Nature* (1978) 273:113), or other viral promoters such as those derived from polyoma, Adenovirus 2, bovine papiloma virus, or avian sarcoma viruses, or immunoglobulin promoters and heat shock promoters. A system for expressing DNA in mammalian systems using the BPV as a vector is disclosed in U.S. Pat. No. 4,419,446. A modification of this system is described in U.S. Pat. No. 4,601,978. General aspects of mammalian cell host system transformations have been described by Axel, U.S. Pat. No. 4,399,216. It now appears, also, that "enhancer" regions are important in optimizing expression; these are, generally, sequences found upstream of the promoter region. Origins of replication may be obtained, if needed, from viral sources. However, integration into the chromosome is a common mechanism for DNA replication in eucaryotes.

Plant cells are also now available as hosts, and control sequences compatible with plant cells such as the nopaline synthase promoter and polyadenylation signal sequences (Depicker, A., et al., *J. Mol. Appl. Gen.* (1982) 1:561) are available.

Recently, in addition, expression systems employing insect cells utilizing the control systems provided by baculovirus vectors have been described (Miller, D. W., et al., in *Genetic Engineering* (1986) Setlow, J. K. et al., eds., Plenum Publishing, Vol. 8, pp. 277–297). These systems are also successful in producing Taq polymerase.

Transformations

Depending on the host cell used, transformation is done using standard techniques appropriate to such cells. The calcium treatment employing calcium chloride, as described by Cohen, S. N., *Proc. Natl. Acad. Sci. (USA)* (1972) 69:2110 is used for procaryotes or other cells that contain substantial cell wall barriers. Infection with *Agrobacterium tumefaciens* (Shaw, C. H., et al., *Gene* (1983) 23:315) is used for certain plant cells. For mammalian cells without such cell walls, the calcium phosphate precipitation method of Graham and van der Eb, *Virology* (1978) 52:546 is preferred. Transformations into yeast are carried out according to the method of Van Solingen, P., et al., *J. Bact.* (1977) 130:946 and Hsiao, C. L., et al., *Proc. Natl. Acad. Sci. (USA)* (1979) 76:3829.

Construction of a λgt11 Expression Library

The strategy for isolating DNA encoding desired proteins, such as the Taq polymerase encoding DNA, using the bacteriophage vector lambda gt11, is as follows. A library can be constructed of EcoRI-flanked AluI fragments, generated by complete digestion of *Thermus aquaticus* DNA, inserted at the EcoRI site in the lambda gt11 phage (Young and Davis, *Proc. Natl. Acad. Sci USA* (1983) 80:1194–1198). Because the unique EcoRI site in this bacteriophage is located in the carboxy-terminus of the β-galactosidase gene, inserted DNA (in the appropriate frame and orientation) is expressed as protein fused with β-galactosidase under the control of the lactose operon promoter/operator.

Genomic expression libraries are then screened using the antibody plaque hybridization procedure. A modification of this procedure, referred to as "epitope selection," uses antiserum against the fusion protein sequence encoded by the phage, to confirm the identification of hybridized plaques. Thus, this library of recombinant phages could be screened with antibodies that recognize the 86,000–95,000 dalton Taq polymerase in order to identify phage that carry DNA segments encoding the antigenic determinants of this protein.

Approximately $2\times10^5$ recombinant phage are screened using total rabbit Taq polymerase antiserum. In this primary screen, positive signals are detected and one or more of these phages are purified from candidate plaques which failed to react with preimmune serum and reacted with immune serum and analyzed in some detail. To examine the fusion proteins produced by the recombinant phase, lysogens of the phase in the host Y1089 are produced. Upon induction of the lysogens and gel electrophoresis of the resulting proteins, each lysogen may be observed to produce a new protein, not found in the other lysogens, or duplicate sequences may result. Phage containing positive signals are picked; in this case, one positive plaque was picked for further identification and replated at lower densities to purify recombinants and the purified clones were analyzed by size class via digestion with EcoRI restriction enzyme. Probes can then be made of the isolated DNA insert sequences and labeled appropriately and these probes can be used in conventional colony or plaque hybridization assays described in Maniatis et al., *Molecular Cloning: A Laboratory Manual* (1982), the disclosure of which is incorporated herein by reference.

The labeled probe was used to probe a second genomic library constructed in a Charon 35 bacteriophage (Wilhelmine, A. M. et al., *Gene* (1983) 26:171–179). This library was made from Sau3A partial digestions of genomic *Thermus aquaticus* DNA and size fractionated fragments (15–20 kb) were cloned into the BamHI site of the Charon 35 phage. The probe was used to isolate phage containing DNA encoding the Taq polymerase. One of the resulting phage, designated CH35:Taq#4-2, was found to contain the entire gene sequence. Partial sequences encoding portions of the gene were also isolated.

Vector Construction

Construction of suitable vectors containing the desired coding and control sequences employs standard ligation and restriction techniques that are well understood in the art. Isolated plasmids, DNA sequences, or synthesized oligonucleotides are cleaved, tailored, and religated in the form desired.

Site-specific DNA cleavage is performed by treating with the suitable restriction enzyme (or enzymes) under conditions that are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution; in the examples herein, typically an excess of restriction enzyme is used to ensure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499–560.

Restriction-cleaved fragments may be blunt-ended by treating with the large fragment of *E. coli* DNA polymerase I (Klenow) in the presence of the four deoxynucleotide triphosphates (dNTPs) using incubation times of bout 15 to 25 minutes at 20 to 25° C. in 50 mM Tris pH 7.6, 50 mM NaCl, 10 mM $MgCl_2$, 10 mM DTT and 50–100 μM dNTPs. The Klenow fragment fills in at 5' sticky ends, but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated. Treatment under appropriate conditions with S1 nuclease results in hydrolysis of any single-stranded portion.

Synthetic oligonucleotides may be prepared using the triester method of Matteucci, et al., (*J. Am. Chem. Soc.* (1981) 103:3185–3191) or using automated synthesis methods. Kinasing of single strands prior to annealing or for labeling is achieved using an excess, e.g., approximately 10 units of polynucleotide kinase to 1 mM substrate in the presence of 50 mM Tris, pH 7.6, 10 mM $MgCl_2$, 5 mM dithiothreitol, 1–2 mM ATP. If kinasing is for labeling of probe, the ATP will contain high specific activity $\gamma$-$^{32}$P.

Ligations are performed in 15–30 μl volumes under the following standard conditions and temperatures: 20 mM Tris-Cl pH 7.5, 10 mM $MgCl_2$, 10 mM DTT, 33 μg/ml BSA, 10 mM–50 mM NaCl, and either 40 μm ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 μg/ml total DNA concentrations (5–100 mM total end concentration). Intermolecular blunt end ligations (usually employing a t10–30 fold molar excess of linkers) are performed at 1 μM total ends concentration.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of $Na^+$ and $Mg^{+2}$ using about 1 unit of BAP per mg of vector at 60° C. for about one hour. In order to recover the nucleic acid fragments, the preparation is extracted with phenol/chloroform and ethanol precipitated. Alternatively, religation can be prevented in vectors that have been double digested by additional restriction enzyme digestion of the unwanted fragments.

Modification of DNA Sequences

For portions of vectors derived from cDNA or genomic DNA that require sequence modifications, site-specific primer-directed mutagenesis is used. This technique is now standard in the art, and is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells that harbor the phage.

Theoretically, 50% of the new plaques will contain the phage having, as a single strand, the mutated form; 50% will have the original sequence. The plaques are transferred to nitrocellulose filters and the "lifts" hybridized with kinased synthetic primer at a temperature that permits hybridization of an exact match, but at which the mismatches with the original strand are sufficient to prevent hybridization. Plaques that hybridize with the probe are then picked and cultured, and the DNA is recovered.

Verification of Construction

In the constructions set forth below, correct ligations for plasmid construction are conformed by first transforming *E. coli* strain MM294, or other suitable host, with the ligation mixture. Successful transformants are selected by ampicillin, tetracycline or other antibiotic resistance or using other markers, depending on the mode of plasmid construction, as is understood in the art. Plasmids from the transformants are then prepared according to the method of Clewell, D. B., et al., *Proc. Natl. Acad. Sci.* (*USA*) (1969) 62:1159, optionally following chloramphenicol amplification (Clewell, D. B., *J. Bacteriol.* (1972) 110:667). The isolated DNA is analyzed by restriction and/or sequenced by the dideoxy method of Sanger, F., et al., *proc. Natl. Acad. Sci.* (*USA*) (1977) 74:5463 as further described by Messing, et al., *Nucleic Acids Res.* (1981) 9:309, or by the method of Maxam, et al., *methods in Enzymology* (1980) 65:499.

Host Strains Exemplified

Host strains used in cloning and expression herein are as follows:

For cloning and sequencing, and for expression of constructions under control of most bacterial promoters, *E. coli* strain MM294 obtained from *E. coli* Genetic Stock Center GCSC #6135, was used as the host. For expression under control of the $P_L N_{RBS}$ promoter, *E. coli* strain K12 MC1000 lambda lysogen, $N_7N_{53}cI857$ $SusP_{80}$, ATCC 39531 may be used. Used herein are *E. coli* DG116, which was deposited with ATCC (ATCC 53606) on Apr. 7, 1987 and *E. coli* KB2, which was deposited with ATCC (ATCC 53075) on Mar. 29, 1985.

For M13 phage recombinants, *E. coli* strains susceptible to phage infection, such as *E. coli* K12 strain DG98, are employed. The DG98 strain has been deposited with ATCC Jul. 13, 1984 and has accession number 39768.

Mammalian expression can be accomplished in COS-7 COS-A2, CV-1, and murine cells, and insect cell-based expression in *Spodoptera frugipeida*).

Purification

In addition to the purification procedures previously described, the thermostable polymerase of the invention may be purified using hydrophobic interaction chromatography. Hydrophobic interaction chromatography is a separation technique in which substances are separated on the basis of differing strengths of hydrophobic interaction with an uncharged bed material containing hydrophobic groups. Typically, the column is first equilibrated under conditions favorable to hydrophobic binding, e.g., high ionic strength. A descending salt gradient may be used to elute the sample.

According to the invention, the aqueous mixture (containing either native or recombinant polymerase) is loaded onto a column containing a relatively strong hydrophobic gel such as Phenyl Sepharose (manufactured by Pharmacia) or Phenyl TSK (manufactured by Toyo Soda). To promote hydrophobic interaction with a Phenyl Sepharose column, a solvent is used which contains, for example, greater than or equal to 0.2 M ammonium sulfate, with 0.2 M being preferred. Thus the column and the sample are adjusted to 0.2 M ammonium sulfate in 50 mM Tris-1 mM EDTA buffer and the sample applied to the column. The column is washed with the 0.2 M ammonium sulfate buffer. The enzyme may then be eluted with solvents which attenuate hydrophobic interactions such as, for example, decreasing salt gradients, ethylene or propylene glycol, or urea. For the recombinant Taq polymerase, a preferred embodiment involves washing the column sequentially with the Tris-EDTA buffer and the Tris-EDTA buffer containing 20% ethylene glycol. The Taq polymerase is subsequently eluted from the column with a 0-4 M urea gradient in the Tris-EDTA ethylene glycol buffer.

Stabilization of Enzyme Activity

For long-term stability, the enzyme herein must be stored in a buffer that contains one or more non-ionic polymeric detergents. Such detergents are generally those that have a molecular weight in the range of approximately 100 to 250,000, preferably about 4,000 to 200,000 daltons and stabilize the enzyme at a pH of from about 3.5 to about 9.5, preferably from about 4 to 8.5. Examples of such detergents include those specified on pages 295–298 of McCutcheon's *Emulsifiers & Detergents,* North American edition (1983), published by the McCutcheon Division of MC Publishing Co., 175 Rock Road, Glen Rock, N.J. (USA), the entire disclosure of which is incorporated herein by reference. Preferably, the detergents are selected from the group comprising ethoxylated fatty alcohol ethers and lauryl ethers, ethoxylated alkyl phenols, octylphenoxy polyethoxy ethanol compounds, modified oxyethylated and/or oxypropylated straight-chain alcohols, polyethylene glycol monooleate compounds, polysorbate compounds, and phenolic fatty alcohol ethers. More particularly preferred are Tween 20, from ICI Americas Inc., Wilmington, Del., which is a polyoxyethylated (20) sorbitan monolaurate, and Iconol™ NP-40, from BASF Wyandotte Corp. Parsippany, N.J., which is an ethoxylated alkyl phenol (nonyl).

the thermostable enzyme of this invention may be used for any purpose in which such enzyme is necessary or desirable. In a particularly preferred embodiment, the enzyme herein is employed in the amplification protocol set forth below.

Amplification Protocol

The amplification protocol using the enzyme of the present invention may be the process for amplifying existing nucleic acid sequences that is disclosed and claimed in U.S. Pat. No. 4,683,202, issued Jul. 28, 1987, the disclosure of which is incorporated herein by reference. Preferably, however, the enzyme herein is used in the amplification process disclosed below.

Specifically, the amplification method involves amplifying at least one specific nucleic acid sequence contained in a nucleic acid or a mixture of nucleic acids, wherein if the nucleic acid is double-stranded, it consists of two separated complementary strands of equal or unequal length, which process comprises:

(a) contacting each nucleic acid strand with four different nucleotide triphosphates and one oligonucleotide primer for each different specific sequence being amplified, wherein each primer is selected to be substantially complementary to different strands of each specific sequence, such that the extension product synthesized from one primer, when it is separated from its complement, can serve as a template for synthesis of the extension product of the other primer, said contacting being at a temperature which promotes hybridization of each primer to its complementary nucleic acid strand;

(b) contacting each nucleic acid strand, at the same time as or after step (a), with a DNA polymerase from *Thermus aquaticus* which enables combination of the nucleotide triphosphates to form primer extension products complementary to each strand of each nucleic acid;

(c) maintaining the mixture from step (b) at an effective temperature for an effective time to promote the activity of the enzyme, and to synthesize, for each different sequence being amplified, an extension product of each primer which is complementary to each nucleic acid strand template, but not so high as to separate each extension product from its complementary strand template;

(d) heating the mixture from step (c) for an effective time and at an effective temperature to separate the primer extension products from the templates on which they were synthesized to produce single-stranded molecules, but not so high as to denature irreversibly the enzyme;

(e) cooling the mixture from step (d) for an effective time and to an effective temperature to promote hybridization of each primer to each of the single-stranded molecules produced in step (d); and (f) maintaining the mixture from step (e) at an effective temperature for an effective time to promote the activity of the enzyme and to synthesize, for each different sequence being amplified, an extension product of each primer which is complementary to each nucleic acid strand template produced in step (d), but not so high as to separate each extension product from its complementary strand template wherein the effective time and temperatures in steps (e) and (f) may coincide (steps (e) and (f) are carried out simultaneously), or may be separate.

Steps (d)–(f) may be repeated until the desired level of sequence amplification is obtained.

The amplification method is useful not only for producing large amounts of an existing completely specified nucleic acid sequence, but also for producing nucleic acid sequences which are known to exist but are not completely specified. In either case an initial copy of the sequence to be amplified must be available, although it need not be pure or a discrete molecule.

In general, the amplification process involves a chain reaction for producing, in exponential quantities relative to the number of reaction steps involved, at least one specific nucleic acid sequence given (a) that the ends of the required sequence are known in sufficient detail that oligonucleotides can be synthesized which will hybridize to them, and (b) that a small amount of the sequence is available to initiate the chain reaction. The product of the chain reaction will be a discrete nucleic acid duplex with termini corresponding to the ends of the specific primers employed.

Any nucleic acid sequence, in purified or nonpurified form, can be utilized as the starting nucleic acid(s), provided it contains or is suspected to contain the specific nucleic acid sequence desired. Thus, the process may employ, for example, DNA or RNA, including messenger RNA, which DNA or RNA may be single-stranded or double-stranded. In addition, a DNA-RNA hybrid which contains one strand of each may be utilized. A mixture of any of these nucleic acids may also be employed, or the nucleic acids produced from a previous amplification reaction herein using the same or different primers may be so utilized. The specific nucleic acid sequence to be amplified may be only a fraction of a larger molecule or can be present initially as a discrete molecule, so that the specific sequence constitutes the entire nucleic acid.

It is not necessary that the sequence to be amplified be present initially in a pure form; it may be a minor fraction of a complex mixture, such as a portion of the β-globin gene contained in whole human DNA (as exemplified in Saiki et al., *Science*, 230, 1530–1534 (1985)) or a portion of a nucleic acid sequence due to a particular microorganism which organism might constitute only a very minor fraction of a particular biological sample. The starting nucleic acid sequence may contain more than one desired specific nucleic acid sequence which may be the same or different. Therefore, the amplification process is useful not only for producing large amounts of one specific nucleic acid sequence, but also for amplifying simultaneously more than one different specific nucleic acid sequence located on the same or different nucleic acid molecules.

The nucleic acid(s) may be obtained from any source, for example, from plasmids such as pBR322, from cloned DNA or RNA, or from natural DNA or RNA from any source, including bacteria, yeast, viruses, organelles, and higher organisms such as plants or animals. DNA or RNA may be extracted from blood, tissue material such as chorionic villi, or amniotic cells by a variety of techniques such as that described by Maniatis et al., supra, p. 280–281.

If probes are used which are specific to a sequence being amplified and thereafter detected, the cells may be directly used without extraction of the nucleic acid if they are suspended in hypotonic buffer and heated to about 90–100° C., until cell lysis and dispersion of intracellular components occur, generally 1 to 15 minutes. After the heating step the amplification reagents may be added directly to the lysed cells.

Any specific nucleic acid sequence can be produced by the amplification process. It is only necessary that a sufficient number of bases at both ends of the sequence be known in sufficient detail so that two oligonucleotide primers can be prepared which will hybridize to different strands of the desired sequence and at relative positions along the sequence such that an extension product synthesized from one primer, when it is separated from its template (complement), can serve as a template for extension of the other primer into a nucleic acid sequence of defined length. The greater the knowledge about the bases at both ends of the sequence, the greater can be the specificity of the primers for the target nucleic acid sequence, and thus the greater the efficiency of the process.

It will be understood that the work "primer" as used hereinafter may refer to more than one primer, particularly in the case where there is some ambiguity in the information regarding the terminal sequence(s) of the fragment to be amplified. For instance, in the case where a nucleic acid sequence is inferred from protein sequence information, a collection of primers containing sequences representing all possible codon variations based on degeneracy of the genetic code will be used for each strand. One primer from this collection will be homologous with the end of the desired sequence to be amplified.

The oligonucleotide primers may be prepared using any suitable method, such as, for example, the phsophotriester and phosphodiester methods described above, or automated embodiments thereof. In one such automated embodiment, diethylphosphoramidites are used as starting materials and may be synthesized as described by Beaucage et al., *Tetrahedron Letters* (1981), 22:1859–1862. One method for synthesizing oligonucleotides on a modified solid support is described in U.S. Pat. No. 4,458,066. It is also possible to use a primer which has been isolated from a biological source (such as a restriction endonuclease digest).

The specific nucleic acid sequence is produced by using the nucleic acid containing that sequence as a template. The first step involves contacting each nucleic acid strand with four different nucleotide triphosphates and one oligonucleotide primer for each different nucleic acid sequence being amplified or detected. If the nucleic acids to be amplified or detected are DNA, then the nucleotide triphosphates are dATP, dCTP, dGTP and TTP.

The nucleic acid strands are used as a template for the synthesis of additional nucleic acid strands. This synthesis can be performed using any suitable method. Generally, it occurs in a buffered aqueous solution, preferably at a pH of 7–9, most preferably about 8. Preferably, a molar excess (for cloned nucleic acid, usually about 1000:1 primer:template, and for genomic nucleic acid, usually about $10^8$:1 primer:template) of the two oligonucleotide primers is added to the buffer containing the separated template strands. It is understood, however, that the amount of complementary strand may not be known if the process herein is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

Preferably the concentration of nucleotide triphosphates is 150–200 $\mu$M each in the buffer for amplification and $MgCl_2$ is present in the buffer in an amount of 1.5–2 mM to increase the efficiency and specificity of the reaction.

The resulting solution is then treated according to whether the nucleic acids being amplified or detected are double or single-stranded. If the nucleic acids are single-stranded, then no denaturation step need be employed, and the reaction mixture is held at a temperature which promotes hybridization of the primer to its complementary target (template) sequence. Such temperature is generally from about 35° C. to 65° C. or more, preferably about 37–60° C. for an effective time, generally one-half to five minutes, preferably one-three minutes. Preferably, 45–58° C. is used for Taq polymerase and >15-mer primers to increase the specificity of primer hybridization. Shorter primers need lower temperatures.

The complement to the original single-stranded nucleic acid may be synthesized by adding one or two oligonucleotide primers thereto. If an appropriate single primer is added, a primer extension product is synthesized in the presence of the primer, the DNA polymerase from *Thermus aquaticus* and the nucleotide triphosphates. The product will be partially complementary to the single-stranded nucleic acid and will hybridize with the nucleic acid strand to form a duplex of strands of unequal length which may then be separated into single strands as described above to produce two single separated complementary strands. Alternatively, two appropriate primers may be added to the single-stranded nucleic acid and the reaction carried out.

If the nucleic acid contains two strands, it is necessary to separate the strands of the nucleic acid before it can be used as the template. This strand separation can be accomplished by any suitable denaturing method including physical, chemical or enzymatic means. One preferred physical method of separating the strands of the nucleic acid involves heating the nucleic acid until it is completely (>99%) denatured. Typical heat denaturation involves temperatures ranging from about 90 to 105° C. for times generally ranging from about 0.5 to 5 minutes. Preferably the effective denaturing temperature is 90–100° C. for 0.5 to 3 minutes. Strand separation may also be induced by an enzyme from the class of enzymes known as helicases or the enzyme RecA, which has helicase activity and in the presence of riboATP is known to denature DNA. The reaction conditions suitable for separating the strands of nucleic acids with helicases are described by Kuhn Hoffmann-Berling, *CSM*-Quantitative Biology, 43:63 (1978), and techniques for using RecA are reviewed in C. Radding, *Ann. Rev. Genetics,* 16:405–37 (1982). The denaturation produces two separated complementary strands of equal of unequal length.

If the double-stranded nucleic acid is denatured by heat, the reaction mixture is allowed to cool to a temperature which promotes hybridization of each primer present to its complementary target (template) sequence. This temperature is usually from about 35° C. to 65° C. or more, depending on reagents, preferably 37–60° C., maintained for an effective time, generally 0.5 to 5 minutes, and preferably 1–3 minutes. In practical terms, the temperature is simply lowered from about 95° C. to as low as 37° C., preferably to about 45–58° C. for Taq polymerase, and hybridization occurs at a temperature within this range.

Whether the nucleic acid is single- or double-stranded, the DNA polymerase from *Thermus aquaticus* may be added at the denaturation step or when the temperature is being reduced to or is in the range for promoting hybridization. The reaction mixture is then heated to a temperature at which the activity of the enzyme is promoted or optimized, i.e., a temperature sufficient to increase the activity of the enzyme in facilitating synthesis of the primer extension products from the hybridized primer and template. The temperature must actually be sufficient to synthesize an extension product of each primer which is complementary to each nucleic acid template, but must not be so high as to denature each extension product from its complementary template (i.e., the temperature is generally less than about 80° C.–90° C.).

Depending mainly on the types of enzyme and nucleic acid(s) employed, the typical temperature effective for this synthetic reaction generally ranges from about 40 to 80° C., preferably 50–75° C. The temperature more preferably ranges from about 65–75° C. when a DNA polymerase from *Thermus aquaticus* is employed. The period of time required for this synthesis may range from about 0.5 to 40 minutes or more, depending mainly on the temperature, the length of the nucleic acid, the enzyme and the complexity of the nucleic acid mixture, preferably one to three minutes. If the nucleic acid is longer, a longer time period is generally required. The presence of dimethylsulfoxide (DMSO) is not necessary or recommended because DMSO was found to inhibit Taq polymerase enzyme activity.

The newly synthesized stand and its complementary nucleic acid strand form a double-stranded molecule which is used in the succeeding steps of the process. In the next step, the strands of the double-stranded molecule are separated by heat denaturation at a temperature effective to denature the molecule, but not so high that the thermostable enzyme is completely and irreversibly denatured or inactivated. Depending mainly on the type of enzyme and the length of nucleic acid, this temperature generally ranges from about 90 to 105° C., more preferably 90–100° C., and the time for denaturation typically ranges from 0.5 to four minutes, depending mainly on the temperature and nucleic acid length.

After this time, the temperature is decreased to a level which promotes hybridization of the primer to its complementary single-stranded molecule (template) produced from the previous step. Such temperature is described above.

After this hybridization step, or in lieu of (or concurrently with) the hybridization step, the temperature is adjusted to a temperature that is effective to promote the activity of the thermostable enzyme to enable synthesis of a primer extension product using as template the newly synthesized strand from the previous step. The temperature again must not be so high as to separate (denature) the extension product from its template, as previously described (usually from 40 to 80° C. for 0.5 to 40 minutes, preferably 50 to 70° C. for one-three minutes). Hybridization may occur during this step, so that the previous step of cooling after denaturation is not required. In such a case, using simultaneous steps, the preferred temperature range is 50–70° C.

The heating and cooling steps of strand separation, hybridization, and extension products synthesis can be repeated as often as needed to produce the desired quantity of the specific nucleic acid sequence, depending on the ultimate use. The only limitation is the amount of the primers, thermostable enzyme and nucleotide triphosphates present. Preferably, the steps are repeated at least twice. For use in detection, the number of cycles will depend, e.g., on the nature of the sample. For example, fewer cycles will be required if the sample being amplified is pure. If the sample is a complex mixture of nucleic acids, more cycles will be required to amplify the signal sufficiently for its detection. For general amplification and detection, preferably the process is repeated at least 20 times.

When labeled sequence-specific probes are employed as described below, preferably the steps are repeated at least five times. When human genomic DNA is employed with such probes, the process is repeated preferably 15–30 times to amplify the sequence sufficiently that a clearly detectable signal is produced, i.e., so that background noise does not interfere with detection.

As will be described in further detail below, the amount of the specific nucleic acid sequence produced will accumulate in an exponential fashion.

No additional nucleotides, primers, or thermostable enzyme need be added after the initial addition, provided that the enzyme has not become denatured or inactivated irreversibly, in which case it is necessary to replenish the enzyme after each denaturing step. Addition of such materials at each step, however, will not adversely affect the reaction.

When it is desired to produce more than one specific nucleic acid sequence from the first nucleic acid or mixture of nucleic acids, the appropriate number of different oligonucleotide primers are utilized. For example, if two different specific nucleic acid sequences are to be produced, four primers are utilized. Two of the primers are specific for one of the specific nucleic acid sequences and the other two primers are specific for the second specific nucleic acid sequence. In this manner, each of the two different specific sequences can be produced exponentially by the present process.

After the appropriate length of time has passed to produce the desired amount of the specific nucleic acid sequence, the reaction may be halted by inactivating the enzyme in any known manner (e.g., by adding EDTA, phenol, SDS, or $CHCl_3$) or by separating the components of the reaction.

The amplification process may be conducted continuously. In one embodiment of an automated process, the reaction mixture may be temperature cycled such that the temperature is programmed to be controlled at a certain level for a certain time.

One such instrument for this purpose is the automated machine for handling the amplification reaction of this invention described in now abandoned Ser. No. 833,368 filed Feb. 25, 1986 entitled "Apparatus And Method For Performing Automated Amplification of Nucleic Acid Sequences And Assays Using Heating And Cooling Steps," the disclosure of which is incorporated herein by reference. Briefly, this instrument utilizes a liquid handling system under computer control to make liquid transfers of enzyme stored at a controlled temperature in a first receptacle into a second receptacle whose temperature is controlled by the computer to conform to a certain incubation profile. The second receptacle stores the nucleic acid sequence(s) to be amplified plus the nucleotide triphosphates and primers. The computer includes a user interface through which a user can enter process parameters that control the characteristics of the various steps in the amplification sequence such as the times and temperatures of incubation, the amount of enzyme to transfer, etc.

A preferred machine that may be employed utilizes temperature cycling without a liquid handling system because the enzyme need not be transferred at every cycle. Such a machine is described more completely in European Patent Application No. 236,069, published Sep. 9, 1987, the disclosure of which is incorporated herein by reference. Briefly, this instrument consists of the following system:

1. A heat-conducting container for holding a given number of tubes, preferably 500 $\mu$l tubes, which contain the reaction mixture of nucleotide triphosphates, primers, nucleic acid sequences, and enzyme.

2. A means to heat, cool, and maintain the heat-conducting container above and below room temperature, which means has an input for receiving a control signal for controlling which of the temperatures at or to which the container is heated, cooled or maintained. (These may be Peltier heat pumps available from Materials Electronics Products Corporation of Trenton, N.J. or a water heat exchanger.)

3. A computer means (e.g., a microprocessor controller), coupled to the input of said means, to generate the signals that control automatically the amplification sequence, the temperature levels, and the temperature ramping and timing.

The amplification protocol is demonstrated diagrammatically below, where double-stranded DNA containing the desired sequence [S] comprised of complementary strands [S⁺] and [S⁻] is utilized as the nucleic acid. During the first and each subsequent reaction cycle, extension of each oligonucleotide primer on the original template will produce one new ssDNA molecule product of indefinite length that terminates with only one of the primers. These products, hereafter referred to as "long products," will accumulate in a linear fashion; that is, the amount present after any number of cycles will be proportional to the number of cycles.

The long products thus produced will act as templates for one or the other of the oligonucleotide primers during subsequent cycles and will produce molecules of the desired sequence [S⁺] or [S⁻]. These molecules will also function as templates for one or the other of the oligonucleotide primers, producing further [S⁺] and [S⁻], and thus a chain reaction can be sustained that will result in the accumulation of [S] at an exponential rate relative to the number of cycles.

By-products formed by oligonucleotide hybridization other than those intended are not self-catalytic (except in rare instances) and thus accumulate at a linear rate.

The specific sequence to be amplified, [S], can be depicted diagrammatically as:

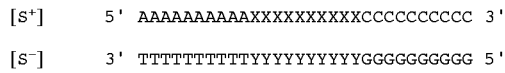

The appropriate oligonucleotide primers would be:

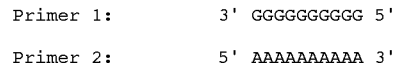

so that if DNA containing [S]

```
....zzzzzzzzzzzzzzzAAAAAAAAAAXXXXXXXXXXCCCCCCCCCCzzzzzzzzzzzzzzzz....
....zzzzzzzzzzzzzzzTTTTTTTTTTYYYYYYYYYYGGGGGGGGGGzzzzzzzzzzzzzzzz....
``` is separated into single strands and its single strands are hybridized to Primers 1 and 2, the following extension reactions can be catalyzed by a thermostable polymerase in the presence of the four nucleotide triphosphates:

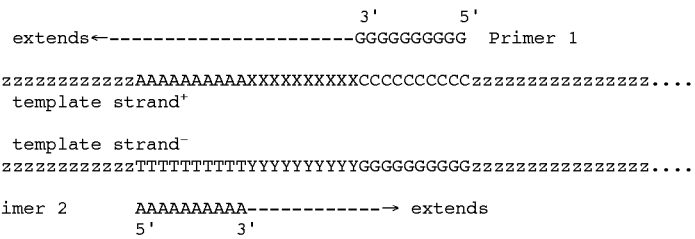

On denaturation of the two duplexes formed, the products are:

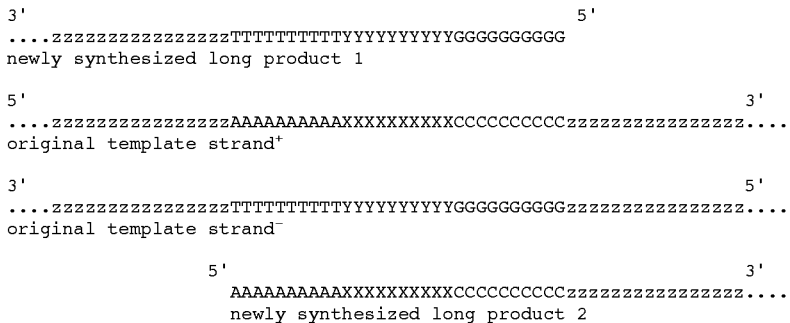

If these four strands are allowed to rehybridize with Primers 1 and 2 in the next cycle, the thermostable polymerase will catalyze the following reactions:

```
       Primer 2      5' AAAAAAAAAA----------------→ extends to here

3'....zzzzzzzzzzzzzzzzzzTTTTTTTTTTTYYYYYYYYYYGGGGGGGGGG 5'
newly synthesized long product 1 extends ←----------------------- GGGGGGGGGG 5' Primer 1

5'....zzzzzzzzzzzzzzAAAAAAAAAAXXXXXXXXXXCCCCCCCCCCzzzzzzzzzzzzzzzz....3'
original template strand⁺

Primer 2      5' AAAAAAAAAA------------------------→ extends

3'....zzzzzzzzzzzzzzzzzzTTTTTTTTTTTYYYYYYYYYYGGGGGGGGGGzzzzzzzzzz....5'
original template strand⁻ extends to here ←-----------------GGGGGGGGGG  5'  Primer 1

5' AAAAAAAAAAXXXXXXXXXXCCCCCCCCCCzzzzzzzzzzzzzzzz..3'
                 newly synthesized long product 2
```

If the strands of the above four duplexes are separated, the following strands are found:

```
              5' AAAAAAAAAAXXXXXXXXXXCCCCCCCCCC 3'
                 newly synthesized [S⁺]

3'....zzzzzzzzzzzzzzzzzzTTTTTTTTTTTYYYYYYYYYYGGGGGGGGGG 5'
first cycle synthesized long product 1

3'....zzzzzzzzzzzzzzzzzzTTTTTTTTTTTYYYYYYYYYYGGGGGGGGGG 5'
newly synthesized long product 1

5'....zzzzzzzzzzzzzzzzzzAAAAAAAAAAXXXXXXXXXXCCCCCCCCCCzzzzzzzz....3'
original template strand⁺

5' AAAAAAAAAAXXXXXXXXXXCCCCCCCCCCzzzzzzzzzzzzzzzz...3'
                 newly synthesized long product 2

3'..zzzzzzzzzzzzzTTTTTTTTTTTYYYYYYYYYYGGGGGGGGGGzzzzzzzzzzzzzzzz...5'
original template strand⁻

3' TTTTTTTTTTTYYYYYYYYYYGGGGGGGGGG 5'
                 newly synthesized [S⁻]

5' AAAAAAAAAAXXXXXXXXXXCCCCCCCCCCzzzzzzzzzzzzzzzz...3'
                 first cycle synthesized long product 2
```

It is seen that each strand which terminates with the oligonucleotide sequence of one primer and the complementary sequence of the other is the specific nucleic acid sequence [S] that is desired to be produced.

The amount of the original nucleic acid remains constant in the entire process, because it is not replicated. The amount of the long products increases linearly because they are produced only from the original nucleic acid. The amount of the specific sequence increases exponentially. Thus, the specific sequence will become the predominant species. This is illustrated in the following table, which indicates the relative amounts of the specific theoretically present after n cycles, assuming 100% efficiency at each cycle:

| | Number of Double Strands After 0 to n Cycles | | |
|---|---|---|---|
| Cycle Number | Template | Long Products | Specific Sequence [S] |
| 0 | 1 | — | — |
| 1 | 1 | 1 | 0 |
| 2 | 1 | 2 | 1 |
| 3 | 1 | 3 | 4 |
| 5 | 1 | 5 | 26 |
| 10 | 1 | 10 | 1013 |
| 15 | 1 | 15 | 32,752 |
| 20 | 1 | 20 | 1,048,555 |
| n | 1 | n | $(2^n - n - 1)$ |

When a single-stranded nucleic acid is utilized as the template, only one long produce is formed per cycle.

A sequence within a given sequence can be amplified after a given number of amplifications to obtain greater specificity of the reaction by adding after at least one cycle or amplification a set of primers that are complementary to internal sequences (that are not on the ends) of the sequence to be amplified. Such primers may be added at any stage and will provide a shorter amplified fragment. Alternatively, a longer fragment can be prepared by using primers with non-complementary ends but having some overlap with the primers previously utilized in the amplification.

The amplification method may be utilized to clone a particular nucleic acid sequence for insertion into a suitable expression vector. The vector may be used to transform an appropriate host organism to produce the gene product of the sequence by standard methods of recombinant DNA technology. Such cloning may involve direct ligation into a vector using blunt-end ligation, or use of restriction enzymes to cleave at sites contained within the primers.

In addition, the amplification process can be used for in vitro mutagenesis. The oligodeoxyribonucleotide primers need not be exactly complementary to the DNA sequence that is being amplified. It is only necessary that they be able to hybridize to the sequence sufficiently well to be extended by the thermostable enzyme. The product of an amplification reaction wherein the primers employed are not exactly complementary to the original template will contain the sequence of the primer rather than the template, thereby introducing an in vitro mutation. In further cycles this mutation will be amplified with an undiminished efficiency because no further mispaired priming is required. The mutant thus produced may be inserted into an appropriate vector by standard molecular biological techniques and might confer mutant properties on this vector such as the potential for production of an altered protein.

The process of making an altered DNA sequence as described above could be repeated on the altered DNA using different primers to induce further sequence changes. In this way, a series of mutated sequences could gradually be produced wherein each new addition to the series could differ from the last in a minor way, but from the original DNA source sequence in an increasingly major way. In this manner, changes could be made ultimately which were not feasible in a single step due to the inability of a very seriously mismatched primer to function.

In addition, the primer can contain as part of its sequence a non-complementary sequence, provided that a sufficient amount of the primer contains a sequence that is complementary to the strand to be amplified. For example, a nucleotide sequence that is not complementary to the template sequence (such as, e.g., a promoter, linker, coding sequence, etc.) may be attached at the 5' end of one or both of the primers, and thereby appended to the produce of the amplification process. After the extension primer is added, sufficient cycles are run to achieve the desired amount of new template containing the non-complementary nucleotide insert. This allows production of large quantities of the combined fragments in a relatively short period of time (e.g., two hours or less) using a simple technique.

The amplification method may also be used to enable detection and/or characterization of specific nucleic acid sequences associated with infectious diseases, genetic disorders or cellular disorders such as cancer, e.g., oncogenes. Amplification is useful when the amount of nucleic acid available for analysis is very small, as, for example, in the prenatal diagnosis of sickle cell anemia using DNA obtained from fetal cells. Amplification is particularly useful if such an analysis is to be done on a small sample using non-radioactive detection techniques which may be inherently insensitive, or where radioactive techniques are being employed, but where rapid detection is desirable.

For the purposes of this discussion, genetic diseases may include specific deletions and/or mutations in genomic DNA from an organism, such as, e.g., sickle cell anemia, cystic fibrosis, α-thalassemia, β-thalassemia, and the like. Sickle cell anemia can be readily detected via oligomer restriction analysis as described by EP Patent Publication 164,054 published Dec. 11, 1985, or via a RFLP-like analysis following amplification of the appropriate DNA sequence by the amplification method. α-Thalassemia can be detected by the absence of a sequence, and β-thalassemia can be detected by the presence of a polymorphic restriction site closely linked to a mutation that causes the disease.

All of these genetic diseases may be detected by amplifying the appropriated sequence and analyzing it by Southern blots without using radioactive probes. In such a process, for example, a small sample of DNA from, e.g., amniotic fluid containing a very low level of the desired sequence is amplified, cut with a restriction enzyme, and analyzed via a Southern blotting technique. The use of non-radioactive probes is facilitated by the high level of the amplified signal.

In another embodiment, a small sample of DNA may be amplified to a convenient level and then a further cycle of extension reactions performed wherein nucleotide derivatives which are readily detectable (such as $^{32}$P-labeled or biotin-labeled nucleotide triphosphates) are incorporated directly into the final DNA product, which may be analyzed by restriction and electrophoretic separation or any other appropriate method.

In a further embodiment, the nucleic acid may be exposed to a particular restriction endonuclease prior to amplification. Since a sequence which has been cut cannot be amplified, the appearance of an amplified fragment, despite prior restriction of the DNA sample, implies the absence of a site for the endonuclease within the amplified sequence. The presence or absence of an amplified sequence can be detected by an appropriate method.

A practical application of the amplification technique, that is, in facilitating the detection of sickle anemia via the oligomer restriction technique [described in EP 164,054, supra, and by Saiki et al., *Bio/Technology*, Vol. 3, pp. 1008–1012 (1985)] is described in detail in the Saiki et al. *Science* article cited above. In that *Science* article, a specific amplification protocol is exemplified using a β-globin gene segment.

The amplification method herein may also be used to detect directly single-nucleotide variations in nucleic acid sequence (such as genomic DNA) using sequence-specific oligonucleotides, as described more fully in European Patent Publication 237,362, published Sep. 16, 1987, the disclosure of which is incorporated herein by reference.

Briefly, in this process, the amplified sample is spotted directly on a series of membranes, and each membrane is hybridized with a different labeled sequence-specific oligonucleotide probe. After hybridization the sample is washed and the label is detected. This technique is especially useful in detecting DNA polymorphisms.

Various infectious diseases can be diagnosed by the presence in clinical samples of specific DNA sequences characteristic of the causative microorganism. These include bacteria, such as Salmonella, Chlamydia, Neisseria; viruses, such as the hepatitis viruses, and parasites, such as the Plasmodium responsible for malaria. U.S. Patent Reexamination Certificate B1 4,358,535 issued to Falkow et al. on May 13, 1986 describes the use of specific DNA hybridization probes for the diagnosis of infectious diseases. A relatively small number of pathogenic organisms may be present in a clinical sample from an infected patient and the DNA extracted from these may constitute only a very small fraction of the total DNA in the sample. Specific amplification of suspected pathogen-specific sequences prior to immobilization and detection by hybridization of the DNA samples could greatly improve the sensitivity and specificity of traditional procedures.

Routine clinical use of DNA probes for the diagnosis of infectious diseases would be simplified considerably if non-radioactively labeled probes could be employed as described in EP 63,879 to Ward. In this procedure biotin-containing DNA probes are detected by chromogenic enzymes linked to avidin or biotin-specific antibodies. This type of detection is convenient, but relatively insensitive. The combination of specific DNA amplification by the present method and the use of stably labeled probes could provide the convenience and sensitivity required to make the Falkow et al. and Ward procedures useful in a routine clinical setting.

A specific use of the amplification technology for detecting or monitoring for the AIDS virus is described in European Patent Publication 229,701, published Jul. 22, 1987, the disclosure of which is incorporated herein by reference. Briefly, the amplification and detection process is used with primers and probes which are designed to amplify and detect, respectively, nucleic acid sequences that are substantially conserved among the nucleic acids in AIDS viruses and specific to the nucleic acids in AIDS viruses. Thus, the sequence to be detected must be sufficiently complementary to the nucleic acids in AIDS viruses to initiate polymerization preferably at room temperature in the presence of the enzyme and nucleotide triphosphates.

A preferred amplification process described in U.S. Ser. No. 07/076,394, filed Jul. 22, 1987, assigned to the same assignee, and incorporated herein by reference, uses labeled primers. The label on the amplified product may be used to "capture" or immobilize the product for subsequent detection (e.g., biotinylated amplification primers yield labeled products that can be "captured" by their interaction with avidin or strepavidin). As demonstrated in the aforementioned amplification protocols, the extension product of one labeled primer when hybridized to the other becomes a template for the production of the desired specific nucleic acid sequence, and vice versa, and the process is repeated as often as necessary to produce the desired amount of the sequence. Examples of specific preferred reagents that can be employed as the label are provided in U.S. Pat. No. 4,582,789, the disclosure of which is incorporated herein by reference.

The amplification process can also be utilized to produce sufficient quantities of DNA from a single copy human gene such that detection by a simple non-specific DNA stain such as ethidium bromide can be employed to diagnose DNA directly.

In addition to detecting infectious diseases and pathological abnormalities in the genome of organisms, the amplification process can also be used to detect DNA polymorphisms which may not be associated with any pathological state.

In summary, the amplification process is seen to provide a process for amplifying one or more specific nucleic acid sequences using a chain reaction and a thermostable enzyme, in which reaction primer extension products are produced which can subsequently act as templates for further primer extension reactions. The process is especially useful in detecting nucleic acid sequences which are initially present in only very small amounts.

The following examples are offered by way of illustration only and are by no means intended to limit the scope of the claimed invention. In these examples, all percentages are by weight if for solids and by volume if for liquids, unless otherwise noted, and all temperatures are given in degrees Celsius.

EXAMPLE 1

A. Synthesis of the Primers

The following two oligonucleotide primers were prepared by the method described below:

```
5'-ACACAACTGTGTTCACTAGC-3'     (PC03)

5'-CAACTTCATCCACGTTCACC-3'     (PC04)
```

These primers, both 20-mers, anneal to opposite strands of the genomic DNA with their 5' ends separated by a distance of 110 base pairs.

1. Automated Synthesis Procedures: The diethylphosphoramidites, synthesized according to Beaucage and Caruthers (*Tetrahedron Letters* (1981) 22:1859–1862) were sequentially condensed to a nucleoside derivatized controlled pore glass support using a Biosearch SAM-1. The procedure included detritylation with trichloroacetic acid in dichloromethane, condensation using benzotriazole as activating proton donor, and capping with acetic anhydride and dimethylaminopyridine in tetrahydrofuran and pyridine. Cycle time was approximately 30 minutes. Yields at each step were essentially quantitative and were determined by collection and spectroscopic examination of the dimethoxytrityl alcohol released during detritylation.

2. Oligodeoxyribonucleotide Deprotection and Purification Procedures: The solid support was removed from the column and exposed to 1 ml concentrated ammonium hydroxide at room temperature for four hours in a closed tube. The support was then removed by filtration and the solution containing the partially protected oligodeoxynucleotide was brought to 55° C. for five hours. Ammonia was removed and the residue was applied to a preparative polyacrylamide gel. Electrophoresis was carried out at 30 volts/cm for 90 minutes after which the band containing the product was identified by UV shadowing of a fluorescent plate. The band was excised and eluted with 1 ml distilled water overnight at 4° C. This solution was applied to an Altech RP18 column and eluted with a 7–13% gradient of acetonitrile in 1% ammonium acetate buffer at pH 6.0. The elution was monitored by UV absorbance at 260 nm and the appropriate fraction collected, quantitated by UV absorbance in a fixed volume and evaporated to dryness at room temperature in a vacuum centrifuge.

3. Characterization of Oligodeoxyribonucleotides: Test aliquots of the purified oligonucleotides were $^{32}P$ labeled with polynucleotide kinase and $\gamma$-$^{32}P$-ATP. The labeled compounds were examined by autoradiography of 14–20% polyacrylamide gels after electrophoresis for 45 minutes at 50 volts/cm. This procedure verifies the molecular weight. Base composition was determined by digestion of the oligodeoxyribonucleotide to nucleosides by use of venom diesterase and bacterial alkaline phosphatase and subsequent separation and quantitation of the derived nucleosides using a reverse phase HPLC column and a 10% acetonitrile, 1% ammonium acetate mobile phase.

B. Isolation of Human Genomic DNA from Cell Line

High molecular weight genomic DNA was isolated from a T cell line, Molt 4, homozygous for normal β-globin available from the Human Genetic Mutant Cell Depository, Camden, N.J. as GM2219C using essentially the method of Maniatis et al., supra, p. 280–281.

C. Purification of a Polymerase From *Thermus aquaticus*

*Thermus aquaticus* strain YT1, available without restriction from the American Type Culture Collection, 12301 Parklawn Drive, Rockville, Md., as ATCC No. 25,104 was grown in flasks in the following medium:

| | |
|---|---|
| Sodium Citrate | 1 mM |
| Potassium Phosphate, pH 7.9 | 5 mM |
| Ammonium Chloride | 10 mM |
| Magnesium Sulfate | 0.2 mM |
| Calcium Chloride | 0.1 mM |
| Sodium Chloride | 1 g/l |
| Yeast Extract | 1 g/l |
| Tryptone | 1 g/l |
| Glucose | 2 g/l |
| Ferrous Sulfate | 0.01 mM |

(The pH was adjusted to 8.0 prior to autoclaving.)

A 10-liter fermentor was inoculated from a seed flask cultured overnight in the above medium at 70° C. A total of 600 ml from the seed flask was used to inoculate 10 liters of the same medium. The pH was controlled at 8.0 with ammonium hydroxide with the dissolved oxygen at 40%, with the temperature at 70° C., and with the stirring rate at 400 rpm.

After growth of the cells, they were purified using the protocol (with slight modification) of Kaledin et al., supra, through the first five stages and using a different protocol for the sixth stage. All six steps were conducted at 4° C. The rate of fractionation on columns was 0.5 columns/hour and the volumes of gradients during elution were 10 column volumes. An alternative and preferred purification protocol is provided in Example XIII below.

Briefly, the above culture of the *T. aquaticus* cells was harvested by centrifugation after nine hours of cultivation, in late log phase, at a cell density of 1.4 g dry weight/l. Twenty grams of cells were resuspended in 80 ml of a buffer consisting of 50 mM Tris.HCl pH 7.5, 0.1 mM EDTA. Cells were lysed and the lysate was centrifuged for two hours at 35,000 rpm in a Beckman TI 45 rotor at 4° C. The supernatant was collected (fraction A) and the protein fraction precipitating between 45 and 75% saturation of ammonium sulfate was collected, dissolved in a buffer consisting of 0.2 M potassium phosphate buffer, pH 6.5, 10 mM 2-mercaptoethanol, and 5% glycerine, and finally dialyzed against the same buffer to yield fraction B.

Fraction B was applied to a 2.2×30-cm column of DEAE-cellulose, equilibrated with the above described buffer. The column was then washed with the same buffer and the fractions containing protein (determined by absorbance at 280 nm) were collected. The combined protein fraction was dialyzed against a second buffer, containing 0.01 M potassium phosphate buffer, pH 7.5, 10 mM 2-mercaptoethanol, and 5% glycerine, to yield fraction C.

Fraction C was applied to a 2.6×21-cm column of hydroxyapatite, equilibrated with a second buffer. The column was then washed and the enzyme was eluted with a linear gradient of 0.01–0.5 M potassium phosphate buffer, pH 7.5, containing 10 mM 2-mercaptoethanol and 5% glycerine. Fractions containing DNA polymerase activity (90–180 mM potassium phosphate) were combined, concentrated four-fold using an Amicon stirred cell and YM10 membrane, and dialyzed against the second buffer to yield fraction D.

Fraction D was applied to a 1.6×28-cm column of DEAE-cellulose, equilibrated with the second buffer. The column was washed and the polymerase was eluted with a linear gradient of 0.01–0.5 M potassium phosphate in the second buffer. The fractions were assayed for contaminating endonuclease(s) and exonuclease(s) by electrophoretically detecting the change in molecular weight of phage λ DNA or supercoiled plasmid DNA after incubation with an excess of DNA polymerase (for endonuclease) and after treatment with a restriction enzyme that cleaves the DNA into several fragments (for exonuclease). Only those DNA polymerase fractions (65–95 mM potassium phosphate) having minimal nuclease contamination were pooled. To the pool was added autoclaved gelatin in an amount of 250 µg/ml, and dialysis was conducted against the second buffer to yield Fraction E.

Fraction E was applied to a phosphocellulose column and eluted with a 100 ml gradient (0.01–0.4 M KCl gradient in 20 mM potassium phosphate buffer pH 7.5). The fractions were assayed for contaminating endo/exonuclease(s) as described above as well as for polymerase activity (by the method of Kaledin et al.) and then pooled. The pooled fractions were dialyzed against the second buffer, then concentrated by dialysis against 50% glycerine and the second buffer.

The molecular weight of the polymerase was determined by SDS-PAGE analysis. Marker proteins (Bio-Rad low molecular weight standards) were phosphorylase B (92,500), bovine serum albumin (66,200), ovalbumin (45,000), carbonic anhydrase (31,000), soybean trypsin inhibitor (21,500), and lysozyme (14,400).

Preliminary data suggest that the polymerase has a molecular weight of about 86,000–90,000 daltons, not 62,000–63,000 daltons reported in the literature (e.g., by Kaledin et al.).

The polymerase was incubated in 50 µl of a mixture containing either 25 mM Tris-HCl pH 6.4 or pH 8.0, and 0.1 M KCl, 10 mM $MgCl_2$, 1 mM 2-mercaptoethanol, 10 nmoles each of dGTP, dATP, and TTP, and 0.5 µCi ($^3$H) dCTP, 8 µg "activated" calf thymus DNA, and 0.5–5 units of the polymerase. "Activated" DNA is a native preparation of DNA after partial hydrolysis with DNase I until 5% of the DNA was transferred to the acid-soluble fraction. The reaction was conducted at 70° C. for 30 minutes, and stopped by adding 50 µl of a saturated aqueous solution of sodium pyrophosphate containing 0.125 M EDTA-$Na_2$. Samples were processed and activity was determined as described by Kaledin et al., supra.

The results showed that at pH 6.4 the polymerase was more than one-half as active as a pH 8.0. In contrast, Kaledin et al. found that at pH about 7.0, the enzyme therein had 8% of the activity at pH 8.3. Therefore, the pH profile for the thermostable enzyme herein is broader than that for the Kaledin et al. enzyme.

Finally, when only one or more nucleotide triphosphates were eliminated from a DNA polymerase assay reaction mixture, very little, if any, activity was observed using the enzyme herein, and the activity was consistent with the expected value, and with an enzyme exhibiting high fidelity. In contrast, the activity observed using the Kaledin et al. (supra) enzyme is not consistent with the expected value, and suggests misincorporation of nucleotide triphosphate(s).

D. Amplification Reaction

One microgram of the genomic DNA described above was diluted in an initial 100 μl aqueous reaction volume containing 25 mM Tris·HCl buffer (pH 8.0), 50 mM KCl, 10 mM MgCl$_2$, 5 mM dithiothreitol, 200 μg/ml gelatin, 1 μM of primer PC03, 1 μM of primer PC04, 1.5 mM dATP, 1.5 mM dCTP, 1.5 mM dGTP and 1.5 mM TTP. The sample was heated for 10 minutes at 98° C. to denature the genomic DNA, then cooled to room temperature. Four microliters of the polymerase from *Thermus aquaticus* was added to the reaction mixture and overlaid with a 100 μl mineral oil cap. The sample was then placed in the aluminum heating block of the liquid handling and heating instrument described in now abandoned Ser. No. 833,368 filed Feb. 25, 1986, the disclosure of which is incorporated herein by reference.

The DNA sample underwent 20 cycles of amplification in the machine, repeating the following program cycle:

1) heating from 37° C. to 98° C. in heating block over a period of 2.5 minutes; and 2) cooling from 98° C. to 37° C. over a period of three minutes to allow the primers and DNA to anneal.

After the last cycle, the sample was incubated for an additional 10 minutes at 55° C. to complete the final extension reaction.

E. Synthesis and Phosphorylation of Oligodeoxyribonucleotide Probes

A labeled DNA probe, designated RS24, of the following sequence was prepared:

```
                                                (RS24)
5'-*CCCACAGGGCAGTAACGGCAGACTTCTCCTCAGGAGTCAG-3'
``` where * indicates the label. This probe is 40 bases long, spans the fourth through seventeenth codons of the gene, and is complementary to the normal β-globin allele (β$^A$). The schematic diagram of primers and probes is given below:

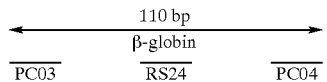

This probe was synthesized according to the procedures described in Section I of Example I. The probe was labeled by contacting 20 pmole thereof with 4 units of T4 polynucleotide kinase (New England Biolabs) and about 40 pmole γ-$^{32}$ P-ATP (New England Nuclear, about 7000 Ci/mmole) in a 40 μl reaction volume containing 70 mM Tris buffer (pH 7.6), 10 mM MgCl$_2$, 1.5 mM spermine, and 10 mM dithiothreitol for 60 minutes at 37° C. The total volume was then adjusted to 100 μl with 25 mM EDTA and the probe purified according to the procedure of Maniatis et al., *Molecular Cloning* (1982), 466–467 over a 1 ml Bio Gel P-4 (BioRad) spin dialysis column equilibrated with Tris-EDTA (TE) buffer (10 mM Tris buffer, 0.1 mM EDTA, pH 8.0). TCA precipitation of the reaction product indicated that for RS24 the specific activity was 4.3 μCi/pmole and the final concentration was 0.118 pmole/μl.

F. Dot Blot Hybridizations

Four microliters of the amplified sample from Section IV and 5.6 μl of appropriate dilutions of β-globin plasmid DNA calculated to represent amplification efficiencies of 70, 75, 80, 85, 90, 95 and 100% were diluted with 200 μl 0.4 N NaOH, 25 mM EDTA and spotted onto a Genatran 45 (Plasco) nylon filter by first wetting the filter with water, placing it in a Bio-Dot (Bio-Rad, Richmond, Calif.) apparatus for preparing dot blots which holds the filters in place, applying the samples, and rinsing each well with 0.1 ml of 20 x SSPE (3.6 M NaCl, 200 mM NaH$_2$PO$_4$, 20 mM EDTA), as disclosed by Reed and Mann, *Nucleic Acids Research*, 13, 7202–7221 (1985). The filters were then removed, rinsed in 20 x SSPE, and baked for 30 minutes at 80° C. in a vacuum oven.

After baking, each filter was the contacted with 16 ml of a hybridization solution consisting of 3 x SSPE, 5 x Denhardt's solution (1 x=0.02% polyvinylpyrrolidone, 0.02% Ficoll, 0.02% bovine serum albumin,, 0.2 mM Tris, 0.2 mM EDTA, pH 8.0), 0.5% SDS and 30% formamide, and incubated for two hours at 42° C. Then 2 pmole of probe RS24 was added to the hybridization solution and the filter was incubated for two minutes at 42° C.

Finally, each hybridized filter was washed twice with 100 ml of 2 x SSPE and 0.1% SDS for 10 minutes at room temperature. Then the filters were treated once with 100 ml of 2 x SSPE, 0.1% SDS at 60° C. for 10 minutes.

Each filter was then autoradiographed, with the signal readily apparent after two hours.

Discussion of Autoradiogram

The autoradiogram of the dot blots was analyzed after two hours and compared in intensity to standard serial dilution β-globin reconstructions prepared with HaeIII/MaeI-digested pBR:β$^A$, where β$^A$ is the wild-type allele, as described in Saiki et al., *Science*, supra. Analysis of the reaction product indicated that the overall amplification efficiency was about 95%, corresponding to a 630,000-fold increase in the β-globin target sequence.

EXAMPLE II

A. Amplification Reaction

Two 1 μg samples of genomic DNA extracted from the Molt 4 cell line as described in Example I were each diluted in a 100 μl reaction volume containing 50 mM KCl, 25 mM Tris·HCl buffer pH 8.0, 10 mM MgCl$_2$, 1 μM of primer PC03, 1 μM of primer PC04, 200 μg/ml gelatin, 10% dimethylsulfoxide (by volume), and 1.5 mM each of dATP, dCTP, dGTP and TTP. After this mixture was heated for 10 minutes at 98° C. to denature the genomic DNA, the samples were cooled to room temperature and 4 μl of the polymerase from *Thermus aquaticus* described in Example I was added to each sample. The samples were overlaid with mineral oil to prevent condensation and evaporative loss.

One of the samples was placed in the heating block of the machine described in Example I and subjected to 25 cycles of amplification, repeating the following program cycle:

(1) heating from 37 to 93° C. over a period of 2.5 minutes;

(2) cooling from 93° C. to 37° C. over a period of three minutes to allow the primers and DNA to anneal; and (3) maintaining at 37° C. for two minutes.

After the last cycle the sample was incubated for an additional 10 minutes at 60° C. to complete the final extension reaction.

The second sample was placed in the heat-conducting container of the machine, described in more detail in EP 236, 069, supra. The heat-conducting container is attached to Peltier heat pumps which adjust the temperature upwards of downwards and a microprocessor controller to control automatically the amplification sequence, the temperature levels, the temperature ramping and the timing of the temperature.

The second sample was subjected to 25 cycles of amplification, repeating the following program cycle:

(1) heating from 37 to 95° C. over a period of three minutes;

(2) maintaining at 95° C. for 0.5 minutes to allow denaturation to occur;

(3) cooling from 95 to 37° C. over a period of one minutes; and (4) maintaining at 37° C. for one minute.

B. Analysis

Two tests were done for analysis, a dot blot and an agarose gel analysis.

For the dot blot analysis, a labeled DNA probe, designated RS18, of the following sequence was prepared.

```
5'-*CTCCTGAGGAGAAGTCTGC-3'        (RS18)
``` where * indicates the label. This probe is 19 bases long, spans the fourth through seventeenth codons of the gene, and is complementary to the normal β-globin allele (β^A). The schematic diagram of primers and probes is given below:

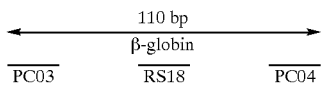

This probe was synthesized according to the procedures described in Section I of Example I. The probe was labeled by contacting 10 pmole thereof with 4 units of T4 polynucleotide kinase (New England Biolabs) and about 40 pmole $\gamma^{-32}$P-ATP (New England Nuclear, about 7000 Ci/mmole in a 40 µl reaction volume containing 70 mM Tris·HCl buffer (pH 7.6), 10 mM MgCl$_2$, 1.5 mM spermine and 10 mM dithiothreitol for 60 minutes at 37° C. The total volume was then adjusted to 100 µl with 25 mM EDTA and purified according to the procedure of Maniatis et al., supra, p. 466–467 over a 1 ml Bio Gel P-4 (BioRad) spin dialysis column equilibrated with Tris-EDTA (TE) buffer (10 mM Tris·HCl buffer, 0.1 mM EDTA, pH 8.0). TCA precipitation of the reaction product indicated that for RS18 the specific activity was 4.6 µCi/pmole and the final concentration was 0.114 pmole/µl.

Five microliters of the amplified sample from Section I and of a sample amplified as described above except using the Klenow fragment of E. coli DNA Polymerase I instead of the thermostable enzyme were diluted with 195 µl 0.4 N NaOH, 25 mM EDTA and spotted onto two replicate Genatran 45 (Plasco) nylon filters by first wetting the filters with water, placing them in a Bio-Dot (Bio-Rad, Richmond, Calif.) apparatus for preparing dot blots which hold the filters in place, applying the samples, and rinsing each well with 0.4 ml of 20 x SSPE (3.6 M NaCl, 200 mM NaH$_2$PO$_4$, 20 mM EDTA), as disclosed by Reed and Mann, supra. The filters were then removed, rinsed in 20 x SSPE, and baked for 30 minutes at 80° C. in a vacuum oven.

After baking, each filter was then contacted with 6 ml of a hybridization solution consisting of 5 x SSPE, 5 x Denhardt's solution (1 x=0.02% polyvinylpyrrolidone, 0.02% Ficoll, 0.02% bovine serum albumin, 0.2 mM Tris, 0.2 mM EDTA, pH 8.0) and 0.5% SDS, and incubated for 60 minutes at 55° C. Then 5 µl of probe RS18 was added to the hybridization solution and the filter was incubated for 60 minutes at 55° C.

Finally, each hybridized filter was washed twice with 100 ml of 2 x SSPE and 0.1% SDS for 10 minutes at room temperature. Then the filters were treated twice more with 100 ml of 5 x SSPE, 0.1% SDS at 60° C. for 1) one minutes and 2) three minutes, respectively.

Each filter was then autoradiographed, with the signal readily apparent after 90 minutes.

In the agarose gel analysis, 5 µl each amplification reaction was loaded onto 4% NuSieve/0.5% agarose gel in 1 x TBE buffer (0.089 M Tris, 0.089 M boric acid, and 2 mM EDTA) and electrophoresed for 60 minutes at 100 V. After staining with ethidium bromide, DNA was visualized by UV fluorescence.

The results show that the machines used in Example I and this example were equally effective in amplifying the DNA, showing discrete high-intensity 110-base pair bonds of similar intensity, corresponding to the desired sequence, as well as a few other discrete bands of much lower intensity. In contrast, the amplification method as described in Example I of now abandoned Ser. No. 839,331 filed Mar. 13, 1986, supra, which involves reagent transfer after each cycle using the Klenow fragment of E. coli Polymerase I, gave a DNA smear resulting from the non-specific amplification of many unrelated DNA sequences.

It is expected that similar improvements in amplification and detection would be achieved in evaluating HLA-DQ, DR and DP regions.

If in the above experiments the amplification reaction buffer contains 2 mM MgCl$_2$ instead of 10 mM MgCl$_2$ and 150–200 µM of each nucleotide rather than 1.5 mM of each, and if the lower temperature of 37° C. is raised to 45–58° C. during amplification, better specificity and efficiency of amplification occurs. Also, DMSO was found not necessary or preferred for amplification.

EXAMPLE III

Amplification and Cloning

For amplification of a 119-base pair fragment on the human β-globin gene, a total of 1 microgram each of human genomic DNA isolated from the Molt 4 cell line or from the GM2064 cell line (representing a homozygous deletion of the β- and δ-hemoglobin region and available from the Human Genetic Mutant Cell Depository, Camden, N.J.) as described above was amplified in a 100µl reaction volume containing 50 mM KCl, 25 mM Tris·HCl ph 8, 10 mM MgCl$_2$, 200 µg/ml gelatin, 5 mM 2-mercaptoethanol, 1.5 mM each of dATP, dCTP, TTP, and dGTP, and 1 µM of each of the following primers:

```
5'-CTTCTGcagCAACTGTGTTCACTAGC-3'      (GH18)

5'-CACaAgCTTCATCCACGTTCACC-3'         (GH19)
``` where lower case letter denote mismatches from wild-type sequence to create restriction enzyme sites. GH18 is a 26-base oligonucleotide complementary to the negative strand and contains an internal PstI site. GH19 is a 23-base oligonucleotide complementary to the plus strand and contains an internal HindIII recognition sequence. These primers were selected by first screening the regions of the gene for homology to the PstI and HindIII restriction sites. The primers were then prepared as described in Example I.

The above reaction mixtures were heated for 10 minutes at 95° C. and then cooled to room temperature. A total of 4 µl of the polymerase described in Example I was added to each reaction mixture, and then each mixture was overlayed with mineral oil. The reaction mixtures were subjected to 30 cycles of amplification with the following program:

2.5 min. ramp, 37 to 98° C.

3 min. ramp, 98 to 37° C.

2 min. soak, 37° C.

After the last cycle, the reaction mixtures were incubated for 20 minutes at 65° C. to complete the final extension. The mineral oil was extracted with chloroform and the mixtures were stored at −20° C.

A total of 10 µl of the amplified product was digested with 0.5 µg M13mp10 cloning vector, which is publicly available from Boehringer-Mannheim, in a 50 µl volume containing 50 mM NaCl, 10 mM Tris·HCl, pH 7.8, 10 mM MgCl$_2$, 20 units PstI and 26 units HindIII for 90 minutes at 37° C. The reaction was stopped by freezing at −20° C. The volume was adjusted to 110 μl with TE buffer and loaded (100 μl) onto a 1 ml BioGel P-4 spin dialysis column. One 0.1 ml fraction was collected and ethanol precipitated.

(At this point it was discovered that there was β-globin amplification product in the GM2064 sample. Subsequent experiments traced the source of contamination to the primers, either GH18 or GH19. Because no other source of primers was available, the experiment was continued with the understanding that some cloned sequences would be derived from the contaminating DNA in the primers.)

The ethanol pellet was resuspended in 15 μl water, then adjusted to 20 μl volume containing 50 mM Tris·HCl, ph 7.8, 10 mM MgCl$_2$, 0.5 mM ATP, 10 mM dithiothreitol, and 400 units ligase. This mixture was incubated for three hours at 16° C.

Ten microliters of ligation reaction mixture containing Molt 4 DNA was transformed into *E. coli* strain JM103 competent cells, which are publicly available from BRL in Bethesda, Md. The procedure followed for preparing the transformed strain is described in Messing, J. (1981) *Third Cleveland Symposium of Macromolecules:Recombinant DNA*, ed. A. Walton, Elsevier, Amsterdam, 143–163. A total of 651 colorless plaques (and 0 blue plaques) were obtained. Of these, 119 had a (+)-strand insert (18%) and 19 had a (−)-strand insert (3%). This is an increase of almost 20-fold over the percentage of β-globin positive plaques among the primer-positive plaques from the amplification technique using Klenow fragment of *E. coli* Polymerase I, where the reaction proceeded for two minutes at 25° C., after which the steps of heating to 100° C. for two minutes, cooling, adding Klenow fragment, and reacting were repeated nine times. These results confirm the improved specificity of the amplification reaction employing the thermostable enzyme herein.

In a later cloning experiment with GM2064 and the contaminated primers, 43 out of 510 colorless plaques (8%) had the (+)-strand insert. This suggests that approximately one-half of the 119 clones from Molt 4 contain the contaminant sequence.

Ten of the (+)-strand clones from Molt 4 were sequenced. Five were normal wild-type sequence and five had a single C to T mutation in the third position of the second codon of the gene (CAC to CAT). Four of the contaminant clones from GM2064 were sequenced and all four were normal.

Restriction site-modified primers may also be used to amplify and clone and partially sequence the human N-ras oncogene and to clone base pair segments of the HLA DQ-α, DQ-β and DR-β genes using the above technique.

Again, if the concentrations of MgCl$_2$ and nucleotides are reduced to 2 mM and 150–200 μM, respectively, and the minimum cycling temperature is increased from 37° C. to 45–58° C., the specificity and efficiency of the amplification reaction can be increased.

EXAMPLE IV

Gene Retrieval

A. Identification of a DNA Sequence Probe for the Taq Polymerase Gene

A specific DNA sequence probe for the Taq pol gene was obtained following immunological screening of a λgt11 expression library. *T. aquaticus* DNA was digested to completion with AluI, ligated with EcoRI 12-mer linkers (CCGGAATTCCGG, New England Biolabs), digested with EcoRI and ligated with dephosphorylated, EcoRI-digested λgt11 DNA (Promega Biotech). The ligated DNA was packaged (Gigapack Plus, Stratagene) and transfected into *E. coli* K-12 strain Y1090 (provided by R. Young).

The initial library of 2×10$^5$ plaques was screened (Young, R. A., and R. W. Davis (1983) *Science*, 222:778–782) with a 1:2000 dilution of a rabbit polyclonal antiserum raised to purified Taq polymerase (see Examples I and XIII). Candidate plaques were replated at limiting dilution and rescreened until homogeneous (~3 cycles). Phage were purified from candidate plaques which failed to react with preimmune serum and reacted with immune serum.

Candidate phage were used to lysogenize *E. coli* K-12 strain Y1089 (R. Young). Lysogens were screened for the production of an IPTG inducible fusion protein (large than β-galactosidase) which reacted with the Taq polymerase antiserum. Solid phase, size-fractionated fusion proteins were used to affinity purify epitope-specific antibodies from the total polyclonal antiserum (Goldstein, L. S. B., et al. (1986) *J. Cell Biol.* 102:2076–2087).

The "fished", epitope-selected antibodies were used, in turn, in a Western analysis to identify which λgt11 phage candidates encoded DNA sequences uniquely specified to Taq polymerase. One λgt11 phage candidate, designated λgt:1, specifically selected antibodies from the total rabbit polyclonal Taq polymerase antiserum which uniquely reacted with both purified Taq polymerase and crude extract fractions containing Taq polymerase. This phage, λgt:1, was used for further study.

The ~115 bp EcoRI-adapted AluI fragment of *Thermus aquaticus* DNA was labeled (Maniatis et al., supra) to generate a Taq polymerase-specific probe. The probe was used in Southern analyses and to screen a *T. aquaticus* DNA random genomic library.

B. Construction and Screening of a *Thermus aquaticus* Random Genomic Library

Lambda phage Charon 35 (Wilhelmine, A. M. et al, supra) was annealed and ligated via its cohesive ends, digested to completion with BamHI, and the annealed arms were purified from the "stuffer" fragments of potassium acetate density gradient ultracentrifugation (Maniatis, et al., supra) *T. aquaticus* DNA was partially digested with Sau3A and the 15–20 kb size fraction purified by sucrose density gradient ultracentrifugation. The random genomic library was constructed by ligating the target and vector DNA fragments at a 1:1 molar ratio. The DNA was packaged and transfected into *E. coli* K-12 strains LE392 or K802. A library of >20,000 initial phage containing >99% recombinants was amplified on *E. coli* K-12 strain LE392.

The CH35 Taq genomic phage library was screened (Maniatis et al., supra) with the radiolabeled EcoRI insert of λgt11:1. Specifically hybridizing candidate phage plaques were purified and further analyzed. One phage, designated Ch35::4-2, released ≧four *T. aquaticus* DNA fragments upon digestion with HindIII (~8.0, 4.5, 0.8, 0.58 kb)

The four HindIII *T. aquaticus* DNA fragments were ligated with HindIII digested plasmid BSM13$^+$ (3.2 kb, Vector Cloning Systems, San Diego) and individually cloned following transformation of *E. coli* K-12 strain DG98.

The ~8.0 kb HindIII DNA fragment from CH35::4-2 was isolated in plasmid pFC82 (11.2 kb), while the 4.5 kb HindIII DNA fragment from CH35::4-2 was isolated in plasmid pFC83 (7.7 kb).

*E. coli* strain DG98 harboring pFC82 was shown to contain a thermostable, high temperature DNA polymerase activity (Table 1). In addition, these cells synthesize a new ~60 kd molecular weight polypeptide which is immunologically related to Taq DNA polymerase.

The Taq polymerase coding region of the 8.0 kb HindIII DNA fragment was further localized to the lac-promoter proximal 2.68 kb HindIII to Asp718 portion of the 8.0 kb HindIII fragment. This region was subcloned to yield plasmid pFC85 (6.0 kb). Upon induction with IPTG, *E. coli* DG98 cells harboring plasmid pFC85 synthesize up to 100-fold more thermostable, Taq polymerase-related activity (Table 1) than the original parent clone (pFC82/DG98). While cells harboring pFC85 synthesize a significant amount of a thermostable DNA polymerase activity, only a portion of the Taq pol DNA sequence is translated, resulting in the accumulation of a ~60 kd Taq polymerase-related polypeptide.

TABLE 1

Expression of a Thermostable DNA Polymerase Activity in *E. coli*[#]

| Sample | Units*/ml | |
|---|---|---|
| | IPTG | +IPTG |
| BSM13/DG98 | — | 0.02 |
| pFC82/DG98 | 2.2 | 2.7 |
| pFC85/DG98 | 11.9 | 643.8 |

[#]Cells were grown to late log phase (+/− IPTG, 10 mM), harvested, sonicated, heated at 75° C. for 20 minutes, centrifuged and the clarified supernatant assayed at 70° C. for DNA polymerase activity.
*1 unit = 1 nMole dCTP incorporated in 30 minutes.

EXAMPLE V

Expression of Taq Polymerase

The thermostable gene of the present invention can be expressed in any of a variety of bacterial expression vectors including DG141 (ATCC 39588) and $P^P_L N_{RBS}ATG$, vectors disclosed in U.S. Pat. No. 4,711,845, the disclosure of which is incorporated herein by reference. Both of these host vectors are pBR322 derivatives that have either a sequence containing a tryptophan promoter-operator and ribosome binding site with an operably linked ATG start codon (DG141) or a sequence containing the lambda $P_L$ promoter and gene N ribosome binding site operably linked to an ATG start codon ($P^P_L N_{RBS}ATG$). Either one of these host vectors may be restricted with SacI, and blunt ended with Klenow or S1 nuclease to construct a convenient restriction site for subsequent insertion of the Taq polymerase gene.

The full-length Taq polymerase gene was constructed from the DNA insert fragments subcloned into plasmids pFC83 and pFC85 as follows. Vector BSM13[+] (commercially available from Vector Cloning Systems, San Diego, Calif.) was digested at the unique HindIII site, repaired with Klenow and dNTPs, and ligated with T4 DNA ligase to a BglII octanucleotide linker, 5'-CAGATCTG-3' (New England Biolabs), and transformed into *E. coli* strain DG98. Plasmids were isolated from Amp[R] lacZα[+] transformants. One of the clones was digested with BglII and Asp718 restriction enzymes, and the large vector fragment purified by gel electrophoresis.

Next, plasmid pFC83 was digested with BglII and HindIII and the ~730 base pair fragment was isolated. Plasmid pFC85 was digested with HindIII and Asp718 and the ~2.68 kb fragment isolated and joined in a three-piece ligation to the ~730 base pair BglII-HindIII fragment from pFC83 and the BglII-Asp718 vector fragment of BSM13[+]. This ligation mixture was used to transform *E. coli* strain DG98 (ATCC 39,768 deposited Jul. 13, 1984) from which Amp[R] colonies were selected and an ~6.58 kilobase plasmid (pLSG1) was isolated. Isopropyl-β-D-thiogalactoside (IPTG)-induced DG98 cells harboring pLSG1 synthesized Taq DNA polymerase indistinguishable in size from the native enzyme isolated from *T. aquaticus*.

Oligonucleotide-directed mutagenesis (see Zoller and Smith, *Nuc. Acids Res.* (1982) 10:6487–6500) was used to simultaneously 1) introduce an SphI site within codons 3 to 5 of the Taq DNA polymerase gene sequence (see FIG. 1, nt 8–13), 2) increase the A/T content of four of the first seven codons without effecting a change in the encoded amino acids (within codons 2–7 in FIG. 1), 3) delete 170 nucleotides of the lacZ DNA and *T. aquaticus* DNA 5' to the DNA polymerase gene initiation codon.

Bacteriophage R408 (Russel, M., et al., *Gene*, (1986) 45:333–338) was used to infect pLSG1/DG98 cells and direct the synthesis of the single-stranded DNA (ss) form (plus strand) of pLSG1. Purified pLSG1 ssDNA was annealed with purified PvuII-digested BSM13[+] BglII vector fragments and the 47-mer mutagenic oligonucleotide DG26 (5'-CCCTTGGGCTCAAAAAGTGGAAGCATGCCT-CTCATAGCTGTTTCCTG). Following extension with *E. coli* DNA polymerase I Klenow fragment, transformation of DG98 cells, and selection Amp[R] transformants, the colonies were screened with 5' $^{32}$P-labeled DG26. Hybridizing candidates were screened for loss of the BglII restriction site, deletion of approximately 170 base pairs of lacZ:*T. aquaticus* DNA, and introduction of a unique SphI site. One candidate, designated pLSG2, was sequenced and shown to encode the desired sequence.

pLSG1 sequence:

```
  S.D.                     47bp  BglII   105bp
CAGGAAACAGCT ATG [ACC ATG ..... AGATCT .....

...AAC ATG] AGG GGG ATG CTG CCC CTC TTT
``` pLSG2 sequence:

```
  S.D.                   SphI
CAGGAAACAGCTATG AGA GGC ATG CTT CCA CTT TTT
```

Oligonucleotide-directed mutagenesis was used to introduce a unique BglII site in plasmid pLSG2 immediately following the TGA stop codon for the Taq polymerase gene (following nucleotide 2499 in FIG. 1). As above, bacteriophage R408 was used to generate the single-stranded (plus) form of plasmid pLSG2. Purified pLSG2 ssDNA was annealed with purified PvuII-digested BSM13[+] BglII vector fragment and the 29-mer mutagenic oligonucleotide SC107 (5'-GCATGGGGTGGTAGATCTCACTCCTTGGC). Following extension with Klenow fragment (50 mM each dNTP), transformation of DG98 cells and selection for Amp[R] transformants, colonies were screened with 5' $^{32}$P-labeled SC107. Hybridizing candidates were screened for acquisition of a unique BglII site. One candidate, designated pSYC1578, was sequenced and shown to contain the desired sequence.

pLSG2 sequence:

```
...GCC AAG GAG TGA TAC CAC CCC ATG C...
``` pSYC1578 sequence:

```
                Bg:II
...GCC AAG GAG TGA GATC TAC CAC CCC ATG C...
```

EXAMPLE VI

Construction of Expression Vectors pDG160 and pDG161

The Amp[R] or Tet[R] λ$P_L$ promoter, gene N ribosome binding site, polylinker, BT cry PRE (BT) (positive retroregulatory element, described in U.S. Pat. No. 4,666,848, issued May 19, 1987), in a ColE1 $cop^{ts}$ vector were constructed from previously described plasmids and the duplex synthetic oligonucleotide linker DG31 and DG32. The DG31/32 duplex linker encodes a 5' HindIII cohesive end followed by SacI, NcoI, KpnI/Asp718, XmaI/SmaI recognition sites and a 3' BamHI cohesive end.

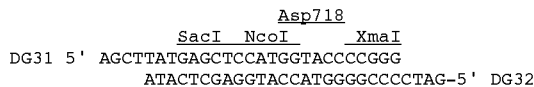

```
                    Asp718
         SacI  NcoI         XmaI
DG31 5' AGCTTATGAGCTCCATGGTACCCCGGG
             ATACTCGAGGTACCATGGGGCCCCTAG-5' DG32
```

A. Construction of $Amp^R$ Plasmid pDG160

Plasmid pFC54.t, a 5.96 kb plasmid described in U.S. Pat. No. 4,666,848, supra, was digested with HindIII and BamHI and the isolated vector fragment was ligated with a 5-fold molar excess of nonphosphorylated and annealed DG31/32 duplex. Following ligation, the DNA was digested with XbaI (to inactivate the parent vector IL-2 DNA fragment) and used to transform E. coli K12 strain DG116 to ampicillin resistance. Colonies were screened for loss of the des-ala-ser[125] IL-2 mutein sequence and acquisition of the DG31/32 polylinker sequence by restriction enzyme digester. The polylinker region in one candidate, designated pDG160, was sequenced and shown to encode the desired polylinker DNA sequence.

B. Construction of $Tet^R$ Plasmid pDG161

Plasmid pAW740CHB (ATCC 67,605), the source of a modified tetracycline resistance gene wherein the BamHI and HindIII restriction sites were eliminated, and which contains the $\lambda P_L$ promoter, gene N ribosome binding site, cry PRE in a ColE1 $cop^{ts}$ vector, was digested to completion with HindIII and BamHI and the 4.19 kb vector fragment purified by agarose gel electrophoresis. The purified vector DNA fragment was ligated with a 5-fold molar excess of nonphosphorylated annealed DG31/32 duplex. E. coli K12 strain DG116 was transformed with a portion of the DNA, and $Tet^R$ colonies screened for presence of 4.2 kb plasmids. Several candidates were further screened by restriction enzyme digestion and the polylinker region sequenced by the Sanger method. One of the candidates with the desired sequence was designated pDG161.

EXAMPLE VII

A. Construction of an $Amp^R$ $P_L$ Promoter, Gene N Ribosome Binding Site, ($N_{RBS}$) Taq Polymerase (832) BT cry PRE, $cop^{ts}$ Expression Vector To express the full-length (832 amino acid) mutated Taq polymerase sequence encoded by plasmid pSYC1578 under the control of the $\lambda P_L$ promoter and gene N ribosome binding site, we used plasmids pSYC1578 and pFC54.t. Plasmid pSYC1578 was digested with SphI and BglII and the resulting approximate 2.5 kb Taq polymerase gene fragment purified by agarose gel electrophoresis and electroelution. Plasmid pFC54.t was digested to completion with HindIII and BamHI and the vector fragment purified by agarose gel electrophoresis. The synthetic oligonucleotides DG27 (5'-AGCTTATGAGAGGCATG) and DG28 (5'-CCTCTCATA) were synthesized and annealed. Purified pFC54.t fragment (0.085 pmoles), purified Taq polymerase gene fragment (0.25 pmoles) were annealed nonphosphorylated DG27/28 duplex adaptor (0.48 pmoles) were combined in 30 μl and ligated at 14° C. A portion of the ligated DNA was heated to 75° C. (15 minutes) to inactivate the DNA ligase in the samples and treated with XbaI to linearize (inactivate) any IL-2 mutein containing ligation products. The ligated and digested DNA (approximately 100 ng) was used to transform E. coli K12 strain DG116 to ampicillin resistance. $Amp^R$ colonies were screened for the presence of an approximate 8 kb plasmid which yielded the expected digestion produces with HindIII (621 bp+7,410 bp), EcoRI (3,250 bp+4,781 bp) and SphI (8,031 bp), Asp718 (8,031 bp), BamHI (8,031 bp) and PvuII (4,090 bp+3,477 bp+464 bp). Several candidates were subjected to DNA sequence analysis at the 5' $\lambda P_L$:TaqPol junction and the 3' TaqPol:BT junction. One of the candidates was also screened with an anti-Taq polymerase antibody for the synthesis of an approximate 90 kd immunoreactive antigen. Single colonies were transferred from a 30° C. culture plate to a 41° C. culture plate for two hours. The colonies were scraped with a toothpick from both the 30° C. and 41° C. plates, boiled in SDS loading buffer, subjected to SDS-PAGE electrophoresis and the separated proteins transferred to a nitrocellulose membrane. The membranes were probed with a 1:6,000 dilution of a polyclonal anti-Taq antibody and developed with a goat anti-rabbit HRP conjugate. All of the candidates tested showed evidence of temperature inducible approximate 90 kd Taq polymerase-related protein. One of the several plasmid candidates which directed the synthesis of Taq polymerase in E. coli and contained the expected DNA sequence was designated pLSG5.

B. Construction of a $Tet^R$ $P_L$ Promoter, Gene N Ribosome Binding Site, Taq Polymerase (832) BT cry PRE $cop^{ts}$ Expression Vector To express the full length (832 amino acid) mutated Taq polymerase sequence encoded by plasmid pSYC1578 under control of the $\lambda P_L$ promoter and gene N ribosome binding site in a $Tet^R$ vector, we used plasmids pSYC1578 and pAW740CHB. Plasmid pSYC1578 was digested with SphI and BglII and the resulting approximate 2.5 kb Taq polymerase gene fragment was purified by agarose gel electrophoresis and electroelution. Plasmid pAW740CHB was digested to completion with HindIII and BamHI and the resulting 4.19 kb vector fragment purified by agarose gel electrophoresis and electroelution. The synthetic oligonucleotides DG27 and DG28 (described previously) were annealed. Purified pAW740CHB vector fragment (0.12 pmoles) was ligated with purified Taq polymers gene fragment (0.24 pmoles) and annealed nonphosphorylated DG27/28 duplex adaptor (0.24 pmoles) in 30 μl at 14° C. A portion of the ligated DNA (100 ng) was used to transform E. coli K12 strain DG116 to tetracycline resistance. $Tet^R$ candidates were screened for the presence of an approximate 6.7 kb plasmid which yielded the expected digestion products with HindIII (621 bp+6,074 bp), EcoRI (3,445 bp+3,250 bp), Asp718 (6,695 bp), SphI (3,445 bp+3,250 bp), BamHI (6,695 bp) and PvuII (3,477 bp+2,754 bp+464 bp). Several candidates were subjected to DNA sequence analysis at the 5' $\lambda P_L$:TaqPol junction and the 3' TaqPol:BT junction. Candidates were also screened by single colony immunoblot as described above for the temperature inducible synthesis of Taq polymerase. One of the plasmid candidates which directed the synthesis of Taq polymerase in E. coli and contained the expected DNA sequence was designated pLSG6.

EXAMPLE VIII

Construction of a Met4 (∇3) 829 Amino Acid Form of Taq Polymerase

The predicted fourth codon of native Taq polymerase directs the incorporation of a methionine residue (see pLSG1 and pLSG2 5' sequences above). To obtain a further mutates form of a Taq polymerase gene that would direct the synthesis of an 829 amino acid primary translation product we used plasmids pSYC1578 and pDG161. Plasmid pSYC1578 was digested with SphI, treated with *E. coli* DNA polymerase I Klenow fragment in the presence of dGTP to remove the four-base 3' cohesive end and generate a CTT (leucine, 5th codon) blunt end. Following inactivation of the DNA polymerase and concentration of the sample, the DNA was digested with BglII and the approximate 2.5 kb Taq polymerase gene fragment purified by agarose gel electrophoresis and electroelution. Plasmid pDG161 was digested to completion with SacI, repaired with *E. coli* DNA polymerase I Klenow fragment in the presence of dGTP to remove the four base 3' cohesive end and generate an ATG terminated duplex blunt end. Following inactivation of the polymerase, the sample was digested with BamHI.

Digested pDG161 (0.146 pmole) and purified Taq polymerase fragment (0.295 pmole) were ligated at 30 $\mu$g/ml under sticky end conditions overnight. The partially ligated DNA sample (BamHI/BglII ends) was diluted to 15 $\mu$g/ml and ligated for five hours under blunt end conditions. The DNA ligase was inactivated (75° C., 10 minutes) and the sample digested with NcoI to linearize any ligation products containing the pDG161 polylinker sequence. Sixty nanograms of the ligated and digested DNA was used to transform *E. coli* K12 strain DG116 to tetracycline resistance. Tet$^R$ candidates were screened for the presence of an approximate 6.7 kb plasmid which yielded the expected digestion products when treated with HindIII (612 bp+6,074 bp), EcoRI (3,445 bp+3,241 bp) and SphI (6,686 bp). Colonies were screened as above by single colony immunoblot for the temperature inducible synthesis of an approximate 90 kd Taq polymerase-related polypeptide. One of the plasmids, designated pLSG7, that directed the synthesis of a Taq polymerase-related polypeptide was subjected to Sanger sequence determination at the 5' $\lambda$P$_L$ promoter:Taq polymerase junction and the 3' Taq polymerase:BT junction. Analysis of the DNA sequence at the 5' junction confirmed the restriction enzyme analysis (loss of one of the SphI sites and a 612 bp HindIII fragment, slightly smaller than the 621 bp HindIII fragment in pLSG6) and indicated the derivation of a plasmid encoding an 829 amino acid form of Taq polymerase.

EXAMPLE IX

Construction of Met289 ($\triangledown$289) 544 Amino Acid Form of Taq Polymerase During purification of native Taq polymerase (Example XIII) we obtained an altered form of Taq polymerase that catalyzed the template dependent incorporation of dNTP at 70° C. This altered form of Taq polymerase was immunologically related to the approximate 90 kb form described in Example XIII but was of lower molecular weight. Based on mobility, relative to BSA and ovalbumin following SDS-PAGE electrophoresis, the apparent molecular weight of this form is approximately 61 kd. This altered form of the enzyme is not present in carefully prepared crude extracts of *Thermus aquaticus* cells as determined by SDS-PAGE Western blot analysis or in situ DNA polymerase activity determination (Spanos, A., and Hubscher, U. (1983) *Meth. Enz.* 91:263–277) following SDS-PAGE gel electrophoresis. This form appears to be proteolytic artifact that may arise during sample handling. This lower molecular weight form was purified to homogeneity and subjected to N-terminal sequence determination on an ABI automated gas phase sequencer. Comparison of the obtained N-terminal sequence with the predicted amino acid sequence of the Taq polymerase gene (see FIG. 1) indicates this shorter form arose as a result of proteolytic cleavage between glu$_{289}$ and ser$_{290}$.

To obtain a further truncated form of a Taq polymerase gene that would direct the synthesis of a 544 amino acid primary translation product we used plasmids pFC54.t, pSYC1578 and the complementary synthetic oligonucleotides DG29 (5'-AGCTTATGTCTCCAAAAGCT) and DG30 (5'-AGCTTTTGGAGACATA). Plasmid pFC54.t was digested to completion with HindIII and BamHI. Plasmid pSYC1578 was digest with BstXI and treated with *E. coli* DNA polymerase I Klenow fragment in the presence of all 4 dNTPs to remove the 4 nucleotide 3' cohesive end and generate a CTG-terminated duplex blunt end encoding leu$_{294}$ in the Taq polymerase sequence (see pLSG1, nucleotide 880). The DNA sample was digested to completion with BglII and the approximate 1.6 kb BstXI (repaired)/BGlII Taq DNA fragment was purified by agarose gel electrophoresis and electroelution. The pFC54.t plasmid digest (0.1 pmole) was ligated with the Taq polymerase gene fragment (0.3 pmole) and annealed nonphosphorylated DG29/DG30 duplex adaptor (0.5 pmole) under sticky ligase conditions at 30 $\mu$g/ml, 15° C. overnight. The DNA was diluted to approximately 10 microgram per ml and ligation continued under blunt end conditions. The ligated DNA sample was digested with XbaI to linearize (inactivate) any IL-2 mutein-encoding ligation products. 80 nanograms of the ligated and digested DNA was used to transform *E. coli* K12 strain DG116 to ampicillin resistance. Amp$^R$ cogitates were screened for the presence of an approximate 7.17 kb plasmid which yielded the expected digestion products with EcoRI (4,781 bp+2,386 bp), PstI (4,138 bp+3,029 bp), ApaI (7,167 bp) and HindIII/PstI (3,400 bp+3,029 bp+738 bp). *E. coli* colonies harboring candidate plasmids were screened as above by single colony immunoblot for the temperature-inducible synthesis of an approximate 61 kd Taq polymerase related polypeptide. In addition, candidate plasmids were subjected to DNA sequence determination at the 5' $\lambda$P$_L$ promoter:Taq DNA junction and the 3' Taq DNA:BT cry PRE junction. One of the plasmids encoding the intended DNA sequence and directing the synthesis of a temperature-inducible 61 kd Taq polymerase related polypeptide was designated pLSG8.

Yet another truncated Taq polymerase gene contained within the ~2.68 kb HindIII-Asp718 fragment of plasmid pFC85 can be expressed using, for example, plasmid pP$_L$N$_{RBS}$ATG, by operably linking the amino-terminal HindIII restriction site encoding the Taq pol gene to an ATG initiation codon. The product of this fusion upon expression will yield an ~70,000–72,000 dalton truncated polymerase.

This specific construction can be made by digesting plasmid pFC85 with HindIII and treating with Klenow fragment in the presence of dATP and dGTP. The resulting fragment is treated further with S1 nuclease to remove any single-stranded extensions and the resulting DNA digested with Asp718 and treated with Klenow fragment in the presence of all four dNTPs. The recovered fragment can be ligated using T4 DNA ligase to dephosphorylated plasmid pP$_L$N$_{RBS}$ATG, which had been digested with SacI and treated with Klenow fragment in the presence of dGTP to construct an ATG blunt end. This ligation mixture can then be used to transform *E. coli* DG116 and the transformants screened for production of Taq polymerase. Expression can be confirmed by Western immunoblot analysis and activity analysis.

EXAMPLE X

Construction of Amp$^R$ trp Promoter Operator, trpL Ribosome Binding Site, Taq Polymerase (832) BT cry PRE cop$^{ts}$ Expression Vector To substitute the *E. coli* trp operon promoter/operator and leader peptide ribosome binding site, we used plasmids pLSG5 and pFC52, pFC52 was the source of the trp promoter, cop^ts and ampicillin resistant determinants. However, plasmid pCS4, described in U.S. Pat. No. 4,711,845, supra, the disclosure of which is incorporated herein by reference, may be used to provide the identical fragment. Plasmid pLSG5 was digested to completion with SphI. The SphI was inactivated (70° C. 10 minutes) and the digested DNA was ligated overnight at 15° C. with an excess of annealed nonphosphorylated DG27/28 duplex adaptor (see above). The T4 DNA ligase was inactivated (70° C., 10 minutes) and the DNA digested to completion with MluI. The DNA sample was sequentially extracted with phenol and ether, ethanol precipitated and finally resuspended in 10 mM Tris chloride pH 8, 1 mM EDTA. Plasmid pFC52 (or pCS4) was digested to completion with MluI and extracted with phenol, ether and concentrated as above. The DNA sample was digested to completion with HindIII and the HindIII inactivated (75° C., 15 minutes). The pLSG5 and pFC52 samples were ligated overnight in equal molar ratio and at 30 μg/ml under sticky end conditions. The T4 ligase was inactivated (70° C., 10 minutes) and the ligated DNA was digested with SbaII to linearize (inactivate) any IL-2 encoding ligation products (from the pFC52 unwanted, 1.65 kb HindIII/MluI DNA fragment). $E.\ coli$ K12 strain DG116 was transformed to ampicillin resistance with 30 nanogram of the ligated DNA. $Amp^R$ colonies were screened for the presence of approximate 7.78 kb plasmids which yielded the expected digestion products with EcoRI (4,781 bp+3,002 bp), SphI (7,783 bp), HindIII (7,162 bp+621 bp), ClaI (7,783 bp) and ClaI/MluI (3,905 bp+3,878 bp). Candidate colonies were further screened for expression of an approximate 90 kd Taq polymerase related protein by single colony SDS-PAGE immunoblotting (as above). Plasmids from two the candidates showing the intended properties were transformed into $E.\ coli$ K12 strain KB2 (ATCC No. 53075).

By Western immunoblot, both plasmids in both hosts were shown to direct the synthesis of an approximate 90 kd Taq polymerase-related polypeptide upon trp limitation. By comassie straining of SDS-PAGE fractionated whole cell extract proteins, the trp promoter/Taq polymerase plasmids in $E.\ coli$ K12 strain KB2 direct the accumulation of significantly more Taq polymerase than in $E.\ coli$ K12 strain DG116. One of the plasmids was designated pLSG10.

EXAMPLE XI

Synthesis of Recombinant Taq DNA Polymerase Activity in $E.\ coli$ $E.\ coli$ K12 (DG116) strains harboring plasmids pDG160, or pLSG5, or pLSG6 were grown at 32° C. in Bonner-Vogel minimal salts media containing 0.5% glucose, 10 μg/ml thiamine, 0.25% (w/v) Difco casamino acids and ampicillin (100 μg/ml) or tetracycline (10 μg/ml) as appropriate. Cells were grown to $A_{600}$ of about 0.8 and shifted to 37° C. to simultaneously derepress the lambda $P_L$ promoter (inactivation of $cI_{857}$ repressor) and increase the copy number of the ColE1 $cop^{ts}$ plasmid vector. After six–nine hours of growth at 37° C. aliquots of the cells were harvested, the cells centrifuges and the pellets stored at −70° C.

Alternatively, $E.\ coli$ K12 strain KB2 harboring plasmid pLSG10 was grown for eight hours at 32° C. in Bonner-Vogel minimal salts media containing 0.5% glucose, 5 μg/ml tryptophan, 10 μ/ml thiamine, 0.25% Difco casamino acids and 100 μg/ml ampicillin to an $A_{600}$ of 3.0. Cells were harvested as above.

Cell pellets were resuspended to about 62.5 $A_{600}$/ml (~150–160 μg total protein/ml) in 50 mM Tris-Cl, pH 7.5, 1 mM EDTA, 2.4 mM PMSF and 0.5 μg/ml leupeptin and lysed by sonication. Aliquots of the sonicated extracts were subjected to SDS-PAGE and analyzed by Coomassie staining and Western immunoblotting with rabbit polyclonan anti-Taq polymerase antibody. In addition, portions of the extracts were assayed in a high temperature (74° C.) DNA polymerase assay (see Example XIII below).

Western immunoblotting showed significant induction and synthesis of an approximately 94 kd Taq DNA polymerase related polypeptide in induced strains harboring plasmids pLSG5, 6, and 10. Coomassie blue staining of SDS-PAGE-separated total cell protein revaled the presence of a new predominant protein at ~94 kd in these induced strains. Finally, high temperature activity assays confirmed the significant level of recombinant Taq DNA polymerase synthesis in these $E.\ coli$ strains (see table, below).

| Plasmid Host | Taq Pol Gene | Promoter | Uninduced (−) or Induced (+) | Units*/$OD_{600}$ |
| --- | --- | --- | --- | --- |
| pDG160/DG116 | − | $P_L$ | − or + | <1.0 |
| pLSG5/DG116 | + | $P_L$ | − | 23 |
| pLSG5/DG116 | + | $P_L$ | + | 308 |
| pLSG6/DG116 | + | $P_L$ | − | 5 |
| pLSG6/DG116 | + | $P_L$ | + | 170 |
| pLSG10/KB2 | + | Trp | + | 300 |

*1 unit = 10 nmole total nucleotide incorporated at 74° C./30 minutes.

EXAMPLE XII

Purification of Recombinant Taq DNA Polymerase $E.\ coli$ strain DG116 harboring plasmid pLSG5 was grown in a 10 L fermentor. The medium was 10 mM $(NH_4)_2SO_4$, 25 mM $KH_2PO_4$, 4 mM $Na_3$Citrate, 400 μM $FeCl_3$, 28 μM $ZnCl_2$, 34 μM $CoCl_2$, 33 μM $NaMoO_4$, 27 μM $CaCl_2$, 30 μM $CuCl_2$, and 32 μM $H_3BO_3$. The medium was adjusted to pH 6.5 with NaOH, ~15 mM, and sterilized. The following sterile components were added: 20 mg/l thiamine·HCl, 3 mM $MgSO_4$, 10 g/l glucose and 12.5 mg/l ampicillin. The pH was adjusted to 6.8 and held there using $NH_4OH$. Glucose was fed to the culture in conjunction with the alkali demand, to maintain a glucose concentration at 40% of air saturation, by automatic increases in rpm (35 to 1000) and airflow (2 to 5 l/min). Foaming was controlled on demand using polypropylene glycol.

The fermentor was inoculated with cells and grown to $A_{680}$=5.0 (14.25 hours). The temperature was raised to 37° C. to induce synthesis of recombinant Taq polymerase and growth continued for five hours to $A_{680}$ of 16.5.

Unless otherwise indicated, all purification steps were conducted at 4° C. Twenty grams (wet weight) of induced frozen $E.\ coli$ K12 strain DG116 harboring plasmid pLSG5 was thawed in 3 volumes of 50 mM Tris-Cl, pH 7.5, 1 mM EDTA, 3 mM PMSF, 0.65 μg/ml leupeptin and disrupted in a French Press at 20,000 psi. The lysate was adjusted to 5.5× cell volume with additional buffer and sonicated (4×30 seconds) to reduce viscosity (Fraction I). The crude total cell lysate was adjusted to 0.2 M $(NH_4)_2SO_4$ (26.43 g/l) and centrifuged for 15 minutes at 20,000× G. The supernatant (Fraction II) was heated to 75° C. (in a 100° C. water bath) and maintained at 72–75° C. for 15 minutes to denature $E.\ coli$ host proteins. The sample was rapidly cooled to 4° C. by swirling in an ice water bath. After 20 minutes at 0° C. the sample was centrifuged at 20,000× G. for 15 minutes to precipitate the denatured proteins. The supernatant (Fraction III) was applied at 4 ml/hr to a 6 ml Phenyl-Sepharose CL-4B (Pharmacia) column equilibrated with 50 mM Tris-Cl, pH 7.5, 1 mM EDTA (Buffer A) containing 0.2 M $(NH_4)_2SO_4$. The column was sequentially washed with 3–10 column volumes of a) the same buffer, b) Buffer A, c) Buffer A containing 20% ethylene glycol to remove nucleic acids and non-Taq polymerase proteins. Taq DNA polymerase activity was eluted with 60 ml linear gradient of 0–4 M urea in Buffer A containing 20% ethylene glycol. The active fractions (~2 M urea) were pooled (Fraction IV) and applied at 3 ml/hr to a 12 ml (1.5×6.0 cm) Heparin-Sepharose CL-6B (Pharmacia) column equilibrated in 50 mM Tris-Cl, pH 7.5, 0.1 mM EDTA, 0.2% Tween 20 (Buffer B) containing 0.1 M KCl. The column was washed with 2 column volumes of Buffer B containing 0.15 M KCl. The Taq polymerase was eluted with a 120 ml linear gradient of 0.15–0.65 M KCl in Buffer B. The Taq polymerase eluted as a single $A_{280}$ and activity peak at ~0.29 M KCl.

Purified recombinant and native Taq polymerase proteins comigrate following electrophoresis on SDS-PAGE and staining with Coomassie blue. The purified Taq polymerase proteins migrate slightly faster than purified Phosphorylase B (Pharmacia), consistent with a molecular weight predicted from the DNA sequence (of pLSG5) of 93,920 daltons.

The peak activity fractions were pooled and a portion subjected to N-terminal amino acid sequence determination on an Applied Biosystems gas phase sequencer. In contrast to native Taq polymerase which has a blocked amino terminus, the sequence of the purified recombinant Taq polymerase and the individual cycle yields were consistent with the sequence predicted for the amino terminus of the Taq polymerase protein encoded by plasmid pLSG5.

The recombinant Taq polymerase encoded by plasmid pLSG5 and purified as described could amplify a human "single copy" sequence. Using a low temperature limit of 55° C., extension temperature of 72° C., upper temperature limit of 94° C. and a 2–2.5 minute cycle time, comparable yields and efficiency were noted for native and recombinant Taq polymerase using 1–2 units/100 μl PCR.

EXAMPLE XIII

Purification

The thermostable polymerase may be purified directly from a culture of *Thermus aquaticus* following the example disclosed below or, alternatively, from a bacterial culture containing the recombinantly produced enzyme with only minor modifications necessary in the preparation of the crude extract.

After harvesting by centrifugation, 60 grams of cells were resuspended in 75 ml of a buffer consisting of 50 mM Tris-Cl pH8, 1 mM EDTA. Cells were lysed in a French Press at 14,000–16,000 PSI after which 4 volumes (300 ml) of additional Tris-EDTA were added. Buffer A (β-mercaptoethanol to 5 mM and NP-40 and Tween 20 to 0.5% (v/v) each) was added and the solution was sonicated thoroughly while cooling. The resultant homogeneous suspension was diluted further with Buffer A such that the final volume was 7.5–8 times the starting cell weight; this was designated Fraction I.

The polymerase activity in Fraction I and subsequent fractions was determined in a 50 μl mixture containing 0.025 M TAPS-HCl pH 9.4 (20° C.), 0.002 M $MgCl_2$, 0.05 M KCl, 1 mM 2-mercaptoethanol, 0.2 mM each dGTP, dATP, TTP, 0.1 mM dCTP [α-$^{32}$P, 0.05 Ci/mM], 12.5 μg "activated" salmon sperm DNA and 0.01–0.2 units of the polymerase (diluted in 10 mM Tris-HCl, pH 8, 50 mM KCl, 1 mg/ml autoclaved gelatin, 0.5% NP-40, 0.5% Tween 20, and 1 mM 2-mercaptoethanol). One unit corresponds to 10 nmoles of product synthesized in 30 minutes. "Activated" DNA is a negative preparation of DNA after partial hydrolysis with DNase I until 5% of the DNA was transferred to the acid-soluble fraction. The reaction was conducted at 74° C. for 10 minutes and then 40 μl was transferred to 1.0 ml of 50 μg/ml carrier DNA in 2 mM EDTA at 0° C. An equal volume (1.0 ml) of 20% TCA, 2% sodium pyrophosphate was added. After 15–20 minutes at 0° C. the samples were filtered through Whatman GF/C discs and extensively washed with cold 5% TCA-1% pyrophosphate, followed by cold 95% ethanol, dried and counted.

Fraction I was centrifuged for two hours at 35,000 rpm in a Beckman TI 45 rotor at 2° C. and the collected supernatant was designated Fraction II.

The Taq polymerase activity was precipitated with Polymin P (BRL, Gaithersburg, Md.) (10%, w/v, adjusted to pH 7.5 and autoclaved) after the minimum amount of Polymin P necessary to precipitate 90–95% of the activity was determined, which amount was generally found to be between 0.25% and 0.3% final volume.

An appropriate level of Polymin P was added slowly to Fraction II while stirring for 15 minutes at 0° C. This solution was centrifuged at 13,000 rpm for 20 minutes in a Beckman JA 14 rotor at 2° C. The supernatant was assayed for activity and the pellet was resuspended in 1/5 volume of 0.5× Buffer A (diluted 1:2 with $H_2O$). This suspension was recentrifuged and the pellet resuspended in 1/4 volume of Buffer A containing 0.4 M KCl. This suspension was homogenized thoroughly and left overnight at 4° C. The homogenate was centrifuged as above and the collected supernatant designated Fraction III.

The protein fraction was collected by "precipitation" at 75% saturation of ammonium sulfate, centrifuged (at 27,000 rpm, SW27 rotor, 30 minutes) and the floating pellicle was resuspended in 50 mM Tris-Cl pH 8, 1 mM EDTA. These steps were repeated and the protein suspension was dialyzed extensively with P-cell buffer (20 mM $KPO_4$ pH 7.5, 0.5 mM EDTA, 5 mM β-mercaptoethanol, 5% (w/v) glycerol, 0.5% (v/v) NP-40 and Tween 20) containing 80 mM KCl.

The dialysate was transferred to a centrifuge bottle to which was added any recovered protein from sacks rinsed with the P-cell buffer containing 80 mM KCl. Centrifugation was performed at 20,000× g and the time was reduced to 15 minutes. The supernatant was saved and any pellet remaining was washed, extracted with P-cell buffer and 80 mM KCl, and recentrifuged. The supernatants were then combined to form Fraction IV.

Fraction IV was applied to a 2.2×22-cm column of phosphocellulose, equilibrated with the P-cell buffer containing 80 mM KCl. The column was washed (2.5–3 column volumes) with the same buffer and the protein eluted using a linear gradient of 80 to 400 mM KCl in P-cell buffer. Fractions containing DNA polymerase activity (~0.18–0.20 M KCl) were pooled and concentrated 3–4 fold on an Amicon stirred cell and YM30 membrane. The cell was rinsed with the P-cell buffer without KCl and added to the fraction concentrate (0.15 M KCl adjusted final volume) to form Fraction V.

Fraction V was applied to a 5 ml Heparin Sepharose CL-6B column (Pharmacia) equlibrated with P-cell buffer and 0.15 M KCl. The column was washed with 0.5 M KCl buffer (3–4 column volumes) and the protein eluted with a linear gradient from 0.15 to 0.65 M KCl in P-cell buffer. A 1:10 dilution into diluent without gelatin was made for SDS-PAGE analysis and a subsequent 1:20 dilution into diluent with 1 mg/ml gelatin was made for use in enzyme assays. The activity fractions (eluting at ~0.3 M KCl) were assayed on supercoiled DNA template for specific and non-specific endonucleases/topoisomerase by electrophoretically detecting the change in molecular weight of supercoiled plasmid DNA after incubation with an excess of DNA polymerase. Exonuclease contamination was detected following incubation with small linear DNA fragments. In peak fractions, an ~88–92 kd protein was found to be the major band. The major pool, designated Fraction VI, had the highest polymerase activity with minimal detectable endonuclease activity when this pool was assayed for 30 minutes at 55° C. with ~3–5 polymerase units/600 ng DNA.

Fraction VI was dialyzed against 10 mM KPO$_4$ pH 7.5, 5 mM β-mercaptoethanol, 5% glycerol, 0.2% NP-40, and 0.2% Tween 20 (HA buffer). The dialyzed sample was applied to a 3 ml column of hydroxyapatite and the enzyme eluted with a linear gradient of 10 to 250 mM KPO$_4$ pH 7.5, HA buffer. DNA polymerase activity began to elute at 75 mM KPO$_4$ with the peak at 100 mM KPO$_4$. Active peak fractions were assayed at 1:100–1:300 dilution. As in the prior chromatography step, a 1:10 dilution in diluent was prepared without gelatin for SDS-PAGE analysis. Fractions with no significant endonuclease or double-strand exonuclease when assayed at 55° C. with 5 polymerase units were pooled and designated Fraction VII.

Fraction VII was dialyzed against a solution of 25 mM sodium acetate pH 5.2, 5% glycerol, 5 mM β-mercaptoethanol, 0.1 mM EDTA, 0.1% NP-40, and 0.1% Tween 20, adjusted to pH 5 at room temperature. The dialyzed sample was applied to a 2 ml DEAE-Tris-Acryl-M (LKB) column pre-equilibrated and subsequently washed with the same buffer. The fraction containing polymerase activity that did not adhere to the column was pooled and adjusted to 50 mM NaCl in the same buffer to yield Fraction VIII.

Fraction VIII was applied to a 2 ml CM-Tris-Acryl M (LKB) column equilibrated with the same buffer (25 mM sodium acetate, 50 mM NaCl, 5% glycerol, 0.1 mM EDTA, 0.1% NP-40, and 0.1% Tween 20). The column was washed with 4–5 column volumes of the same buffer and the enzyme eluted with a linear gradient from 50 to 400 mM NaCl in sodium acetate buffer. The polymerase activity peak eluted ~0.15–0.20 M NaCl. The polymerase activity was assayed at 1:300 to 1:500 dilution with the first dilution 1:10 into diluent without gelatin for the SDS-PAGE analysis. An assay across the activity peak on supercoiled DNA templates for specific and non-specific endonuclease/topoisomerase using DNA polymerase assay salts (25 mM TAPS-HCl pH 9.4, 2.0 mM MgCl$_2$ and 50 mM KCl) at 74° C. was performed, as well as assays for nucleases on M13 ss DNA and pBR322 fragments. Active fractions with no detectable nuclease(s) were pooled and run on a silver stained SDS-PAGE mini gel. The results show a single ~88–92 kd band with a specific activity of ~200,000 units/mg.

This specific activity is more than an order of magnitude higher than that claimed for the previously isolated Taq polymerase and is at least an order of magnitude higher than that for *E. coli* polymerase I.

EXAMPLE XIV

The Taq polymerase purified as described above in Example XIII was found to be free of any contaminating Taq endonuclease and exonuclease activities. In addition, the Taq polymerase is preferably stored in storage buffer containing from about 0.1 to about 0.5% volume/volume of each non-ionic polymeric detergent employed. More preferably the storage buffer consists of 50% (v/v) glycerol, 100 mM KCl, 20 mM Tris-Cl pH 8.0, 0.1 mM ethylenediaminetetraacetic acid (EDTA), 1 mM dithiothreitol, 0.5% v/v NP-40, 0.5% v/v Tween 20, and 200 μg/ml gelatin, and is preferably stored at −20° C.

The stored Taq polymerase was diluted in a buffer consisting of 25 mM Tris Cl pH 8.0, 20 mM KCl, 1 mM β-mercaptoethanol, 0.5% NP-40, 0.5% Tween-20, and 500 μg/ml gelatin. A reaction buffer was then prepared containing 50 mM KCl, 10 mM Tris-Cl, pH 8.3, 1.5 mM MgCl$_2$, 0.01% (w/v) gelatin, 200 μM each dNTP, 1 μM each of the primers that define a 500 base pair target sequence on a control template from bacteriophage λ, and 2.0–2.5 units Taq polymerase/assay in a final volume of 100 μl. Template was added to the reaction buffer, the sample placed in a 0.5 ml polypropylene tube, and the sample topped with 100 μl of heavy white mineral oil to prevent evaporation.

At least a $10^5$-fold amplification was achieved when the following conditions were employed, using 1 ng of control template (bacteriophage λ DNA) where the target sequence represented approximately 1% of the starting mass of DNA.

First the template mixture was denatured for one minute, 30 seconds at 94° C. by placing the tube in a heat bath. Then the tube was placed in a heat bath at 37° C. for two minutes. Then the tube was placed in a heat bath for 72° C. for three minutes, and then in the heat bath at 94° C. for one minute. This cycle was repeated for a total of 25 cycles. At the end of the 25th cycle, the heat denaturation step at 94° C. was omitted and replaced by extending the 72° C. incubation step by an additional three minutes. Following termination of the assay, the samples were allowed to cool to room temperature and analyzed as described in previous examples.

The template may be optimally amplified with a different concentration of dNTPs and a different amount of Taq polymerase. Also, the size of the target sequence in the DNA sample will directly impact the minimum time required for proper extension (72° C. incubation step). An optimization of the temperature cycling profile should be performed for each individual template to be amplified, to obtain maximum efficiency.

EXAMPLE XV

Taq polymerase purified as described in Example I was formulated for storage as described in the previous example, but without the non-ionic polymeric detergents. When assayed for activity as described in that example, the enzyme storage mixture was found to be inactive. When the NP-40 and Tween 20 were added to the storage buffer, the full enzyme activity was restored, indicating that the presence of the non-ionic detergents is necessary to the stability of the enzyme formulation.

EXAMPLE XVI

Several 1 μg samples of human genomic DNA were subjected to 20–35 cycles of amplification as described in Example II, with equivalent units of either Klenow fragment or Taq polymerase, and analyzed by agarose gel electrophoresis and Southern blot. The primers used in these reactions, PC03 and PC04, direct the synthesis of a 110-bp segment of the human beta-globin gene. The Klenow polymerase amplifications exhibited the smear of DNA typically observed with this enzyme, the apparent cause of this is the non-specific annealing and extension of primers to unrelated genomic sequences under what were essentially non-stringent hybridization conditions (1x Klenow salts at 37° C.). Nevertheless, by Southern blot a specific 110-bp beta-globin target fragment was detected in all lanes. A substantially different electrophoretic pattern was seen in the amplifications done with Taq polymerase where the single major band is the 110-bp target sequence. This remarkable specificity was undoubtedly due to the temperature at which the primers were extended.

Although, like Klenow fragment amplifications, the annealing step was performed at 37° C., the temperature of Taq-catalyzed reactions had to be raised to about 70° C. before the enzyme exhibited significant activity. During this transition from 37 to 70° C., poorly matched primer-template hybrids (which formed at 37° C.) disassociated so that by the time the reaction reached an enzyme-activating temperature, only highly complementary substrate was available for extension. This specificity also results in a greater yield of target sequence than similar amplifications done with Klenow fragment because the non-specific extension products effectively compete for the polymerase, thereby reducing the amount of 110-mer that can be made by the Klenow fragment.

EXAMPLE XVII

Amplification was carried out of a sample containing 1 μg Molt 4 DNA, 50 mM KCl, 10 mM Tris pH 8.3, 10 mM $MgCl_2$, 0.01% gelatin, 1 μM of each of the following primers (to amplify a 150 bp region):

5'-CATGCCTCTTTGCACCATTC-3'(RS79) and

5'-TGGTAGCTGGATTGTAGCTG-3'(RS80)

1.5 mM of each dNTP, and 5.0 units of Taq polymerase per 100 μl reaction volume. Three additional samples were prepared containing 2.5, 1.3, or 0.6 units of Taq polymerase. The amplification was carried out in the temperature cycling machine described above using the following cycle, for 30 cycles:

from 70 to 98° C. for 1 minute hold at 98° C. for 1 minute from 98° C. to 35, 45 or 55° C. for 1 minute hold at 35, 45 or 55° C. for 1 minute from 35, 45 or 55° C. to 70° C. for 1 minute hold at 70° C. for 30 seconds At 35° C. annealing temperature, the 2.5 units/100 μl Taq enzyme dilution gave the best-signal-to noise ratio by agarose gel electrophoresis over all other Taq polymerase concentrations. At 45° C., the 5 units/100 μl Taq enzyme gave the best signal-to-noise ratio over the other concentrations. At 55° C., the 5 units/100 μl Taq enzyme gave the best signal-to-noise ratio over the other concentrations and over the 45° C. annealing and improved yield. The Taq polymerase has more specificity and better yield at 55° C.

In a separate experiment the Molt 4 DNA was 10-fold serially diluted into the cell line GM2064 DNA, containing no β- or δ-globin sequences, available from the Human Genetic Mutant Cell Depository, Camden, N.J., at various concentrations representing varying copies per cell, and amplification was carried out on these samples as described in this example at annealing temperatures of 35° C. and 55° C. At 35° C., the best that can be seen by agarose gel electrophoresis is 1 copy in 50 cells. At 55° C., the best that can be seen is 1/5,000 cells (a 100-fold improvement over the lower temperature), illustrating the importance of increased annealing temperature for Taq polymerase specificity under these conditions.

In a third experiment, DNA from a cell line 368H containing HIV-positive DNA, available from B. Poiesz, State University of New York, Syracuse, N.Y., was similarly diluted into the DNA from the SC1 cell line (deposited with ATCC on Mar. 19, 1985; an EBV-transformed β cell line homozygous for the sickle cell allele and lacking any HIV sequences) at various concentrations representing varying copies per cell, and amplification was carried out as described in this Example at annealing temperatures of 35° C. and 55° C., using the primers SK38 and SK39, which amplify a 115 bp region of the HIV sequence:

5'-ATAATCCACCTATCCCAGTAGGAGAAAT-3'(SK38) and

5'-TTTGGTCCTTGTCTTATGTCCAGAATGC-3'(SK39)

The results by agarose gel electrophoresis showed that only the undiluted 368H sample could be detected with the annealing temperature at 35° C., whereas at least a $10^{-2}$ dilution can be detected with the annealing temperature at 55° C., giving a 100-fold improvement in detection.

The following bacteriophage and bacterial strains were deposited with the Cetus Master Culture Collection, 1400 Fifty-Third Street, Emeryville, Calif., USA (CMCC) and with the American Type Culture Collection, 12301 Parklawn Drive, Rockville, Md., USA (ATCC). These deposits were made under the provisions of the Budapest Treaty on the International Recognition of the Deposit of Microorganisms for purposes of Patent Procedure and the Regulations thereunder (Budapest Treaty). This assures maintenance of a viable culture for 30 years from the data of deposit. The organisms will be made available by ATCC under the terms of the Budapest Treaty, and subject to an agreement between applicants and ATCC that assures unrestricted availability upon issuance of the pertinent U.S. patent. Availability of the deposited strains is not to be construed as a license to practice the invention in contravention of the rights granted under the authority of any government in accordance with its patent laws.

| Deposit Designation | CMCC No. | ATCC No. | Deposit |
| --- | --- | --- | --- |
| CH35:Taq#4-2 | 3125 | 40336 | 5/29/87 |
| E. coli DG98/pFC83 | 3128 | 67422 | 5/29/87 |
| E. coli DG98/pFC85 | 3127 | 67421 | 5/29/87 |
| E. coli DG95 (λ $N_7N_{53}$ $cI_{857}$ $susP_{80}$)/pFC54.t | 2103 | 39789 | 8/7/84 |
| E. coli DG116/pAW740CHB | 3291 | 67605 | 1/12/88 |

The foregoing written specification is considered to be sufficient to enable one skilled in the art to practice the invention. The present invention is not to be limited in scope by the cell lines deposited, since the deposited embodiment is intended as a single illustration of one aspect of the invention and any cell lines that are functionally equivalent are within the scope of this invention. The deposit of materials therein does not constitute an admission that the written description herein contained is inadequate to enable the practice of any aspect of the invention, including the best mode thereof, nor are the deposits to be construed as limiting the scope of the claims to the specific illustrations that they represent. Indeed, various modifications of the invention in addition to those shown and described herein will become apparent to those skilled in the art from the foregoing description and fall within the scope of the appended claims.

What is claimed is:

1. A stable enzyme composition comprising a purified thermostable nucleic acid polymerase enzyme in a buffer that comprises one or more non-ionic polymeric detergents.

2. The stable enzyme composition of claim 1, wherein said non-ionic polymeric detergents have a molecular weight in the range of 100 to 250,000 daltons.

3. The stable enzyme composition of claim 2, wherein said non-ionic polymeric detergents have a molecular weight in the range of 4,000 to 200,000 daltons.

4. The composition of claim 2 wherein the detergents are each present in a concentration of about 0.1% to about 0.5% volume/volume of the total composition.

5. The composition of claim 2 wherein the detergent is selected from the group consisting of a polyoxyethylated sorbitan monolaurate, an ethoxylated nonyl phenol, ethoxylated fatty alcohol ethers, laurylethers, ethoxylated alkyl phenols, octylphenoxy polyethoxy ethanol compounds, modified oxyethylated and/or oxypropylated straight chain alcohols, polyethylene glycol monooleate compounds, polysorbate compounds, and phenolic fatty alcohol ethers or a combination thereof.

6. The composition of claim 5, wherein said polymerase is a thermostable DNA polymerase.

7. The composition of claim 6 in a buffer with pH in the range of 3.5 to 9.5.

8. The composition of claim 7 wherein the detergent is a polyoxyethylated sorbitan monolaurate, an ethoxylated nonyl phenol or a combination thereof.

9. The composition of claim 6 in a buffer with pH in the range of 4.0 to 8.5.

10. The composition of claim 9, wherein said detergent is present in a concentration of about 0.1% to 1.0%.

11. The composition of claim 10, wherein said DNA polymerase is isolated from a species of the genus Thermus.

12. The composition of claim 11, wherein said species is selected from the group consisting of *flavus, ruber, thermophilus, aquaticus, lacteus,* and *rubens*.

13. The composition of claim 11, wherein said species is *aquaticus*.

14. The composition of claim 13 wherein the buffer comprises glycerol; Tris-HCl, pH 8.0; ethylenediamine tetraacetic acid; dithiothreitol; a polyoxyethylated sorbitan monolaurate; an ethoxylated nonyl phenol; and gelatin.

15. The composition of claim 14 wherein the buffer comprises 50% glycerol; 20 mM tris-HCl, pH 8; 0.1 mM ethylenediamine tetraacetic acid; 1 mM dithiothreitol; 0.5% volume/volume of a polyoxyethylated sorbitan monolaurate; 0.5% volume/volume of an ethoxylated nonyl phenol; and 200 µg/ml gelatin.

16. The composition of claim 11, wherein said species is *flavus*.

17. The composition of claim 11, wherein said species is *thermophilus*.

18. A reaction mixture that comprises nucleoside-5'-triphosphates, oligonucleotide primers, a buffer in which primer extension by a polymerase can occur, and an aliquot of a stable enzyme composition comprising a purified thermostable nucleic acid polymerase enzyme in a buffer and further comprising one or more nonionic polymeric detergents.

* * * * *

(12) EX PARTE REEXAMINATION CERTIFICATE (5823rd)
United States Patent
Gelfand et al.

(10) Number: US 6,127,155 C1
(45) Certificate Issued: Jul. 24, 2007

(54) STABILIZED THERMOSTABLE NUCLEIC ACID POLYMERASE COMPOSITIONS CONTAINING NON-IONIC POLYMERIC DETERGENTS

(75) Inventors: David H. Gelfand, Oakland, CA (US);
Susanne Stoffel, El Cerrito, CA (US);
Randall K. Saiki, Richmond, CA (US)

(73) Assignee: Roche Molecular Systems, Inc., Branchburg, NJ (US)

Reexamination Request:
No. 90/007,416, Feb. 9, 2005

Reexamination Certificate for:
Patent No.: 6,127,155
Issued: Oct. 3, 2000
Appl. No.: 07/873,897
Filed: Apr. 24, 1992

Related U.S. Application Data

(63) Continuation of application No. 07/387,003, filed on Jul. 28, 1989, now abandoned, which is a division of application No. 07/143,441, filed on Jan. 12, 1988, now abandoned, which is a continuation-in-part of application No. 07/063,509, filed on Jun. 17, 1987, now Pat. No. 4,889,818, which is a continuation-in-part of application No. 06/899,241, filed on Aug. 22, 1986, now abandoned.

(51) Int. Cl.
*C12P 19/00* (2006.01)
*C12P 19/34* (2006.01)
*C12Q 1/68* (2006.01)
*C12N 15/70* (2006.01)
*C12N 9/12* (2006.01)

(52) U.S. Cl. ............... 435/188; 435/183; 435/471; 435/478; 435/488; 435/6; 435/69.1; 435/814; 435/91.1; 435/91.2

(58) Field of Classification Search ............... 435/6, 435/188, 91.1, 91.2
See application file for complete search history.

(56) References Cited

U.S. PATENT DOCUMENTS

| | | | |
|---|---|---|---|
| 4,457,916 A | 7/1984 | Hayashi et al. | |
| 4,683,195 A | 7/1987 | Mullis et al. | |
| 4,683,202 A | 7/1987 | Mullis | |
| 4,889,818 A | 12/1989 | Gelfand et al. | |

FOREIGN PATENT DOCUMENTS

| | | |
|---|---|---|
| EP | 166529 | 1/1986 |
| JP | 82/149890 | 8/1982 |
| JP | 83/69230 | 4/1983 |
| JP | 60-224499 | 11/1985 |
| JP | 86/293926 | 12/1986 |
| WO | WO 83/00288 | 2/1983 |

OTHER PUBLICATIONS

Chemical Abstract (CA) information (RN: 9004–95–9) Nov. 1984 (STN) and Apr. 26, 2006 (internet).*
Amendment dated Mar. 9, 1989, U.S. Appl. No. 07/063,509.
Information Disclosure Statement dated May 10, 1990, U.S. Appl. No. 07/387,003.
Examiner's Office Action rejecting pending claims, U.S. Appl. No. 07/387,003.
Response to Office Action dated Feb. 11, 1991, U.S. Appl. No. 07/387,003.
Declaration Under 37 C.F.R. Section 1.131 (signed solely by D. Gelfand) dated Feb. 11, 1991, U.S. Appl. No. 07/387,003.
Preliminary Amendment dated Apr. 24, 1992, U.S. Appl. No. 07/873,897.
Declaration Under 37 C.F.R. Section 1.131 (signed by all three named inventors) dated Apr. 24, 1992, U.S. Appl. No. 07/873,897.
Appeal Brief Pursuant To 37 C.F.R. Section 1.192 dated Feb. 17, 1994, U.S. Appl. No. 07/873,897.
Decision Before the Board of Patent Appeals and Interferences reversing all Examiner's objections mailed Jul. 30, 1999, U.S. Appl. No. 07/873,897.
Amendment Under 37 C.F.R. Section 1.111 dated Jan. 19, 1993, U.S. Appl. No. 07/873,897.
Reply Brief Under 37 C.F.R. Section 1.193(b) dated Jul. 11, 1994, U.S. Appl. No. 07/873,897.
Ex Parte Reexamination Advisory Action (Reexam Control No. 90/006,184).
Ex Parte Reexamination Advisory Action (Reexam Control No. 90/006,805).
Notice of Intent to Issue Ex Parte Reexamination Certificate in Reexamination Control No. 90/006,184.
Wang & Hanson, *J Parenteral Science & Technology* 42 *Supplement*: S3–25 (1988).
Apr. 29, 1998 Order from *Hoffmann–La Roche, Inc.* v. *Promega Corp.*, C–93–1748–VRW (N.D. Cal.).
2000 Draft Nullity Brief Prepared by New England BioLabs ("NEB") for *F. Hoffman–La Roche AG* v. *Bresagen Ltd. & Anor.* No. NG__(Federal Court of Australia).
May 16, 2000 Letter to the Australian Commissioner of Patents re: Amending AU 632857.

(Continued)

*Primary Examiner*—Bennett Celsa

(57) ABSTRACT

A purified thermostable nucleic acid polymerase is obtained that has unique characteristics. Preferably the nucleic acid polymerase is DNA polymerase isolated from a *Thermus aquaticus* species and has a molecular weight of about 86,000–95,000 daltons. The thermostable nucleic acid polymerase may be native or recombinant and may be used in a temperature-cycling chain reaction wherein at least one nucleic acid sequence is amplified in quantity from an existing sequence with the aid of seleced primers and nucleotide triphosphates. The nucleic acid polymerase is preferably stored in a buffer containing non-ionic detergents that lends stability to the nucleic acid polymerase. A preferred buffer contains glycerol, polyoxyethylated sorbitan monolaurate, ethoxylated nonyl phenol and gelatin.

Jun. 19, 2000 Letter to the Australian Commissioner of Patents re: Amending AU 632857 plus Exhibits.

Oct. 30, 2002 Letter to the Australian Commissioner of Patents re: Amending AU 632857.

Oct. 5, 2004 Outline of Submissions by NEB in *NEB, Inc. v. F. Hoffman–La Roche AG*, No. N1305 of 2003 (Federal Court of Australia).

Oct. 5, 2004 Outline of Submissions by Roche in *NEB, Inc. v. F. Hoffman–La Roche AG*, No. N1305 of 2003 (Federal Court of Australia).

Apr. 26, 2005 Supplementary Summary of Argument by NEB in *NEB, Inc. v. F. Hoffman–La Roche AG*, No. S345 of 2004 (High Court of Australia).

English Translation of Jan. 28, 2005 Nullity Brief filed by Promega Corp. in *Promega Corp. v. F. Hoffmann–La Roche AG*, German Federal Patent Court.

English Translation of Expert Opinion by Prof. Dr. Eggehard Holler in *Promega Corp. v. F. Hoffman–La Roche AG*, German Federal Patent Court.

Jan. 7, 2005 Letter filed on behalf of Bioline (UK) Ltd. to the European Patent Office re: Appeal T 0340/00 (EP 0 395 736) plus Exhibits.

Jan. 11, 2005 Letter filed on behalf of F. Hoffmann–La Roche AG to the European Patent Office re: Appeal T 0340/00 (EP 0 395 736).

Mar. 31, 2005 Decision of the European Patent office Technical Board of Appeal in No. T340/00–338 (EP 0 395 736).

Redacted Excerpts (pp. 1, 28–39) from Amended Complaint filed by Promega Corp. in *US ex rel. Promega Corp. v. Hoffmann–La Roche Inc.*, No. 03cv1447 (E.D. Va. 2004). Prep 4 (A05057–58).

Excerpts from Stoffel Notebook 2297 (pp. 1, 5–78, 134–162).

Excerpts from Saiki Notebook 2369 (p. 51).

Excerpts from Stoffel Notebook 2146 (pp. 126–130, 161–162, 191–192).

Excerpts from Akers Notebook 21300 (pp. 1–10, 14–33).

Excerpts from Saiki Notebook 2522 (pp. 132–134, 168–172, 174–175).

Excerpts from Saiki Notebook 2610 (pp. 60–61, 67).

Excerpts from Saiki Notebook 2849 (pp. 22–23, 27–29, 32, 70–72, 74–75, 79–81, 84–89, 174–175).

Perkin–Elmer Cetua GeneAmp™ DNA Amplification Reagent Kit (Part No. N801–0043) product insert.

Chien, "Purification And Characterization Of DNA Polymerase From *Thermus Aquaticus*" (1976) (Master of Science Thesis, University of Cincinnati) (the "Chien Thesis").

Chien et al., "Deoxyribonucleic Acid Polymerase From Extreme Thermophile *Thermus Aquaticus*," *J. Bacteriology* 127(3): 1550–57 (1976) (the "Chien Reference").

Edgar, "DNA Polymerase From An Extreme Thermophile: *Thermus Aquaticus*" (1972) (Master of Science Thesis, University of Cincinnati) (the Edgar Thesis).

Kaledin et al., "Isolation And Properties Of DNA Polymerase From Extremely Thermophilic Bacterium *Thermus Aquaticus* YT1," *Biochemistry* 45(4):494–501 (1979) (the "Kaledin *Taq* Reference").

Kaledin et al., "Isolation And Properties Of DNA Polymerase From The Extremely Thermophilic Bacterium *Thermus Flavus*," *Biochem.* 46(9):1247–54 (1981) (the "Kaledin *Tfl* Reference").

Kaledin et al., "Isolation And Properties Of DNA Polymerase From The Extremely Thermophilic Bacterium *Thermus Ruber*," *Biochem.* 47(11):1515–21 (1982) (the "Kaledin *Tru* Reference").

Ruttimann et al., "DNA Polymerases From The Extremely Thermophilic Bacterium *Thermus Thermophilus* HB–8," *Eur. J. Biochem.* 149:41–46 (1985).

Alwine et al., "Method For Detection Of Specific RNAs In Agarose Gels By Transfer To Diazobenzyloxymethyl Paper And Hybridization With DNA Probes," *PNAS USA* 74:5350 (1977).

Bell et al., "Purification And Amino Acid Compositions Of The Structural Proteins Of Sinbis Virus," *Virology* 97:287–94 (1979).

"Biochemical Experiment Lectures 1, Protein Chemistry I–Isolation and Purification," pp. 66–67 (1976) (Ref.) (translation of relevant text provided).

Burgess et al., "Purification And Properties Of Colony–Stimulating Factor From Mouse Lung–Conditioned Medium," *J. Biol. Chem.* 252:1998–2003 (1977).

Dalgarno et al., "Characterization Of Barmah Forest Virus: An Alphavirus With Some Unusual Properties," *Virology* 133:416–26 (1984).

Denhardt, "A Membrane–Filter Technique For The Detection Of Complementary DNA," *Biochem–Biophys. Res. Comm.* 23:641–52 (1966).

Elices, M. J., Blake, D. A., Goldstein, I. J., (1986) Purification and Characterization of a UDP–Gal: β–D–Gal(1, 4)–D–GlcNAc α(1,3)–Galactosyltransferase from Ehrlich Ascites Tumor Cells. *J. Biol. Chem.*, 261, 6064–6072.

Faras et al., "Purification And Characterization Of The Deoxyribonucleic Acid Polymerase Associated With Rous Sarcoma Virus," *Biochemistry* 11(12):2334–42 (1972).

Haeckel, "The Reliability Of A Mechanised Procedure (Perkin–Elmer C4) For The Enzymatic Determination Of Uric Acid According To Kageyama," *J. Clin. Chem. Clin. Biochem.* 14:165–71 (1976).

Hjelmeland, "Solubilization Of Native Membrane Proteins," *Meths Enzymol.* 182: 253 (1990).

Husby et al., "Increased Non–Specific Binding Of Heat–Treated Proteins To Plastic Surfaces Analysed By ELISA And HPLC–Fractionation," *J. Immunoassay* 6:95–110 (1985).

Kemp, "Unique And Repetitive Sequences In Multiple Genes For Feather Keratin," *Nature* 254:573–77 (1975).

Kemp & Cowan, "Direct Immunoassay For Detecting *E. Coli* Colonies That Contain Polypeptides Encoded By Cloned DNA Segments," *PNAS USA* 78(7):4520–24 (1981).

Landi et al., "The Multi–Facets Of Tuberculin Standardisation," *Dev. Biol. Stand.* 29:393–411 (1975).

Livesey, "Prevention Of Adsorption Losses During Radio-immunoassay Of Polypeptide Hormones: Effectiveness Of Albumins, Gelatin, Caseins, Tween 20 And Plasma," *Clin. Chim. Acta* 123:193–98 (1982).

Martin et al., "Replication Of Standard And Defective Ross River Virus In BHK Cells: Patterns Of Viral RNA And Polypeptide Synthesis," *Archs. Virology* 61:87–103 (1979).

McCutcheon's *Emulsifiers And Detergents*, pp. 295–298 (N. Am. Ed. 1983).

Neugebauer, "Detergents: An Overview," *Meths. Enzymol.* 192:739 (1990).

Ohno et al., "Purification And Characterization Of The DNA Polymerase Of Human Breast Cancer Particles," *PNAS USA* 74(2):764–68 (1977).

Pearson et al., "Studies Of Protein Kinase/Phosphotase Specificity Using Synthetic Peptides" in *Protein Phosphorylation—A Practical Approach* (D.G. Hardie, ed. 1993) (Ref.).

Pearson et al., "Myosin Light Chain Kinase Binding To Plastic," *FEBS Letters 145*:327–31 (1982).

Pirrotta et al., "Gerneral Purification Schemes For Restriction Endonucleases," *Methods Enzymol.* 65:89–95 (1980).

Rosevear, "Alkyl Glycoside Detergents: A Simpler Synthesis And Their Effects On Kinetic And Physical Properties Of Cytochrome c Oxidase," *Biochem.* 19 (17): 4108–15 (1980).

Scopes, *Protein Purification. Principles and Practice*, excerpts from Sections 2.3–2.4 (Springer–Verlag).

Smith et al., "Elimination Of Nonspecific Adsorption Of Serum Proteins By Sepharose–Bound Antigens," *Anal. Biochem.* 87 87:299–305 (1978).

Stralfors & Belfrage, "Properties And Purification Of The Catalytic Subunit Of Cyclic AMP–Dependent Protein Kinase Of Adipose Tissue," *Biochem. Biophys. Acta* 721:434–440 (1982).

Sudgen et al., "Purification And Characterization Of The Catalytic Subunit Of Adenosine 3':5'–Cyclic Monophosphate–Dependent Protein Kinase From Bovine Liver," *Biochem. J.* 159:409–22 (1976).

Suelter, "Protein Structure And Stability" in *A Practical Guide to Enzymology*, chptrs. 1 and 3 (John Wiley & Sons 1985).

Umbreit, "Relation Of Detergent HLB Number To Solubilisation And Stabilisation Of D–Alanine Carboxypeptidase from *Bacillus Subtilis* Membranes," *PNAS USA* 70(10): 2997–3001 (1973).

Wu & Cetta, "On The Stimulation Of Viral DNA Polymerase By Non–Ionic Detergents," *Biochemistry* 14(4):789–95 (1975).

Verrey, F. and Drickamer, K., (1993). Determinants of oligomeric structure in the chicken liver glycoprotein receptor. *Biochem. J.*, 292, 149–155.

Zhao, K.W., Yeh, R., and Miller, A.L., (1992). Purification and Characterization of Human Lymphoblase N–accetylglucosamine–1–phosphotransferase. *Glycobiol.*, 2, 119–25.

McCarthy, M.P., and Morre, M.A., (1992). Effects of Lipids and Detergents on the Conformation of the Nicotinic Acetylcholine Receptor from Torpedo Californica. *J. Biol. Chem.*, 267, 7655–63.

Sami, M., Malik, S., and Watts, A., (1992). Structural Stability of the Erythrocyte Anion Transporter, Band 3, in Native Membranes and in Detergent Micelles. *Biochim. Biophys.* Acta, 1105, 148–54.

Vishwanatha, J.K., and Wei, Z., (1992). Diadenosine Tetraphosphate Binding Protein from Human HeLa cells: Purification and Characterization. *Biochem.*, 31, 1631–5.

Gianfreda, L., and Scarfi, M.R., (1991). Enzyme Stabilization: state of the art. *Mol. Cell. Biochem.*, 100, 97–128.

Simpson, W.J., and Hammond, J.R., (1991). The Effects of Detergents on Firefly Luciferase Reactions. *J. Biolumin. Chemilumin.*, 6, 97–106.

Kaul, R., Casanova, J., Johnson, A.B., Tang, P., and Matalon, R., (1991). Purification, Characterization, and Localization of Aspartoacylase from Bovine Brain. *J. Neurochem.*, 56, 129–35.

Ayala, G., and Mendoza–Hernandez, G., (1990). Stability and Activity of 20 Beta–hydroxysteroid Dehydrogenase in Microemulsion of Non–ionic Detergents. *Biochem. Int.*, 22, 717–23.

Okuno, S., and Fujisawa, H., (1990). Stabilization, Purification and Crystallization of Catalytic Subunit of cAMP–dependent Protein Kinase from Bovine Heart. *Biochim. Biophys. Acta*, 1038, 204–8.

Rey, M.A., Laurent, A.G., McClure, J., Krust, B., Montagnier, L., and Hovanessian, A.G., (1990). Transmembrane Envelope Glycoproteins of Human Immunodeficiency Virus Type 2 and Simian Immunodeficiency Virus SIV–mac Exists as Homodimers., *J. Virol.*, 64, 992–6.

Rottini, G., Dobrina, A., Forgiarini, O., Nardon, E., Amirante, G.A., and Patriarca, P., (1990). Identification and Partial Characterization of a Cytolytic Toxin Produced by *Gardnerella vaginalis*. *Infect Immun.*, 58, 3751–8.

Schein, Catherine H., (1990). Solubility as a Function of Protein Structure and Solvent Components: *Biotechnol.*, 8, 308.

Barnes, J.A., (1989). Conformation and Stability of Sendai Virus Fusion Protein. *Int. J. Biol. Macromol.*, 11, 130–6.

Uerkvitz, W., (1988). Periplasmic Nonspecific Acid Phosphate II from *Salmonella typhimurlum* LT2. Crystallization, Detergent Reactivation, and Phosphotransferase Activity. *J. Biol. Chem.*, 263, 15823–30.

Tandon, S., and Horowitz, P.M., (1987). Detergent–assisted Refolding of Guanidinium Chloride–denatured Rhodanese. The effects of the Concentration and Type of Detergent. *J. Biol. Chem.*, 262, 4486–91.

Tandon, S., and Horowitz, P.M., (1986), Detergent–assisted Refolding of Guanidinium Chloride–denatured Rhodanese. The Effect of Lauryl Maltoside. *J. Biol. Chem.*, 261, 15615–8.

Markovic–Housley, Z., and Garavito, R.M., (1986). Effect of Temperature and Low pH on Structure and Stability of Matrix Porin in Micellar Detergent Solutions. *Biochim. Biophys. Acta*, 869, 158–70.

Wagner, S.L., and Gray, R.D., (1985). Effects of Detergent on Substrate Binding and Spin State of Purified Liver Microsomal Cytochrome P–450 (LM2) from Phenobarbital–treated rabbits. *Biochemistry*, 24, 3809–14.

Webber, S., and Whiteley, J.M., (1985). Comparative Activity of Rat Liver Dihydrofolate Reductase with 8,8–dihydrofolate and other 7,8–dihydropteridines. *Arch. Biochem. Biophys*, 236, 681–90.

Brunden, K.R., Uratani, Y., and Cramer, W.A., (1984). Dependence of the Conformation of a Colicin B1 Channel–forming Peptide on Acidic pH and Solvent Polarity. *J. Biol. Chem.*, 259, 7682–9.7.

Miller, A.W., and Robyt, J.F., (1984). Stabilization of Dextransucrase from *Leuconostoc masenteroides* NRRL B–512F by Nonionic Detergents, Poly(ethylene glycol) and High–molecular–weight dextran. *Biochim. Biophys Acta*, 785, 89–96.

Sawada, H. Yokosawa, H., and Ishii, S., (1984). Purification and Characterization of Two Types of Trypsin–like Enzymes from Sperm of the Ascidian (Prochordata) *Halocynthia roretzi*. Evidence for the Presence of Spermosin, a novel Acrosin–like Enzyme. *J. Biol. Chem.*, 259, 2900–4.

Grimshaw, C.E., Henderson, G.B., Soppe, G.G., Hansen, G., Mathur, E.J., and Huennekens, F.M., (1984). Purification and Properties of 5,10 Methenyltetrahydrofolate Synthetase from *Lactobacillus casei*. *J.Biol. Chem.*, 259, 2728–33.

Gavish, M., (1983). Protection of Soluble Benzodiazepine Receptors from Heat Inactivation by GABAergic Ligands. *Life Sci.,* 33, 1479–83.

Mozhaev, V.V., and Martinek, K., (1982). Inactivation and Reactivation of Proteins (enzymes). *Enzyme Microb. Tech.,* 4, 299–309.

Ito, Y., and Kuriyama, K., (1983). Some Properties of Solubilized GABA Receptor. *Brains Res.,* 236, 351–64.

Roach, P.D., and Palmer, F.B., (1981). Human Erythrocyte Cytosol Phosphatidyl–inositol–bisphosphate Phosphatase. *Biochim. Biophys Acta,* 661, 323–33.

Porstmann, B., Porstmann, T., Gaede, D., Nugel, E., and Egger, E., (1981). Temperature Dependent Rise in Activity of Hoseradish Peroxidase Caused by Non–ionic Detergents and Its Use in Enzyme–immunoassay. *Clin. Chim. Acta,* 109, 175–81.

Yang, K., Samanta, H., Dougherty, J., Jayaram. B., Broeze, R., and Lengyel, P., (1981). Interferons, double–stranded RNA, and RNA degradation. Isolation and Characterization of Homogeneous Human (2'–5')(a)n Synthetase. *J. Biol. Chem.,* 256, 9323–8.

Becht, I., Schrecker, O., Klose, G., and Greten, H., (1980). Purification of Human Plasma Lipoprotein Lipase. *Biochim. Biophys Acta,* 620, 583–91.

Muller–Esterl. WI, and Firtz, H., (1980). Interactions of Boar Acrosin with Detergents. *Hoppe Seylers Z. Physiol. Chem.,* 361, 1673–82.

Rode, W., Scanlon, K.J., Hynes, J., and Bertino, J.R., (1979). Purification of Mammalian Tumor (L1210) Thymidylate Synthetase by Affinity Chromatography on Stable Biospecific Adsorbent. *J. Biol. Chem.,* 254, 11538–11543.

Helenius, A., McCaslin, D.R., Fries, E. and Tanford, C., (1979). Properties of Detergents. *Meth. in Enz.,* 56, 734–49.

Knudsen, P., and Hubbell, W.L., (1978). Stability of Rhodopsin in Detergent Solutions. *Mambr. Biochem.,* 1, 297–322.

Callahan, J.W., Shankararn, P., Khalil, M., and Gerrie, J., (1978). Sphingomyelinase in Human Tissues. IV. Purification of Sphingomyelinase from Human Placenta and Effect of Triton X–100. *Can. J. Biochem.,* 56, 885–91.

Sedmak, J.J., Jameson, P., and Grossberg, S.E. (1978). Thermal and Vortical Stability of Purified Human Fibroblast Interferon. *Adv. Exp. Med. Biol.,* 110, 133–52.

Rizzolo, L.J. and Tanford, C. (1978). Behavior of Fragmented Calcium (II) Adenosine Triphosphatase from Sarcoplasmic Reticulum in Detergent Solution. *Biochem.,* 17, 4049–55.

Mihara, K., and Sato, R., (1978). Dtergent–Solubilized NADH–Cytochrome b, Reducrase. *Meth. in Enz.,* 52, 102.

Kaczorowski, G., K., Kohn, L.D., and Kaback, H.R., (1978). Purification and Properties of D–Lactate Dehydrogenase from *Escherichia coli* ML 308–225. *Meth. in Enz.,* 53, 501.

Yokoyama, S., Miyabe, T., Oobayashi, A., Tanabe, O., Ichishima, E., (1977). Stabilization of Crystalline Acid Carboxypeptidase from *Penicillium janthinellum* by Nonionic Surfactants, and Inhibition of Enzyme Activity by Anionic Compounds. *Agric. Biol. Chem.,* 41, 1379–1383.

Yamashita, S., Nakaya, N., Miki, Y., and Numa, S. (1975). Separation of I–acylglycerolphosphate Acyltransferase and 1–acylglycerolphorylcholine Acyltransferase of Rat Liver Microsomes. *Proc. Natl. Acad. Sci. USA,* 72, 600–3.

Helenius, A., and Simons, K., (1975). Solubilization of Membranes by Detergents. *Biochimica et Biophysica Acta,* 415, 29–79.

Verma, I.M.., and Baltimore, D., (1974). Purification of the RNA–Directed DNA Polymerase from Avian Myeloblastosis Virus and Its Assay with Polynucleotide Templates. *Meth. in Enz.,* 24, 124.

Moses, R.E., (1974). DNA Synthesis in Toluene–Treated Cells of *Escherichla coli. Meth. in Enz.,* 24, 222.

Takeda, Y., and Hizukuri, S., (1972). Effect of Triton X–100 on Sweet potato B–amylase. *Biochim. Biophys. Acta,* 268, 175–183.

Gatt, S., and Barenholz, Y., (1969). Sphingomyelinase from Rat Brain. *Meth. in Enz.,* 14, 144.

Ernster, L., (1967). DT Diaphorase. *Meth. in Enz.,* 10, 518.

Wiedmer, T., Di–Francesco, C., Brodbeck, U. (1979). Effects of Amphiphiles on Structure and Acitivity of Human Erythrocyte Membrane Acetylcholinesterase. *Eur–J. Biochem.,* 102, 59–64.

Lougheed, W.D., Albisser, A.M., Martindale, H.M., Chow, J.C., Clement, J.R., (1983). Physical Stability of Insulin Formulations. *Diabetes.* 32, 424–32.

Sonoda, T., Tatibana, M., Purification of N–acetyl–L–glutamate Synthetase from Rat Liver Mitochondria and Substrate and Activator Specificity or the Enzyme. (1983). *J. Biol. Chem.,* 258, 9839–44.

Laskowski, Sr., M., (1980) Purification and Properties of the Mung Bean Nuclease. *Methods in Enzymology,* 65, 263.

Ghosh, P.K., Reddy, V.B., Piatak, M., Lebowitz, P., Weissman, S.M., (1980) Determination of RNA Sequences by Primer Directed Synthesis and Sequencing of their cDNA Transcripts. *Methods in Enzymology,* 65, 59.

Bresatec's Notice Of Opposition In The Matter Of Australian Patent Application Serial No. 632 857.

New England Biolabs Notice Of Opposition In The The Matter Of Australian Patent Application Serial No. 632 857.

Aug. 14, 1995 Dimond Statutory Declaration In The Matter Of Australian Patent Application Serial No. 632 857.

Feb. 8, 1996 Dixon Statutory Declaration In The Matter Of Australian Patent Application Serial No. 632 857.

Oct. 4, 1994 Gelfand Statutory Declaration Filed In The Matter Of Australian Patent Application Serial No. 632 857.

Jan. 6, 1995 Gelfand Statutory Declaration Filed In The Matter Of Australian Patent Application Serial No. 632 857.

Aug. 28, 1995 Kornberg Statutory Declaration In The Matter Of Australian Patent Application Serial No. 632 857.

Jun. 20, 1995 Roberts Statutory Declaration Filed In The Matter Of Australian Patent Application Serial No. 632 857.

Sep. 1, 1993 Schildkraut Statutory Declaration Filed In The Matter Of Australian Patent Application Serial No. 632 857.

Sep. 2, 1993 Scopes Statutory Declaration Filed In The Matter Of Australian Patent Application Serial No. 632 857.

Feb. 9, 1996 Scopes Statutory Declaration In The Matter Of Australian Patent Application Serial No. 632 857.

Aug. 12, 1993 Verma Statutory Declaration In The Matter Of Australian Patent Application Serial No. 632 857.

Apr. 1997 Decision Of A Delegate Of The Commissioner In The Opposition To Australian Patent No. 682 857.

New England Biolabs' Notices Of Appeal And Statements Of Grounds Of Opposition In The Appeal From The Delegate's Decision In The Australian Opposition.

Dalgarno Affidavit Filed In The Appeal From The Delegate's Decision In The Australian Opposition.

Hopwood Affidavit (With Thesis) Filed In The Appeal From The Delegate's Decision In The Australian Opposition.

Jun. 30, 1999 Kemp Affidavit Filed In The Appeal From The Delegate's Decision In The Australian Opposition.

Jul. 1, 1999 Kemp Affidavit Filed In The Appeal From The Delegate's Decision In The Australian Opposition.

Apr. 6, 2000 Kemp Affidavit Filed In The Appeal From The Delegate's Decision In The Australian Opposition.

Schildkrauat Affidavit Filed In The Appeal From The Delegate's Decision In The Australian Opposition.

Wilton Affidavit Filed In The Appeal From The Delegate's Decision In The Australian Opposition.

Duggleby Affidavit Filed In The Appeal From The Delegate's Decision In The Australian Opposition.

Mattick Affidavit Filed In The Appeal From The Delegate's Decision In The Australian Opposition.

Rowe Affidavit Filed In The Appeal From The Delegate's Decision In The Australian Opposition.

Vicuna Affidavit Filed In The Appeal From The Delegate's Decision In The Australian Opposition.

Bioline Ltd.'s Mar. 4, 1998 Opposition To The Grant Of EP 0258017.

Promega Corp's Mar. 4, 1998 Opposition To The Grant Of EP 0258017.

Declaration of Randall Dimond Filed As Part Of Promega Corp's Opposition.

Declaration of Arthur Kornberg Filed As Part Of Promega Corp's Opposition.

Becton Dickinson and Company's Mar. 2, 1998 Opposition To The Grant Of EP 0258017.

Roche's Jun. 4, 1999 Response To The European Oppositions (including Exhibit XIII).

Jul. 16, 2001 Minutes From The European Opposition Proceedings.

Aug. 30, 2001 Decision Of The European Opposition Division.

Roche's Jan. 9, 2002 Appeal To The European Technical Board Of Appeals.

Promega Corp's Feb. 17, 2003 Opposition To The European Technical Board Of Appeals.

Roche's Aug. 29, 2003 Supplemental Submission To The European Technical Board Of Appeals.

Mar. 23, 2004 Decision Of The European Technical Board Of Appeals.

English Translation Okada's Sep. 6, 1991 Patent Opposition Brief Challenging The Validity Of JP 31434.

English Translation Of The Sep. 7, 1993 Decision By The Japanese Opposition Division.

European Patent Application EP 0 776 970 A1.

May 10, 2002 EP Communication Pursuant To Article 96(2) EPC.

Roche's Jan. 3, 2005 Response To The EP Communication.

New England Biolabs Taq DNA Polymerase Lot Assay Document.

Rein Notebook.

Roche v. Promega, 319 F. Supp.2d 1011 (N.D. Cal. 2004).

Roche v. Promega, 323 F.3d 1354 (Fed. Cir. 2003).

Roche v. Promega, 1999 WL 1797330 (N.D. Cal. 1999).

Roche v. Promega, Aug. 9, 1996 Order (N.D. Cal. 1996).

Roche v. Promega, Dec. 31, 1997 Order (N.D. Cal. 1997).

* cited by examiner

US 6,127,155 C1

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 14, lines 39–62:

Stabilization of Enzyme Activity

For long-term stability, the enzyme herein must be stored in a buffer that contains one or more non-ionic polymeric detergents. Such detergents are generally those that have a molecular weight in the range of approximately 100 to 250,000, preferably about 4,000 to 200,000 daltons and stabilize the enzyme at a pH of from about 3.5 to about 9.5, preferably from about 4 to 8.5. Examples of such detergents include those specified on pages 295–298 of McCutcheon's Emulsifiers & Detergents, North American edition (1983), published by the McCutcheon Division of MC Publishing Co., 175 Rock Road, Glen Rock, N.J. (USA), the entire disclosure of which is incorporated herein by reference. Preferably, the detergents are selected from the group comprising ethoxylated fatty alcohol ethers and lauryl ethers, ethoxylated alkyl phenols, octylphenoxy polyethoxy ethanol compounds, modified oxyethylated and/or oxypropylated straight-chain alcohols, polyethylene glycol monooleate compounds, polysorbate compounds, and phenolic fatty alcohol ethers. More particularly preferred are Tween 20, from ICI Americas Inc., Wilmington, Del., which is a polyoxyethylated (20) sorbitan monolaurate, and Iconol™ NP-40, from BASF Wyandotte Corp. Parsippany, N.J., which is an ethoxylated alkyl phenol (nonyl)[, and polyoxyethylene alkyl phenyl ethers such as Triton-X100, which is a polyoxyethylene octyl phenyl ether].

AS A RESULT OF REEXAMINATION, IT HAS BEEN DETERMINED THAT:

The patentability of claim 18 is confirmed.

Claims 1 and 5 are determined to be patentable as amended.

Claims 2–4 and 6–17, dependent on an amended claim, are determined to be patentable.

New claims 19–111 are added and determined to be patentable.

1. A stable enzyme composition comprising a purified thermostable nucleic acid polymerase enzyme in a buffer that comprises one or more non-ionic polymeric detergents *other than polyoxyethylene cetyl ether*.

5. The composition of claim 2 wherein the detergent is selected from the group consisting of a polyoxyethylated sorbitan monolaurate, an ethoxylated nonyl phenol, ethoxylated fatty alcohol ethers, laurylethers, ethoxylated alkyl phenols, octylphenoxy polyethoxy ethanol compounds, modified [oxyethylated and/or] oxypropylated straight chain alcohols, polyethylene glycol monooleate compounds, polysorbate compounds, and phenolic fatty alcohol ethers or a combination thereof.

*19. The composition of any one of claims 1–4, wherein the composition comprises at least one non-ionic polymeric detergent, said non-ionic polymeric detergent being a polyoxyethylated sorbitan monolaurate.*

*20. The composition of any one of claims 1–4, wherein the composition comprises at least one non-ionic polymeric detergent, said non-ionic polymeric detergent being an ethoxylated alkyl phenol.*

*21. The composition of any one of claims 1–4, wherein the composition comprises at least one non-ionic polymeric detergent, said non-ionic polymeric detergent being an octylphenoxy polyethoxy ethanol compound.*

*22. The composition of any one of claims 1–4, wherein the composition comprises at least two non-ionic polymeric detergents, said detergents being a polyoxyethylated sorbitan monolaurate and an ethoxylated alkyl phenol.*

*23. The composition of claim 19, wherein said polyoxyethylated sorbitan monolaurate is polyoxyethylated (20) sorbitan monolaurate.*

*24. The composition of claim 22, wherein said polyoxyethylated sorbitan monolaurate is polyoxyethylated (20) sorbitan monolaurate.*

*25. The composition of claim 20, wherein said ethoxylated alkyl phenol is an ethoxylated nonyl phenol.*

*26. The composition of claim 22, wherein said ethoxylated alkyl phenol is an ethoxylated nonyl phenol.*

*27. The composition of claim 19, wherein said purified thermostable nucleic acid polymerase is a DNA polymerase from a species of the genus Thermus.*

*28. The composition of claim 20, wherein said purified thermostable nucleic acid polymerase is a DNA polymerase from a species of the genus Thermus.*

*29. The composition of claim 21, wherein said purified thermostable nucleic acid polymerase is a DNA polymerase from a species of the genus Thermus.*

*30. The composition of claim 22, wherein said purified thermostable nucleic acid polymerase is a DNA polymerase from a species of the genus Thermus.*

*31. The composition of claim 23, wherein said purified thermostable nucleic acid polymerase is a DNA polymerase from a species of the genus Thermus.*

*32. The composition of claim 24, wherein said purified thermostable nucleic acid polymerase is a DNA polymerase from a species of the genus Thermus.*

*33. The composition of claim 25, wherein said purified thermostable nucleic acid polymerase is a DNA polymerase from a species of the genus Thermus.*

34. The composition of claim 26, wherein said purified thermostable nucleic acid polymerase is a DNA polymerase from a species of the genus Thermus.

35. The composition of claim 27, wherein said species is Thermus flavus.

36. The composition of claim 28, wherein said species is Thermus flavus.

37. The composition of claim 29, wherein said species is Thermus flavus.

38. The composition of claim 30, wherein said species is Thermus flavus.

39. The composition of claim 31, wherein said species is Thermus flavus.

40. The composition of claim 32, wherein said species is Thermus flavus.

41. The composition of claim 33, wherein said species is Thermus flavus.

42. The composition of claim 34, wherein said species is Thermus flavus.

43. The composition of claim 27, wherein said species is Thermus ruber.

44. The composition of claim 28, wherein said species is Thermus ruber.

45. The composition of claim 29, wherein said species is Thermus ruber.

46. The composition of claim 30, wherein said species is Thermus ruber.

47. The composition of claim 31, wherein said species is Thermus ruber.

48. The composition of claim 32, wherein said species is Thermus ruber.

49. The composition of claim 33, wherein said species is Thermus ruber.

50. The composition of claim 34, wherein said species is Thermus ruber.

51. The composition of claim 27, wherein said species is Thermus thermophilus.

52. The composition of claim 28, wherein said species is Thermus thermophilus.

53. The composition of claim 29, wherein said species is Thermus thermophilus.

54. The composition of claim 30, wherein said species is Thermus thermophilus.

55. The composition of claim 31, wherein said species is Thermus thermophilus.

56. The composition of claim 32, wherein said species is Thermus thermophilus.

57. The composition of claim 33, wherein said species is Thermus thermophilus.

58. The composition of claim 34, wherein said species is Thermus thermophilus.

59. The composition of claim 27, wherein said species is Thermus aquaticus.

60. The composition of claim 28, wherein said species is Thermus aquaticus.

61. The composition of claim 29, wherein said species is Thermus aquaticus.

62. The composition of claim 30, wherein said species is Thermus aquaticus.

63. The composition of claim 31, wherein said species is Thermus aquaticus.

64. The composition of claim 32, wherein said species is Thermus aquaticus.

65. The composition of claim 33, wherein said species is Thermus aquaticus.

66. The composition of claim 34, wherein said species is Thermus aquaticus.

67. The composition of claim 59, wherein said DNA polymerase is a recombinant DNA polymerase.

68. The composition of claim 60, wherein said DNA polymerase is a recombinant DNA polymerase.

69. The composition of claim 61, wherein said DNA polymerase is a recombinant DNA polymerase.

70. The composition of claim 62, wherein said DNA polymerase is a recombinant DNA polymerase.

71. The composition of claim 63, wherein said DNA polymerase is a recombinant DNA polymerase.

72. The composition of claim 64, wherein said DNA polymerase is a recombinant DNA polymerase.

73. The composition of claim 65, wherein said DNA polymerase is a recombinant DNA polymerase.

74. The composition of claim 66, wherein said DNA polymerase is a recombinant DNA polymerase.

75. The composition of claim 67, wherein said recombinant DNA polymerase is expressed in E. coli.

76. The composition of claim 68, wherein said recombinant DNA polymerase is expressed in E. coli.

77. The composition of claim 69, wherein said recombinant DNA polymerase is expressed in E. coli.

78. The composition of claim 70, wherein said recombinant DNA polymerase is expressed in E. coli.

79. The composition of claim 71, wherein said recombinant DNA polymerase is expressed in E. coli.

80. The composition of claim 72, wherein said recombinant DNA polymerase is expressed in E. coli.

81. The composition of claim 73, wherein said recombinant DNA polymerase is expressed in E. coli.

82. The composition of claim 74, wherein said recombinant DNA polymerase is expressed in E. coli.

83. The composition of claim 27, wherein said species is Thermus lacteus.

84. The composition of claim 28, wherein said species is Thermus lacteus.

85. The composition of claim 29, wherein said species is Thermus lacteus.

86. The composition of claim 30, wherein said species is Thermus lacteus.

87. The composition of claim 31, wherein said species is Thermus lacteus.

88. The composition of claim 32, wherein said species is Thermus lacteus.

89. The composition of claim 33, wherein said species is Thermus lacteus.

90. The composition of claim 34, wherein said species is Thermus lacteus.

91. The composition of claim 27, wherein said species is Thermus rubens.

92. The composition of claim 28, wherein said species is Thermus rubens.

93. The composition of claim 29, wherein said species is Thermus rubens.

94. The composition of claim 30, wherein said species is Thermus rubens.

95. The composition of claim 31, wherein said species is Thermus rubens.

96. The composition of claim 32, wherein said species is Thermus rubens.

97. The composition of claim 33, wherein said species is Thermus rubens.

98. The composition of claim 34, wherein said species is Thermus rubens.

99. A reaction mixture that comprises nucleoside-5'-triphosphates, oligonucleotide primers, a buffer in which primer extension by a polymerase can occur, and an aliquot of a stable enzyme composition wherein said stable enzyme composition comprises a purified thermostable Thermus aquaticus DNA polymerase and a polyoxyethylated (20) sorbitan monolaurate alone or in combination with an ethoxylated nonyl phenol.

100. A reaction mixture that comprises nucleoside-5'-triphosphates, oligonucleotide primers, a buffer in which primer extension by a polymerase can occur, and an aliquot of a stable enzyme composition wherein said stable enzyme composition comprises a purified thermostable Thermus aquaticus DNA polymerase and an ethoxylated nonyl phenol alone or in combination with a polyoxyethylated (20) sorbitan monolaurate.

101. A reaction mixture that comprises nucleoside-5'-triphosphates, oligonucleotide primers, a buffer in which primer extension by a polymerase can occur, and an aliquot of a stable enzyme composition wherein said stable enzyme composition comprises a purified thermostable Thermus aquaticus DNA polymerase and an octylphenoxy polyethoxy ethanol compound.

102. A reaction mixture that comprises nucleoside-5'-triphosphates, oligonucleotide primers, a buffer in which primer extension by a polymerase can occur, and an aliquot of a stable enzyme composition wherein said stable enzyme composition comprises a purified thermostable Thermus thermophilus DNA polymerase and a polyoxyethylated (20) sorbitan monolaurate alone or in combination with an ethoxylated nonyl phenol.

103. A reaction mixture that comprises nucleoside-5'-triphosphates, oligonucleotide primers, a buffer in which primer extension by a polymerase can occur, and an aliquot of a stable enzyme composition wherein said stable enzyme composition comprises a purified thermostable Thermus thermophilus DNA polymerase and an ethoxylated nonyl phenol alone or in combination with a polyoxyethylated (20) sorbitan monolaurate.

104. A reaction mixture that comprises nucleoside-5'-triphosphates, oligonucleotide primers, a buffer in which primer extension by a polymerase can occur, and an aliquot of a stable enzyme composition wherein said stable enzyme composition comprises a purified thermostable Thermus thermophilus DNA polymerase and an octylphenoxy polyethoxy ethanol compound.

105. The reaction mixture of any one of claims 99–101, wherein said Thermus aquaticus DNA polymerase is a recombinant DNA polymerase.

106. The reaction mixture of claim 105, wherein said DNA polymerase is expressed in E. coli.

107. The composition of claim 1, wherein said purified thermostable nucleic acid polymerase is a recombinant nucleic acid polymerase.

108. The composition of claim 107, wherein said recombinant nucleic acid polymerase is a recombinant DNA polymerase.

109. The composition of claim 1, wherein said buffer comprises from about 0.1% to about 0.5% volume/volume of each of said non-ionic polymeric detergents.

110. The composition of claim 1, wherein said buffer comprises two non-ionic polymeric detergents, each at 0.5% volume/volume.

111. A stable enzyme composition comprising a purified thermostable nucleic acid polymerase enzyme, a buffer that comprises one or more non-ionic polymeric detergents, and one or more of: nucleoside triphosphates, oligonucleotide primers, magnesium salt, or gelatin.

* * * * *